United States Patent
Mendiretta et al.

(10) Patent No.: US 9,623,098 B2
(45) Date of Patent: Apr. 18, 2017

(54) COMBINED MEASLES-HUMAN PAPILLOMA VACCINE

(75) Inventors: Sanjeev K. Mendiretta, Gujarat (IN);
Reinhard Glueck, Gujarat (IN);
Viviana Giannino, Catania (IT);
Giuseppina Cantarella, Catania (IT);
Francesca Scuderi, Catania (IT);
Martin Billeter, Zurich (CH); Agata Fazzio, Catania (IT)

(73) Assignee: Cadila Healthcare Limited, Ahmedabad (IN)

( * ) Notice: Subject to any disclaimer, the term of this patent is extended or adjusted under 35 U.S.C. 154(b) by 473 days.

(21) Appl. No.: 12/993,693

(22) PCT Filed: May 26, 2009

(86) PCT No.: PCT/IN2009/000302
§ 371 (c)(1),
(2), (4) Date: Feb. 10, 2011

(87) PCT Pub. No.: WO2010/079505
PCT Pub. Date: Jul. 15, 2010

(65) Prior Publication Data
US 2011/0129493 A1    Jun. 2, 2011

(30) Foreign Application Priority Data
May 26, 2008 (IN) .......................... 1113/MUM2008

(51) Int. Cl.
*A61K 39/015* (2006.01)
*A61K 39/12* (2006.01)
*A61K 39/165* (2006.01)
*A61K 39/00* (2006.01)

(52) U.S. Cl.
CPC ............ *A61K 39/015* (2013.01); *A61K 39/12* (2013.01); *A61K 39/165* (2013.01); *A61K 2039/5256* (2013.01); *A61K 2039/55527* (2013.01); *A61K 2039/55533* (2013.01); *A61K 2039/70* (2013.01); *C12N 2710/20034* (2013.01); *C12N 2760/18434* (2013.01); *C12N 2760/18443* (2013.01)

(58) Field of Classification Search
None
See application file for complete search history.

(56) References Cited

FOREIGN PATENT DOCUMENTS

WO    2004/076619 A2    9/2004

OTHER PUBLICATIONS

Vaccine. Apr. 16, 2008;26(17):2164-74. doi: 10.1016/j.vaccine. 2008.01.057. Epub Feb. 22, 2008 Induction of neutralising antibodies and cellular immune responses against SARS coronavirus by recombinant measles viruses. Liniger M, Zuniga A, Tamin A, Azzouz-Morin TN, Knuchel M, Marty RR, Wiegand M, Weibel S, Kelvin D, Rota PA, Naim HY.*
Hallez S et al. Phase I/II trial of immunogenicity of a human papillomavirus (HPV) type 16 E7 protein-based vaccine in women with oncogenic HPV-positive cervical intraepithelial neoplasia. Cancer Immunol Immunother. Jul. 2004;53(7):642-50. Epub Feb. 17, 2004.*
Liniger M et al. .Induction of neutralising antibodies and cellular immune responses against SARS coronavirus by recombinant measles viruses. Vaccine. Apr. 16, 2008;26(17):2164-74. doi: 10.1016/j.vaccine.2008.01.057. Epub Feb. 22, 2008.*
Brandler S et al. Pediatric measles vaccine expressing a dengue antigen induces durable serotype-specific neutralizing antibodies to dengue virus. PLoS Negl Trop Dis. Dec. 12, 2007;1(3):e96.*
Hallez S et al. Phase I/II trial of immunogenicity of a human papillomavirus (HPV) type 16 E7 protein-based vaccine in women with oncogenic HPV-positive cervical intraepithelial neoplasia. Cancer Immunol Immunother. Jul. 2004;53(7):642-50. Epub Feb. 17, 2004.*
Casana PH et al. Interleukin-2 inhibits proliferation of HPV-associated tumor cells and halts tumor growth in vivo. Biochem Biophys Res Commun. Dec. 20, 2002;299(5):818-24.*
Calain P, Roux L. Generation of measles virus defective interfering particles and their presence in a preparation of attenuated live-virus vaccine. J Virol. Aug. 1988;62(8):2859-66.*
Schlegel R, Phelps WC, Zhang YL, Barbosa M. Quantitative keratinocyte assay detects two biological activities of human papillomavirus DNA and identifies viral types associated with cervical carcinoma. EMBO J. Oct. 1988;7(10):3181-7.*
Recommended Adult Immunization Schedule—United States, Oct. 2005—Sep. 2006. p. 1-6.*
GenBank: D00735.1. Human papillomavirus type 16 genes for E6 protein, E7 protein, E1-E4 fusion protein, partial and complete cds. Dated Oct. 4, 2007.*

(Continued)

*Primary Examiner* — Nick Zou
(74) *Attorney, Agent, or Firm* — Ladas & Parry LLP

(57) ABSTRACT

The present invention relates to combined vaccines against measles and human papilloma virus (HPV). In particular, the invention relates to recombinant measles virus vectors containing heterologous nucleic acid encoding single or several antigens derived from HPV, preferably, the major capsid antigen L1, the minor capsid antigen L2, the early gene E6 and the early gene E7 oncoproteins of HPV type 16, and optionally of types 18, 6 and 11. In a first embodiment, prophylactic vaccines are generated expressing HPV antigens, preferably L1 and/or L2 such that they induce a potent long-lasting immune response in mammals, preferably humans, to protect against HPV and MV infection. In another embodiment, therapeutic vaccines are generated expressing E6 and E7 proteins, and optionally L1 and L2, such that they induced strong immune responses will resolve persistent HPV infections at early or late stages, including HPV-induced cervical carcinoma. In a preferred embodiment, the combined vaccines are easy to produce on a large scale and can be distributed at low cost.

21 Claims, 34 Drawing Sheets

(56) References Cited

OTHER PUBLICATIONS

Breitburd et al. Human papillomavirus vaccines. Semin Cancer Biol. Dec. 1999;9(6):431-44.*
Frederic Tangy et al.: "Live attenuated measles vaccine as a potential multivalent pediatric vaccination vector" Viral Immunology, Mary Ann Liebert, Inc., New York, US LNKD-DOI:10.1089/VIM.2005.18.317, vol. 18, No. 2, Jun. 1, 2005 (Jun. 1, 2005), pp. 317-326, XP008088160 ISSN: 0882-8245.
Stanley Margaret A: "Human papillomavirus vaccines." May 2006 (May 2006), Reviews in Medical Virology May-Jun. 2006 LNKD-Pubmed: 16710836, Vol. 16, Nr. 3, pp. 139-149, XP002598089 ISSN: 1052-9276 p. 139-p. 140; table 1.
Rouzier, R. et al.: "Vaccination HPV: principes, résultats et perspectives" Journal De Gynécologie Obstetrique De La Re Producti On, vol. 36, 2007, pp. 13-18, XP002598090 p. 15-p. 16.
Drexler I et al: "Modified vaccinia virus Ankara as antigen delivery system: how can we best use its potential?" Current Opinion in Biotechnology, London, GB LNKD-DOI:10.1016/J.COPBIO.2004.09.001, vol. 15, No. 6, Dec. 1, 2004 (Dec. 1, 2004), pp. 506-512, XP004653482 ISSN: 0958-1669 abstract; p. 509.
Corona Gutierrez Carlos manual et al: "Clinical protocol. A phase II study: efficacy of the gene therapy of the MVA E2 recombinant virus in the treatment of precancerous lesions (NIC I and NIC II) associated with infection of oncogenic human papillomavirus." Jun. 10, 2002 (Jun. 10, 2002), Human Gene Therapy Jun. 10, 2002 LNKD-PUBMED:12067445, vol. 13, Nr. 9, pp. 1127-1140, XP002598091 ISSN: 1043-0342 p. 1128-p. 1129.
International Preliminary Report on Patentability mailed Jan. 21, 2011.
Written Opinion of the International Searching Authority mailed Sep. 17, 2010.
Response filed at the IPEA/EPO on Nov. 17, 2010 with attachment.
Reference No. 9—Clarisse Lorin, et. al., "A Single Injection of Recombinant Measles Virus Vaccines Expressing Human Immunodeficiency Virus (HIV) Type 1 Clade B Envelope Glycoproteins Induces Neutralizing Antibodies and Cellular Immune Responses to HIV", *Journal of Virology*, Jan. 2004, p. 146-157.
Reference No. 10—M. Singh et. al., "A Recombinant Measles Virus Expressing Hepatitus B Virus Surface Antigen Induces Humoral Immune Responses in Genetically Modified Mice," *Journal of Virology*, Jun. 1999, p. 4823-4828.
Reference No. 12 Philippe Despres, et. al. "Live Measles Vaccine Expressing the Secreted Form of the West Nile Virus Envelope Glycoprotein Protects against West Nile Virus Encephalitis," *The Journal of Infectious Diseases*, Jan. 15, 2005, 191:207-214.
Reference No. 13 Thomas Fehr, et. al., "T-cell independent IgM and enduring protective IgG antibodies induced by chimeric measles viruses," *Nature Medicine*, Aug. 1998, 4(8): 945-948.

\* cited by examiner p(+)MV2EZ-GFP

FIG. 4a

FIG. 4a continuation

FIG. 4a continuation

FIG. 4a continuation

```
12001 TTTGCTGGAG TGAAATTTGG CTGCTTTATG TGGATAGTGA TCTGACAATG TACCTAAAGG ACAAGGCACT TGCTGCTCTC CAAAGGGAAT 12100
12101 GGGATTCAGT TTACCCGAAA GAGTTCCTGC GTTACGACCC ACCGGGTCAC GCGAGCCTTGT AGATGTTTTC CTTAATGATT CGACCTTTGA 12200
12201 CCCATATGAT GTGATAATGT ATGTTGTAAG TGGAGCTTAC CTCCATGACC CTGAGTTCAA CCTGTCTTAC ACGGGATTGG CAAGGAAACA 12300
12301 GGTAGACTTT TTGCTAAAAT GACTTACACA ATGGAGCCAT GCCAAGTGAT TGCTGAAAAT CTAATCTCAA ACGGGATTGG AAGGACAATG 12400
12401 GGATGAGCAA GGATGACTAC GATTGACTA AGGCACTCCA CACTCTAGCT GTCTCAGGAG TCCCAAAGA AGTCACAGGG GGGGCCAGT 12500
12501 CTTAAAAACC TACTCCCGAA GCCCAGTCCA CACAAGTACC AGGAACGTGA GAGCAGCAAA AGGGTTTATA GGGTTCCCTC AAGTAATTCG GCAGGACCAA 12600
12601 GACACTGATC ATCCGGAGAA TATGGAAGCT TACGAGACAG TCAGTGCATT TATCACGACT GATCTCAAGA AGTACTGCCT TAATTGGAGA TATGAGACCA 12700
12701 TCAGCTTGTT TGCACAGAGG CTAAATGAGA TTTACGGATT GCCCTCATTT TTCCAGTGGC TGCATAAGAG GCTTGAGACC TCTGTCCTGT ATGTAAGTGA 12800
12801 CCCTCATTGC CCCCCCGACC TTGACGCCCA TATCCCGTTA ACCTGGCTGC CCAATGATCA AATCTTCATT AAGTACCCTA TGGGAGGTAT AGAAGGGTAT 12900
12901 TGTCAGAAGC TGTGGACCAT CAGCACCATT CCCTATCTAT CAACCTTAAG TTATGAGAGC GGAGTAAGGA TTGCTTCGTT AGTGCAAGGG GACAATCAGA 13000
13001 CCATAGCCGT AACAAAAAGG GTACCCAGCA CATGGCCCTA CAACCTTGTT AAAGGGAAG CTGCTAGAGAT TTTTGTCTAT TCAAAAGGAA TTCTTAGGCA 13100
13101 AAGGCTACAT GATATTGGCC ATCACCTCAA GGCAAATGAG ACAATTGTTT CATCACATTT TATAGTTCAT GAAACAAAGG CAGCATGCAG AATTCTGATC TGGCTACTT 13200
13201 GTGTCCCAAT CACTCAAGAG CATCGGCAAG TGTGTATTCT GGTCAGGAC TATAGTTGAT GAAACAAAGG CAGCATGCAG AATTCTGATC TCTCTTGGCT ACACAATTGG 13300
13301 CTAAAAGCAT CGAGAGAGTT ACCCGGGATG TATGACCGTT TTCCCTGAAC GTCCTAAAAG GATACAGCA AATTCTGATC TTGCCCGCTC CTATTGGCT TCAATCAA 13400
13401 TTCAACCATG ACCCGGATG TAGTCATACC AACAACGACC CCTCCTCACA CAGTAACATC TCTTAATAAG GATGCCACTG TTGCCCGCTC CTATTGGGG GATGAATTAT 13500
13501 CTGAATATGA GCAGGCTGTT TGTCAGAAAC ATCGGTGATC CAGTAACATC GAATGATCT CGCCTCACTA ATGCCTGAAG 13600
13601 AGACCCTCCA TCAAGTAATC ACACAACAAC CGGGGACTC TTTCATTCCTA GCCACCCTTA CTCAGCAAAT CTTGTATGTG TCCAGAGCAT 13700
13701 CACTAGACTC CTCAAGAACA TAACTGCAAG GTTTGTCCTG ATCCATAGTC CAAACCCAAT GTTAAAAGGA TTATTCCATG ATGACAGTAA AGAAGAGGAC 13800
13801 GAGGGACTGG CGGCATTCCT CATGGACAGG CATATTATAG TACCTAGGGC AGCTCATGAA ATCCTGGATC ATAGTGTCAC AGGGGCAAGA GAGTCTATTG 13900
13901 CAGGGATGCT GGATACCACA AAAGGCTTGA TTCGAGCCCAG CATGAGGAAG CCCTCGAGT GATAACCAGA TCAGTGCAGC TTGTCCAATT ATGACTATGA 14000
14001 ACAATTCAGA GCAGGGATGG TGCTATTGAC AGGAAGAAAG AGAAATGTCC CAGTGTCAGC TCAGTGCAGC TGGCGAGAGC TCTAAGAAGC 14100
14101 CATATGTGGG CGAGGCTAGC TCGAGGACGG CCTATTTACG GCCTTGAGGT CTAGAATCTA TGCGAGGCCA CCTTATTCGG CGTCATGAGA 14200
14201 CATGTGCAT CTGCGAGTGT GGATCAGTGA ACTACGGATG GTTTTTGTC GCCAACTGGA TGATATTGAC AAGGAAACAT CATCCTTGAG 14300
14301 AGTCCATAT ATGGTTCTA CCACTGATGA GAGAACAGAC ATGAAGCTTG CCTTCGTAAG CGATCCTTGC GATCTGCTGT TAGAATAGCA 14400
14401 ACAGTGTACT CATGGGCTTA CGGTGATGAT GATAGCTCTT GGAACGGAGC CGGTTGTTG GCTAGGCAAA GGGCCAATGT GAGCCTGGAG GAGCTAAGGG 14500
14501 TGATCACTCC CATCTCAACT TCGACTAATT TAGCGCATAG GTTGAGGGAT AAGTAGAAATA CTCAGGTACA TCCCTTGTCC GAGTGGCGAG 14600
14601 GTATACCACA ATCTCCAACG ACAATCTCTC ATTTGTCATA TCAGATAAGA TAACTTTATA TACCAACAAG GAATGCTCCT AGGGTTGGGT 14700
14701 GTTTTAGAAA CATTGTTTCG ACTCGAGAAA GATACCGGAT CATCTAACAC CTTCACGTCG AAACAGATTG TTGCGTGATC CCGATGATAG 14800
14801 ATCATCCCAG GATACCCAGC TCCCGCAAGC TAGAGCTGAG GGCAGAGCTA CATTGATATA TGATAATCA CCTTTAATTG ACAGAGATGC 14900
14901 AACAAGGCTA TACACCCAGA GCCATAGGAG GCACCTTGTG GAATTTGTTA CATGGTCCAC ACCCAACTA TATCACATTT TAGCTAAGTC CACAGCACTA 15000
15001 TCTATGATTG ACCTGGTAAC AAAATTGAG AAGGACCATA ATGGGGATG TTCAGCTCTC ATGGGCGATG ACGATATCAA TAGTTTCATA ACTGAGTTTC 15100
15101 TGCTCATAGA GCCAAGATTA TTCACTATCT ACTTGGGCCA GTGTGCGGCC CATTGATGT ACATTATCAT AGACCATCAT GAAATATCA 15200
```

FIG. 4a continuation

FIG. 4a continuation

```
18401 GCAGAGCGAG GTATGTAGGC GGTGCTACAG AGTTCTTGAA GTGGTGGCCT AACTACGGCT ACACTAGAAG GACAGTATTT GGTATCTGCG CTCTGCTGAA 18500
18501 GCCAGTTACC TTCGGAAAAA GAGTTGGTAG CTCTTGATCC GGCAAACAAA CCACCGCTGG TAGCGGTGGT TTTTTTGTTT GCAAGCAGCA GATTACGCGC 18600
18601 AGAAAAAAAG GATCTCAAGA AGATCCTTTG ATCTTTTCTA CGGGGTCTGA CGCTCAGTGG AACGAAAACT CACGTTAAGG GATTTTGGTC ATGAGATTAT 18700
18701 CAAAAAGGAT CTTCACCTAG ATCCTTTTAA ATTAAAAATG AAGTTTTAAA TCAATCTAAA GTATATATGA GTAAACTTGG TCTGACAGTT ACCAATGCTT 18800
18801 AATCAGTGAG GCACCTATCT CAGCGATCTG TCTATTTCGT TCATCCATAG TTGCCTGACT CCCCGTCGTG TAGATAACTA CGATACGGGA GGGCTTACCA 18900
18901 TCTGGCCCCA GTGCTGCAAT GATACCGCGA GACCCACGCT CACCGGCTCC AGATTTATCA GCAATAAACC AGCCAGCCGG AAGGGCCGAG CGCAGAAGTG 19000
19001 GTCCTGCAAC TTTATCCGCC TCCATCCAGT CTATTAATTG TTGCCGGGAA GCTAGAGTAA GTAGTTCGCC AGTTAATAGT TTGCGCAACG TTGTTGCCAT 19100
19101 TGCTACAGGC ATCGTGGTGT CACGCTCGTC GTTTGGTATG GCTTCATTCA GCTCCGGTTC CCAACGATCA AGGCGAGTTA CATGATCCCC CATGTTGTGC 19200
19201 AAAAAAGCGG TTAGCTCCTT CGGTCCTCCG ATCGTTGTCA GAAGTAAGTT GGCCGCAGTG TTATCACTCA TGGTTATGGC AGCACTGCAT AATTCTCTTA 19300
19301 CTGTCATGCC ATCCGTAAGA TGCTTTTCTG TGACTGGTGA GTACTCAACC AAGTCATTCT GAGAATAGTG TATGCGGCGA CCGAGTTGCT CTTGCCCGGC 19400
19401 GTCAATACGG GATAATACCG CGCCACATAG CAGAACTTTA AAAGTGCTCA TCATTGGAAA ACGTTCTTCG GGGCGAAAAC TCTCAAGGAT CTTACCGCTG 19500
19501 TTGAGATCCA GTTCGATGTA ACCCACTCGT GCACCCAACT GATCTTCAGC ATCTTTTACT TTCACCAGCG TTTCTGGGTG AGCAAAAACA GGAAGGCAAA 19600
19601 ATGCCGCAAA AAAGGGAATA AGGGCGACAC GGAAATGTTG AATACTCATA CTCTTCCTTT TTCAATATTA TTGAAGCATT TATCAGGGTT ATTGTCTCAT 19700
19701 GAGCGGATAC ATATTTGAAT GTATTTAGAA AAATAAACAA ATAGGGGTTC CGCGCACATT TCCCCGAAAA GTGC                             19774
          |         |         |         |         |         |         |         |         |         |
         10        20        30        40        50        60        70        80        90       100
```

FIG. 4a continuation p(+)MV3EZ-GFP

```
        1 CACCTAAATT GTAAGCGTTA ATATTTTGTT AAAATTCGCG TTAAATTTTT GTTAAATCAG CTCATTTTTT AACCAATAGG CCGAAATCGG CAAAATCCCT  100
      101 TATAAATCAA AAGAATAGAC CGAGATAGGG TTGAGTGTTG TTCCAGTTTG GAACAAGAGT CCACTATTAA AGAACGTGGA CTCCAACGTC AAAGGGCGAA  200
      201 AAACCGTCTA TCAGGGCGAT GGCCCACTAC GTGAACCATC ACCTAAATCA AGTTTTTTGG GGTCGAGGTG CCGTAAAGCA CTAAATCGGA ACCCTAAAGG  300
      301 GAGCCCCCGA TTTAGAGCTT GACGGGGAAA GCCgccatt taggccaTAG GGCGCTGGCA AGTGTAGCGG TCACGCTGCG CGTAACCACC ACACCCGCCG  400
      401 CGCTTAATGC GCCGCTACAG GGCGCGTCCC ATTCGCCATT CAGGCTGCGC AACTGTTGGG AAGGGCGATC GGTGCGGGCC TCTTCGCTAT TACGCCAGCT  500
      501 GGCGAAAGGG GGATGTGCTG CAAGGCGATT AAGTTGGGTA ACGCCAGGGT TTTCCCAGTC ACGACGTTGT AAAACGACGG CCAGTGAATT Gtaatacgac  600
      601 tcactataAC CAAACAAAGT TGGGTAAGGA TAGTTCAATC AATGATCATC TTCTAGTGCA CTTAGATTCC AAGATCCTAT TATCAGGGAC AAGAGCAGGA  700
      701 TTAGGGATAT CTGAGATGGC CACACTTTTA AGGAGCTTAG CATTGTTCAA AAGAAACAAG GACAAACCAC CCATTACATC AGGATCCGGT GGAGCCATCA  800
      801 GAGGAATCAA ACACATTATT ATAGTACCAA TCCCTGGAGA TTCCTCAATT ACCACTCGAT CCAGACTTCT GGACCGGTTG GTCAGGTTAA TTGGAAACCC  900
      901 GGATGTGAGC GGGCCCAAAC TAACAGGGGC ACTAATAGGT ATATTATCCT TATTTGTGGA GTCTCCAGGT CAATTGATTC AGAGGATCAC CGATGACCCT 1000
     1001 GACGTTAGCA TAAGGCTGTC AGAGGTTGTC AGTGATGACC AGTCACAATC TGGCCTTACC TTCGCATCAA GAGGTACCAA CATGGAGGAT GAGGCGGACC 1100
     1101 AATACTTTTC ACATGATGAT CCAATTAGTA CAGGTTCGGA AGTCAAATC TGGTTCGAGA ACAAGAAAT CTCAGATATT GAAGTGCAAG ACCCTGAGGG 1200
     1201 ATTCAACATG ATTCTGGGTA CCATCCTAGC GTCTTGCTCG CAAAGGCGGT TACGGCCCCA GACACGGCAG CTGATTCGGA GCTAAGAAGG 1300
     1301 TGGATAAAGT ACACCCAACA AAGAAGGGTA GTTGGTGAAT TTAGATTGGA GAGAAAATGG TTGGATGTGG TGAGGAACAG GATTGCCGAG GACCTCTCCT 1400
     1401 TACGCCGATT CATGGTCGCT CTAATCCTGA ATATCAAGAG AACACCCGGA AACAAACCCA GGATTGCTCA AATGATATGT GACATTGATA CATATATCGT 1500
     1501 AGAGGCAGGA TTAGCCAGTT TTATCCTGAC TATTAAGTTT GGGGATAGAA CTATGTATCC TGCTCTTGGA CTGGAGAACT TTGCTGGTGA GTTATCCACA 1600
     1601 CTTGAGTCCT TGATGAACCT TTACCAGCAA ATGGGGGAAA CTGCACCCTA CATGGTAATC CTGGAGAACT CAATTCAGAA CAAGTTCAGT GCAGGATCAT 1700
     1701 ACCCTCTGCT CTGGAGCTAT GCCATGGGAG TAGGAGTGGA ACTTGAAAAC TCCATGGGGG GTTTGAACTT TGGCCGATCT TACTTTGATC CAGCATATTT 1800
     1801 TAGATTAGGG CAAGAGATGG TAAGGAGGTC AGCTGGGAAG GTCAGTTCCA CATTGGCATC TGAACTCGGT ATCACTGCCG AGGATGCAAG GCTTGTTTCA 1900
```

FIG. 4b

```
1901 GAGATTGCAA TGCATACTAC TGAGGACAAG ATCAGTAGAG CGGTTGGACC CAGACAAGCC CAAGTATCAT TTCTACACGG TGATCAAAGT GAGAATGAGC 2000
2001 TACCAGATT  GGGGGCAAG  GAAGATAGGA GGGTCAAACA GAGTCGAAGA GAAGCCAGG  AGAGCTACAG AGAAACCCGG CCCAGCCAGA CAAGTGATGC 2100
2101 GAGAGCTGCC CATCTTCCAA CCGGCACACC CCTAGACATT GACACTGCAT CGGAGTCCAG CCAAGATCCG CAGGACAGTC GAAGGTCAGC TGACGCCCTG 2200
2201 CTTAGGCTGC AAGCCATGGC AGGAATCTCG GAAGAACAAG GCTCAGACAC GGACACCCCT ATAGTGTACA ATGACAGAAA TCTTCTAGAC TAGGTGCGAG 2300
2301 AGGCCGAGGG CCAGAACAAC ATCCGCCTAC CCTCCATCAT TGTTATAAAA AACTTAGGAA CCAGTCCCAC ACAGCCGCCA GCCCATCAAC CATCCACTCC 2400
2401 CACGATTGGA GCCAATGGTA GAAGAGCAGG CACGCCATGT CAAAAACGAA CTGGAATGCA TCCGGGCTCT CAAGGCCGAG CCCATCGGCT CACTGGCCAT 2500
2501 CGAGGAAGCT ATGGCAGCAT GGTCAGACAT ATCAGACAAC CCAGGACAGG AGCGAGCCAC CTGGAGGGAA GAGAAGGCAG GCAGTTCGGG TCTCAGAAAA 2600
2601 CCATGCCTCT CAGCAATTGG ATCAACTGAA GGCCGTGCAC CTCGCATCCG GGTCAGGGA  CCTGGAGAGA GCGATGACGA CGCTGAAACT TTGGAATCC  2700
2701 CCCCAAGAAA TCTCCAGGCA TCAAGCACTG GGTTACAGTG TTATTACGTT TATGATCACA GCGGTGAAGC GGTTAAGGA  ATCCAAGATG CTGACTCTAT 2800
2801 CATGGTTCAA CTGACCGGGG ATCGTGATAG CACCCTCTCA GGAGGAGACA TGAATCTGA  AAACAGCGAT GTGATATTG  AAGGAGGGA  CTCCGAGGGA 2900
2901 TATGCTATCA CTGACCGGGC ATCTGCTCCC GGTTCAGAGG TCTCAATGTT TTCTGATGTT GAAACTGCAG AAGGAGGGA  GATCACCGAG CTCCTGGAC  3000
3001 TCCAATCCAG AGGCAACAAC TTTCGAAGC  TTGGGAAAAC TCTCCTCCCC CGGACCCCGG TAGGGCCAGC ACTTCCGGGA CACCATTAA  3100
3101 AAAGGGCACA GACGCGAGAT TAGCCTCATT TGGAACGGAG CCTCCGAACC TATTGACAGG TGGTGCAACC CAATGTGCTC GAAAGTCACC CTCGAACCA  3200
3201 TCAGGGCCAG GTGCACCTGC GGGGAATGTC CCCGAGTGTG CGCACTGATA CAGGAGTGGA CACCCGAATC TGGTACCACA CGTCGGGTTC ATCTCCCGA  3300
3301 GATCCCAGAA TAATGAAGAA GGGGAGACT  ATTATGATGA TCTGATGTCC AAGATATTAA AACAGCCTTG GCCAAAATAC ATGATATCAA ACAGGATAA  3400
3401 TCAGAAGATA ATCTCCAAGC TAGAATCACT GCTGTTATTG AAGGAGAAG  TTGAGTCAAT TAAGAAGCAG ATCAACAGC  CATATCCACC 3500
3501 CTGGAAGGAC ACCTCTCAAG CATCATGATC GCCATTCCTG GACTTGGGAA GATCCCAAC  GACCCCACTG CAGATGTCGA AATCAATCCC GACTTGAAAC 3600
3601 CCATCATAGG CAGAGATTCA GGCCGAGCAC TGGCCGAAGT TCTCAAGAAA CCCGTTGCCA GCCGACAACT CCAAGAATG  ACAAATGGAC GGACCAGTTC 3700
3701 CAGAGGACAG GTGCACCTGC AATTTCAGCT AAAGCCGATC GGGAAAAAGA TGAGCTGCAG CGTCGGGTTT GTTCCTGACA ATTTGGGTCC ATCACGCAGT 3800
3801 GTAATCCGCT CCATTATAAA ATCGGACCGG CTAGAGGAGG ATCGGAAGGG ATGATATCAA AGGAGCCAAT GATCTGCCA  3900
3901 AGTTCCACCA GATGCTGATG AAGATAATAA TGAAGTAGCT ACAGCTCAAC TTACCTGCCA ACCCCATGCC AGTCGACCCA actagtACAA CCTAAATCAA 4000
4001 TCATAAAAAA CTTAGGAGCA AAGTGATTGC CTCCCAAGTT CCACACAATG AGAGATCTAC GACTTCGACA AGTCGGCATG GGACATCAAA GGGTCGATCG 4100
4101 CTCCGATACA CAGAGATTCA ACCCACCACC TACAGTGATG GCAGGCTGGT GCCCCAGGTC AGAGTCATAG AGGCGACAGG AAGGATGAAT GCTTTATGTA 4200
4201 CATGTTTCTG CTGGGGGTTG TTGAGGACAG GGATTCCCTA GGCCTCCAA  TCGGGCGAGC ATTTGGGTCC CTGCCCTTAG GTGTTGGCAG ATCCACAGCA 4300
4301 AAGCCCGAAA AACTCCTCAA CACACCTTGG GAGCTTGACA TAGTTGTTAG ACGTACAGCA GGGCTCAATG AAAAACTGGT GTTCTACAAC AACACCCCAC 4400
4401 TAACTCTCCT CACACCTTGG AGAAGGTCC  TAACAACAGG GAGTGTCTTC AACGCAAACC AAGTGCAA   TGCGGTTAAT CTGATACCGC TCGATACCCC 4500
4501 GCAGAGGTTC CGTGTTGTTT ATATGAGCAT CACCCGTCTT TCGGATAACG CGTTCCTAGA AGAATGCTGG AATTCAGATC GGTCAATGCA 4600
4601 GTGGCCTTCA ACCTGCTGGT GACCCTTAGG ATTGACAAGG CGATAGGCCC TGGGAAGATC ATCGACAATA CAGACAACT  TCCTGAGGCA ACATTTATAG 4700
4701 TCCACACTGG GCACACCGGC AGAAGAAGA  GTGAGTCTA  CTCTGCAGAT TATTGCAAAA TGAAAATGA  AAAGATGCAG TTCAAGGAA  ACTTGGGG   4800
4801 GATAGGGGC  ACCAGTCTTC ACATTAGAAG CACAGCCAAA ATGAGCAAGA CTCTCAATGC AGTAAGAAATC CAGGCAGTTT AGTTCCTCAA CCCGCTGATG 4900
4901 GATATCAATG AAGACCTTAA TCGATTACTC TGGAGGAGCA GATGCAAGAT TAGACCCGTAG ATGAAGAAT  CAGGCAGTTT TGCAGCCATC AGTTCCTCAA 5000
5001 TTTACGACGA CGTGATCATA AATGATGACC AAGGACTATT CAAAGTTCTG TAGACCCGTAG TGCCCAGCAA TGCCCGAAAA CGACCCCCCT CACAATGACA 5100
```

FIG. 4b continuation

```
5101 GCCAGAAGGC CCGGACAAAA AAGCCCCCTC CGAAAGACTC CACGGACCAA GCGAGAGGCC AGCCAGCAGC CGACGGCAAG CGCGAACACC AGGCGGCCCC 5200
5201 AGCACAGAAC AGCCCTGACA CAAGGCCACC ACCAGCCACC CCAATCTGCA TCCTCCTCGT GGGACCCCCG AGGACCAACC CCCAAGGCTG CCCCCGATCC 5300
5301 AAACCACCAA CCGCATCCCC CCACCCCCG GGAAAGAAAC CCCAGCAAT TGGAAGGCCC CTCCCCCTCT TCCTCAACAC AGAACTCCA CAACGAACC 5400
5401 GCAAGCGA CCGAGGTGAC GCATCCGACT CCCTAGACAG ATCCTCTCTC CCCGGCAAAC TAAACAAAAC TTAGGGCCAA GGAACATACA 5500
5501 CACCCAGCAG AACCCAGACC CCGGCCCACG GCGCCCACCC CCAACCCCC GACAACCAGA GCGAGCCCCC AACCAATCCC GCCGTCCCC CCGGTGCCCA 5600
5601 CAGGCAGGGA CACCCAGACC GGAACAGACC CAGCACCCACA CCATCGACAA TCCAAGACAGG GGGGCCCCCC CCAAAAAAAA GCCCAGGG GCCGACAGCC 5700
5701 AGCACCGCGA GGAAGCCCAC CCAACCCACA GCAACCAAAC CAGAACCCAG ACCACCCTGG GCCACCAGCT CCCAGACTCG GCCATCACCC 5800
5801 CGCAGAAAGG AAAGGCCACA ACCCCGCGAC CCCAGCCCGG ATCCGGCGGG GAGCCAACCA ACCCGAACCA GCACCCAAGA GCAATCCCCG AAGGACCCC 5900
5901 GAACCGCAAA GGACATCAGT ATCCCACAGC CTCTCCAAGT CCCCCGGTCT CCTCCTCTTC TCGAAGGGAC CAAAAGATCA ATCCACCACA CCCGACGACA 6000
6001 CTCAACTCCC CACCCCTAAA GGAGACACCG GGAATCCCAG AATCAAGACT CATCCAATGT CCATCAATGG TCTCAAGGTG AACGTCTCTG CCATATTCAT 6100
6101 GGCAGTACTG TTAACTCTCC AACACCCCAC CATTGGGGCA ATCTCTCTAA GATAGGGGTG GTAGGAATAG GAAGTGCAAG CTACAAAGTT 6200
6201 ATGACTCGTT CCAGCCATCA ATCATTAGTC ATAAAATTAA TGCCCAATAT AACTCTCCTC AATAACTGCA CGAGGTAGCA GATTGCAGAA TACAGGAGAC 6300
6301 TACTGAGAAC AGTTTTGGAA ATGCACTTAA CCAATTAGAG TGCAATGACC CAGAATATAA GACCGTTCA GAGTGTAGCT TCAAGTAGGA GACACAAGAG 6400
6401 ATTTGCGGGA GTAGTCCCTG CAGGTGCGGC CCTAGGCGTT GCCAGCAGCT CTCAGATAAC GGCCGGCATT GCACTTCACC AGTCCATGCT GAACTCTCAA 6500
6501 GCCATCGACA ATCGAGAGC GAGCCTGAA ACTACTAATC AGGCAATTGA GGCAATCAGGGC CAAGCAGGGC AGGAGATGAT ATTGGCTGTT CAGGGTGTCC 6600
6601 AAGACTACAT CAATAATGAG CTGATACCGT CTATGAACCA ACTATCTTGT GATTTAATCG GCCAGAAGCT CGGGCTCAAA TTGCTCAGAT ACTATACAGA 6700
6701 AATCCTGTCA TTATTTGGCC CCAGTTTACG GGACCCCATA TCTGCGGAGA TATCTATCCA GGCTTTGAGC TATGCGCTTG GAGGAGACAT CAATAAGGTG 6800
6801 TTAGAAAAGC TCCGATACAG TGGAGGTGAT TTACTGGGCA TCTTAGAGAG CAGAGGAATA AAGGCCCCGA TAACTCACGT CGACACAGAG TCCTACTTCA 6900
6901 TTGTCCTCAG TATAGCCTAT CCGACGCTGT CCGAGATTAA GGGGGTGATT GTCCACCGGC TAGAGGGGGT CTCGTACAAC ATAGGCTCTC AAGAGTGGTA 7000
7001 TACCACTGTG CCCAAGTATG CCAAGGGAAC TCCTCTGCTC CAAGAATGCC ATCTCGAATT TTGATGAGTC ATCGTGTACT TTCATGCCAG GGGGACTGT GTGCAGCCAA 7100
7101 AATGCCTTGT ACCGAGGGAAC CTAATAGCCA ATTGTGCATC AATCCTTTGC AAGTGTTACA CAACAGGAAC TGTGCTCGTA CACTCGTATC CGGGTCTTTT GGAACCGGT 7200
7201 TCATTTTATC ACAAGGGGAC GCTGCCGGT ACTGCGAGGTG AGTCGAGGTG AACGGCGTGA CAATCCAAGT GATCATTAAT AGGTATCCAG CAAGACCCTG ACAAGATCCT 7300
7301 AACATACATT GTCCTCCCAT ATCATTGGAG AGGTTGGACG TAGGGACAAA AACGGCGTGA TAGGGACATA CGGGAGCAGG GCAATTGCTA AGTTGGAGGA TGCCAAGGAA ACGCTGTGTA CTTGCACAGA 7400
7401 ATTGACCTCG GATATTGAAG AGTATGAAAG GTTTATCGAG GTTTGGACG CACTAGCATA CGGGAGCAGG TGATTGCAGT AGTTGGAGGA TGCCAAGGAA TTGTTGGAGT 7500
7501 CATCGGACCA TGCTGCAGGG GGCGTTGTAA CAAAAGGGA GTAGTCAAG GAACAAGTTG GTCTACATCC ACCAGCCTA AGCCTGATC GGGTTGATAG GGATCCCCGC 7600
7601 TTTAATATGT CGCTCTGATC CCCTCTGGCC CTCTACAACT CTTGAAACAC AAATGTCCCA GTATGTCAGT ACCAGCCCTA TTACGGAAC ATCAAAATCC 7700
7701 TATGTAAGGT TCTCCGGCTT AACCCCCATC GAAGGGAAAG GTTGCTAGCC ATTGCAGGCA CAAGTCTCCT CTTCGTCATC GCACCCAGC CGAACCAGGA 7800
7801 CCTGAAATTA TCTGTTTGTC ATGTTTCTGA GCTTGATCGG GTTGCTAGCC ATTGCAGGCA TTAGACTTCA TCGGGCACCG ATCTACACCG CAGAGATCCA CGAGACCGGA 7900
7901 AAATGCCTTT ATGTTTGTC ATGTTTCTGA GCTTGATCGG GTTGCTAGCC ATTGCAGGCA ATTAACAGAG AACATCTTAT GATTGATAGA CCTTATGTTT TAAAAGCCTC 8000
8001 TCTGTTTGTC ATGTTTCTGA GCTTGATCGG GTTGCTAGCC ATTGCAGGCA TTAGACTTCA TCGGGCACCG ATCTACACCG CAGAGATCCA TGCTGGCTGT 8100
8101 AGCACCAATG TAGATGTAAC TAACTCAATC GAGCATCAGG TCAAGGACGT GCTGACACA CTCTTCAAAA TCATCGGTGA TGAAGTGGGC CTGAGGACAC 8200
8201 CTCAGAGATT CACTGACCTA GTGAAATTCA GATTAAATTC CTTAATCCGG ATAGGGAGTA CGACTTCAGA GATCTTCACTT GGTGTATCAA 8300
```

FIG. 4b continuation

```
8301 CCCGCCAGAG AGAATCAAAT TGGATTATGA TCAATACTGT GCAGATGTGG CTGCTGAAGA GCTCATGAAT GCATTGGTGA ACTCAACTCT ACTGAGACC  8400
8401 AGAACAACCA ATCAGTTCCT AGCTGTCTCA AAGGAAACT CTATAGTCAC AATGTGTCAT CACTACAATC AGAGGTCAAT TCTCAAACAT GTCGCTGTCC CTGTTAGACT  8500
8501 TGTATTTAGG TCGAGGTTAC AATGTGTCAT CTATAGTCAC AATGTGTCAT CAGGGAATGT ATGGGGAAC TTACCTAGTG GAAAAGCCTA ATCTGAGCAG  8600
8601 CAAAAGGTCA GAGTTGTCAC AACTGAGCAT GTACCGAGTG TTTGAAGTAG GTGTTATCAG AAATCCGGGT TTGGGGCTC CGGTGTTCCA TATGACAAAC  8700
8701 TATCTTGAGC AACCAGTCAG TAATGATCTC AGCAACTGTA GCTTGGCTTT GGGGAGCTC AAACTCGCAG CCCTTTGTCA CGGGGAAGAT TCTATCACAA  8800
8801 TTCCTATCA GGGATCAGGG AAAGGTGTCA GCTTCCAGCT CGTCAAGCTA GGTGTCTGGA AATCCCAAC CGACATGCAA TCCTGGGTCC CCTTATCAAC  8900
8901 GGATGATCCA GTGATAGACA GGCTTTACCT CTCATCTCAC AGAGGTGTTA TCGCTGACAA TCAAGCAAAA TGGGCTGTCC CGACAACACG AACAGATGAC  9000
9001 AAGTTGCGAA TGGAGACATG CTTCCAACAG GCGTGTAAGG GTAAAATCCA AGCACTCTGC GAGAATCCCG AGTGGGCACC ATTGAAGGAT AACAGGATTC  9100
9101 CTTCATACGG GGTCTTGTCT GTTGATCTGA GTCTGACAGT TGAGCTTAAA ATCGGGGATT CTTGGGCACC CGGGCCATTG ATCACACACG GTTCAGGGAT  9200
9201 GGACCTATAC AAATCCAACC ACAACAATGT GTATTGGCTG ACTATCCCGC CAATGAAGAA CCTAGCCTTA GGTGTAATCA ACACATTGGA GTGGATACCG  9300
9301 AGATTCAAGG TTAGTCCCTA CCTCTTCACT GTCCCAATTA AGGAAGCAGG CGAAGACTGC CATGCCCCAA CATACCTACC TGCCGAGGTG GATGGTGATG  9400
9401 TCAAACTCAG TTCCAATCTG GTGATTCTAC CTGGTCAAGA TCTCCAATAT GTTTTGGCAA CCTACGATAC TTCCAGGGTT GAACATGCTG TGGTTTATTA  9500
9501 CGTTTACAGC CCAGGCCGCT CATTTCTTA CTTTTATCCT TTTAGGTTGC CTATAAAGGG GGTCCCCATC GAATTACAAG TGGAATGCTT CACATGGGAC  9600
9601 CAAAAACTCT GGTGCCGTCA CTTCTGTGTG CTTGCGGACT CAGAATCTGG TGGACATATC ACTCACTCTG GATGGTGGG CATGGGAGTC AGCTGCACAG  9700
9701 TCACCCGGGA AGATGGAACC AATCGCAGAT AGGGCTGCTA GTGAACCAAT CACCCAGACA TCAGGCATAC CCactagtct acccccatc ACTGGAGACC  9800
9801 attgttataa aaaacttagg accaagtcc cagcaccgc aacaaatttc agcgcgcatg agtaaaggag aagaactttt cactgaagtt  9900
9901 gtcccaattc ttgttgaatt agatggtgat gttaatgggc acaaatttc tgtcagtgga gaggtgaag atacgaaaa cttacctta  10000
10001 aatttatttg cactactgga aaactacctg ttccatggcc aacacttgtc actactttca cctatggtgt tcaagatacc cagatatat  10100
10101 gaaacggcat gactttttca gactttttca gccgaaggt aacacttgtc aaagaactat attttttcaaa gatgacggga actacaagac acgtgctgaa  10200
10201 gtcaagtttg aaggtgatac ccttgttaat agatcgagt tgatttttaa gaagatgaa acattcttgg acaaaattg gaatacaact  10300
10301 ataactcaca caatgtatac atcatggcag acaaacaaaa gaatgaatc agagttaact tcaaaattag aacacaacatt gaagatgaa gcgttcaact  10400
10401 agcagaccat tatcaacaaa atactccaat tggcgatggc cctgtcttt taccagacaa ccattacctg tccacacaat ctgccctttc gaaagatccc  10500
10501 aacgaaaaga gagaccacat ggtccttctt gagtttgtaa cagctgctgg gattacacat ggcatggatg aactataaaa atagtgagcg cgcaggctg  10600
10601 acgtctgcg atgatactag tGTGAAATAG ACATCAGAAT TAAGAAAAAC GTAGGGTCCA AGTGGTTCCC CGTTATGGAC TCGCTATCTG TCAACCAGAT  10700
10701 CTTATACCCT GAAGTTCACC TAGATAGCCC GATAGTTACC AATAAGATAG TAGCCATCCT GGAGTATGCT ATAAACAATG TGGAAGTTGG ACCCTTACAG  10800
10801 CCTACACTGT GTCAGAACAT CAAGCACCGC CTAAAAACG GATTTTCCAA CCAAATGATT ATAAACAATG TGGAAGTTGG GAATGTCATC AAGTCCAAGC  10900
10901 TTAGGAGTTA TCCGGCCCAC TCTCATATTC CATATCCAAA TTGTAATCAG GATTTATTTA ACATAGAAGA CAAAGAGTCA ACGAGGAAGA TCCGTGAACT  11000
11001 CCTCAAAAAG GGGAATTCGC TGTACTCCAA AGTCAGTGAT AAGCTTAAG GGACACTAAC TCACGGCTTG GCCTAGGCTC CGAATTGAGG  11100
11101 GAGGACATCA AGGAGAAAGT TATTAACTTG GGAGTTTACA TGCACAGCTC CCAGTGGTTT GAGCCCTTTC TGTTTTGGTT TACAGTCAAG ACTGAGATGA  11200
11201 GGTCAGTGAT TAAATCACAA ACCCATACTT GCCATAGGAG GAGACACACA CCTGTATTCT TCACTGGTAG TTCAGTTGAG TTGCTAATCT CTCGTGACCT  11300
11301 TGTTGCTATA ATCAGTAAAG AGTCTCAACA TGTATATTAC AACTGGTTT GATGTATTGT AGGGGAGGTT AATGACAGAG  11400
11401 ACCGCTATGA CTATTGATGC TAGGTATACA GAGCTTCTAG GAAGAGTCAG AATACATGTGG AAACTGATAG ATGGTTTCTT CCCTGCACTC GGGAATCCAA  11500
```

FIG. 4b continuation

| | | | | | | | |
|---|---|---|---|---|---|---|---|
|11501|CTTATCAAAT|TGTAGCAATG|CTGGAGCCTC|TTTCACTTGC|TTACCTGCAG|CTGAGGGATA|TAACAGTAGA|ACTCAGAGGT|GCTTTCCTTA|ACCACTGCTT|11600|
|11601|TACTGAAATA|CATGATGTTC|TTGACCAAAA|CGGGTTTTCT|GATGAAGGTA|CTTATCATGA|GTTAATTGAA|GCTCTAGATT|ACATTTTCAT|AACTGATGAC|11700|
|11701|ATACATCTGA|CAGGGGAGAT|TTTCTCATTT|TTCAGAAGTT|TCGGCCACCC|CAGACTTGAA|GCAGTAACGG|CTGCTGAAAA|TGTTAGGAAA|TACATGAATC|11800|
|11801|AGCCTAAAGT|CATTGTGTAT|GAGACTCTGA|TGAAAGGTCA|TGCCATATTT|TGTGGAATCA|TAATCAACGG|CTATCGTGAC|AGGCACGGAG|GCAGTTGGCC|11900|
|11901|ACCCTGACCC|CTCCCCCTGC|ATGCTGCAGA|CACATCCGG|CCTCTTAGCC|CTTCAGGTGA|CATGAGCAGT|CTATCGTGAC|GGTTGATAA|CTGGAAATCT|12000|
|12001|TTTGCTGGAG|TGAAATTTGG|TGGATAGTGA|CCTCTTAGCC|TGGATAGTGA|TCTGACAATG|TACCTAAAGG|ACAAGGCACT|TGCTGCTCTC|CAAAGGGAAT|12100|
|12101|GGGATTCAGT|TTACCCGAAA|GAGTTCCTGC|GTTACGACCC|TCCCAAGGGA|ACCGGGTCAC|GGAGGCTTGT|AGATGTTTTC|CTTAATGATT|CGAGCTTTGA|12200|
|12201|CCCATATGAT|GTGATAATGT|ATGTTGTAAG|TGGAGCTTAC|CTCCATGACC|CTGAGTTCAA|CCTGTCTTAC|AGCCTGAAAG|AAAAGGAGAT|CAAGGAAACA|12300|
|12301|GGTAGACTTT|TTGCTAAAAT|GACTTACAAA|ATGAGGGCAT|GCCAAGTGAT|TGCTGAAAAT|CTAATCTCAA|ACGGGATTGG|CAAATATTTT|AAGGACAATG|12400|
|12401|GGATGGCCAA|GGATGAGCAC|GATTTGACTA|AGCACTCCA|CACTCTAGCT|GTCTCAGGAG|TCCCCAAAGA|TCTCAAAGAA|AGTCACAGGG|GGGGCCAGT|12500|
|12501|CTTAAAAACC|TACTCCCGAA|GCCCAGTCCA|CACAAGTACC|AGGAACGTGA|GAGCAGCAAA|AGGGTTTATA|GGGTTCCCTC|AAGTAATTCG|GCAGGACCAA|12600|
|12601|GACACTGATC|ATCCGGAGAA|TATGGAAGCT|TACGAGACAG|TCAGTGCATT|TATCACGACT|GATCTCAAGA|GTACTGCCT|TAATTGGAGA|TATGAGACCA|12700|
|12701|TCAGCTTGTT|TGCACAGAGG|CTAAATGAGA|TTTACGGATT|GCCCTCATTT|TTCCAGTGGC|TGCATAAGAG|GCTTGAGACC|TCTGTCCTGT|ATGTAAGTGA|12800|
|12801|CCCTCATTGC|CCCCCGACC|TTGACGCCCA|TATCCCGTTA|TATAAAGTCC|CCAATGATCA|AATCTTCATT|AAGTACCCTA|TGGGAGGTAT|AGAAGGGTAT|12900|
|12901|TGTCAGAAGC|TGTGGACCAT|CAGCACCATT|CCCTATCTAT|ACCTGGCTGC|TTATGAGAGC|GGAGTAAGGA|TTGCTTCGTT|AGTGCAAGGG|GACAATCAGA|13000|
|13001|CCATAGCCGT|AACAAAAAGG|GTACCCAGCA|CATGGCCCTA|CAACCTTAAG|AAACGGGAAG|CTGCTAGAGT|AACTAGAGAT|TACTTTGTAA|TTCTTAGGCA|13100|
|13101|AAGGCTACAT|GATATTGGCC|ATCACCTCAA|GGCAAATGAG|ACAATTGTTT|CATCACATTT|TTTTGTCTAT|GAAAAGGAA|TATATTATGA|TGGGCTACTT|13200|
|13201|GTGTCCCAAT|CACTCAAGAG|CATCGCAAGA|TGTGTATTCT|GGTCAGAGAC|TATAGTTGAT|GAAACAAGGG|CAGCATGCAG|AATTCTGATC|ACAACAATGG|13300|
|13301|CTAAAGCAT|CGAGAGAGGT|TATGACCGTT|ACCTTGCATA|TTCCCTGAAC|GTCCTAAAAG|TGATACAGCA|AATTCTGATC|TCTCTTGGCT|TCACAATCAA|13400|
|13401|TTCAACCATG|ACCCGGGATG|TAGTCATACC|CCTCCTCACA|AACAACGACC|TCTTAATAAG|GATGGCACTG|GATCTCAAGA|CTATTGGGGG|GATGAATTAT|13500|
|13501|CTGAATATGA|GCAGGTCTGT|TGTCAGAAAC|ATCGGTGATC|CGGGGGACTC|TTCATTCCTA|ATCAATTGCT|GATCTCAAGA|CGCCTCACTA|ATGCCTGAAG|13600|
|13601|AGACCCTCCA|TCAAGTAATG|ACACAACAAC|TAACTGCAAG|GTTTGTCCTG|ATCCATAGTC|GACTGGGCTA|GCGACCCTTA|CTTGTATGTG|TCCAGAGCAT|13700|
|13701|CACTGACTC|CTCAAGAACA|TAACTGCAAG|GTTTGTCCTG|CATATTATAG|TACCTAGGGC|CAAACCAAT|GTTAAAAGGA|TTATTCCATG|ATGACAGTAA|AGAAGAGGAC|13800|
|13801|GAGGGACTGG|CGGCATTCCT|CATGGACAGG|TTCGAGCCAG|CATGAGGAAG|AGCTCATGAA|ATCCTCGAGT|GATAACCAGA|AGGGGCAAGA|GAGTCTATTG|13900|
|13901|CAGGCATGCT|GGATACCACA|AAAGGCTTGA|TTCCAGCCAG|AGGAAGAAAG|GGGGGTTAA|CCTCTCGAGT|TCAGTGCAGC|TGGCGAGAGC|ATGACTATGA|14000|
|14001|ACAATTCAGA|GCAGGATGG|TGCTATTGAC|TCGAGGACGG|CCTATTTACG|AGAAATGTCC|TCATTGACAA|AGAGTCATGT|TGCCGAGAGC|TCTAAGAAGC|14100|
|14101|CATATGTGGG|CGAGGCTAGC|CGAGGACGG|CCTATTTACG|ACTACGGATG|GCCTTGAGGT|CCCTGATGTA|CTAGAATCTA|TGCGAGGCCA|CCTTATTCGG|CGTCATGAGA|14200|
|14201|CATGTGTCAT|CTGCGAGTGT|ATTGGTTCTA|CCACTGATGA|GAGAACAGAC|GTTTTTTGTC|CCTCGGGTT|GCCAACTGGA|TGATATTGAC|AAGGAAACAT|CATCCTTGAG|14300|
|14301|AGTCCCATAT|CATGGGCTTA|CGGTGATGAT|GATAGCTCTT|ATGAAGCTTG|ATGAAGGAGC|CCTTCGTAAG|AGCCCCAAGT|CGATCTGCT|GATCCTGGAG|TAGAATAGCA|14400|
|14401|ACAGTGTACT|CATGGGCTTA|CGGTGATGAT|GATAGCTCTT|ATGAAGCTTG|ATGAAGAAGC|CTGGTTGTTG|GCTAGGCAAA|GCCCAATGT|GATCTGCT|TAGAATAGCA|14500|
|14501|TGATCACTCC|CATCTCAACT|TCGACTAATT|TAGCCATAG|GTTGAGGGAT|CGTAGCACTC|AAGTGAAATA|GCTCAGGACA|TCCCTTGTCC|GAGTGGCGAG|14600|
|14601|GTATACCACA|ATCTCCAACG|ACAATCTCTC|ATTTGTCATA|TCAGATAAGA|AGGTTGATAC|TAACTTTATA|TACCAACAAG|GAATGCTCCT|AGGGTTGGGT|14700|

FIG. 4b continuation

```
14701 GTTTTAGAAA CATTGTTTCG ACTCGAGAAA GATACCGGAT CATCTAACAC GGTATTACAT CTTCACGTCG AAACAGATTG TTGCGTGATC CCGATGATAG 14800
14801 ATCATCCCAG GATACCCAGC TCCCGCAGCC TAGAGCTGAG GGCAGAGCTA TGTACCAACC CATTGATATA TGATAATGCA CCTTTAATTG ACAGAGATGC 14900
14901 AACAAGGCTA TACACCCAGA GCCATAGGAG GCACCTTGTG GAATTTGTTA CATGTCCAC ACCCCAACTA TATCACATTT TAGCTAAGTC CACACCACTA 15000
15001 TCTATGATTG ACCTGGTAAC AAAATTTGAG AAGGACCATA TGAATGAAAT TTCAGCTCTC ATAGGGGATG ACGATATCAA TAGTTTCATA ACTGAGTTTC 15100
15101 TGCTCATAGA GCCAAGATTA TTCACTATCT CGTTCCTTTC GTGTGCGGCC ATCAATTGGG CATTTGATGT ACATTATCAT AGACCATCAG GGAAATATCA 15200
15201 GATGGGTGAG CTGTTGTCAT CGTATTATAGA TAGAATGAGC AAAGGAGTGT TTAAGGTGCT TGTCAATGCT ACAACTGTGT CTAAGCCACC CAAAGATCTA CAAGAAATTC 15300
15301 TGGCATTGTG GTATTATAGA GCCTATCCAT GGTCCTTCAC TTGATGCTCA AAACTTGCAC ACAACATGGT GCAACATGGC TTACACATGC TATTATGACCT 15400
15401 ACCTCGACCT GTTGTTGAAT GAAGAGTTAC AAGAGTTCAC ATTTCTCTTG TGTGAAAGCG ACGAGGATGT AGTACCGGAC AGATTCGACA ACATCCAGGC 15500
15501 AAAACACTTA TGTGTTCTGG CAGATTTGTA CTGTCAACCA GGGACCTGCC CACCAATTCG AGGTCTAAGA CCGGTAGAGA AATGTGCAGT TCTAACCGAC 15600
15601 CATATCAAGG CAGAGCCTAT GTTATCTCCA GCAGGATCTT CGTGGAACAT AAATCCAATT ATTGTAGACC ATTACTCATG CTCTCTGACT TATCTCCGGC 15700
15701 GAGGATCGAT CAAACAGATA AGATTGAGAG TTGATCCAGG ATTCATTTTC GACGCCCTCG CTGAGGTAAA TGTCAGTCAG CCAAAGATCG GCAGCAACAA 15800
15801 CATCTCAAAT ATGAGCATCA AGGCTTTCAG ACCCCACAC GATGATGTTG CAAAATTGCT CAAAGATATC AACACAAGCA AGCACAATCT TCCCATTTCA 15900
15901 GGGGGCAATC TCGCCAATTA TGAAATCCAT GCTTTCCGCA GCTTGCTACA AAGCTGTTGA GATATCAACA TTAATTAGGA 16000
16001 GATGCCTTGA GCCAGGGGAG GACGGCTTGT TCTTGGGTGA GGGATCGGGT TCTATGTTGA TCACTTATAA GGAGATACTT AAACTAAACA AGTGCTTCTA 16100
16101 TAATAGTGGG GTTTCCGCCA ATTCTAGATC TGGTCAAAGG TGGTTAGCAC CCTATCCCTC CGAAGTTGGC CTTGTCGAAC ACAGAATGGG AGTAGGTAAT 16200
16201 ATTGTCAAAG TGCTCTTTAA CGGGAGGCCC GAAGTCACGT GGGTAGGCAG TGTAGATTCA TTCAATTTCA TATCCCTACC TCTAGTGTGG 16300
16301 GGTTTATCCA TTCAGATATA GAGACCTTGC CTATATAGAG AAGCTAGAGG AATTGGCAGC CATCTTATCG ATGGCTCTGC TCCTGGGCAA 16400
16401 AATAGGATCA ATACTGGTGA TTAAGCTTAT GCCTTTCAGC GGGGATTTTG TTCAGGGATT TATAAGTTAT GTAGGTCTC ATTATAGAGA AGTGAACCTT 16500
16501 GTATACCCTA GATAGCAA CTTCATATCT ACTGAATCTT ATTTGGTTAT GACAGATCTC AAGGCTAACC GGCTAATGAA TCCTGAAAAG ATTAAGCAGC 16600
16601 AGATAATTGA ATCATCTGTG AGGACTTCAC CTGGACTTAT AGGTCACATC CTATCCATTA AGCAACTAAG CTGCATACAA GCAATTGTGG GAGACGCAGT 16700
16701 TAGTAGAGGT GATATCAATC CTACTCTGAA AAAACTTACA CCTATAGAGC AGTGCTGAT CAATTGCGGG TTGGCAATTA ACGGACCTAA GCTGTGCAAA 16800
16801 GAATTGATCC ACCATGATGT TGCCTCAGGG CAAGATGGAT TGCTTAATTC TATACTCATC CTCTACAGGG AGTTGGCAAG ATTCAAAGAC AACCAAAGAA 16900
16901 GTCAACAAGG GATGTTCCAC GCTTACCCCG TATTGGTAAG TAGCAGGCAA CGAGAACTTA TATCTAGGAT CACCCGCAAA TTTTGGGGGC ACATTCTTCT 17000
17001 TTACTCCGGG AACAGAAAGT TGATAAATAA GTTTATCCAG AATCTCAAGT CCGGCTATCT GATACTAGAC TTACACCAGA ATATCTTCGT TAAGAATCTA 17100
17101 TCCAAGTCAG CCTGATTAAG GACTAATTGG TTGAACTCCG GGTTTTTAAG GTAACAGTCA AGGAGACCAA AGAATGGTAT AAGTTAGTCG 17200
17201 GATACAGTGC CCTGATTAAG GACTAATTGG TTGAACTCCG CCTGCCCTAG GAACCCTAAT GGGGTTTGA AACGTGAGTG ATTATTTGCA ATATATTAAA GAAAACTTTG 17300
17301 AAAATACGAG GTTTCTATTC CCAGCTTTGT CTGGTgccg gcatggtcc agcctcctcg ctggcgcgg ctggcaaca ttccgagggg acgtcccct 17400
17401 cgtaatgc gaatgatgacG CGGCcgatcc ggctgctaac aaagcccgaa cttgagcggt aggaagctga gttgtgct gccaacgctg agcataacct agcataaccc 17500
17501 cttgggccc ctaaacgggt cttgagggt tttttgctga aaggaggaac tatatccgga tgCGGCCCa GGTACCCCGC TTTTGTTCCC acgtccccct 17600
17601 gttaattTCG AGCTTGGCGT AATCATGGTC ATAGCTGTTT CCTGTGTGAA ATTGTTATCC GCTCACAATT CCACACAACA TACGAGCCGG AAGCATAAAG 17700
17701 TGTAAAGCCT GGGGTGCCTA ATGAGTGAGC TAACTCACAT TAATTGCGTT GCGCTCACTG CCCGCTTTCC AGTCGGGAAA CCTGTCGTGC CAGCTGCATT 17800
17801 AATGAATCGG CCAACGCGCG GGGAGAGGCG GTTTGCGTAT TGGGCGCTCT TCCGCTTCCT CGCTCACTGA CTCGCTGCGC TCGGTCGTTC GGCTGCGGCG 17900
```

FIG. 4b continuation

```
17901 AGCGGTATCA GCTCACTCAA AGGCGGTAAT ACGGTTATCC ACAGAATCAG GGGATAACGC AGGAAAGAAC ATGTGAGCAA AAGGCCAGCA AAAGGCCAGG 18000
18001 AACCGTAAAA AGGCCGCGTT GCTGGCGTTT TTCCATAGGC TCCGCCCCCC TGACGAGCAT CACAAAAATC GACGCTCAAG TCAGAGGTGG CGAAACCCGA 18100
18101 CAGGACTATA AAGATACCAG GCGTTTCCCC CTGGAAGCTC CCTCGTGCGC TCTCCTGTTC CGACCCTGCC GCTTACCGGA TACCTGTCCG CCTTTCTCCC 18200
18201 TTCGGGAAGC GTGGCGCTTT CTCATAGCTC ACGCTGTAGG TATCTCAGTT CGGTGTAGGT CGTTCGCTCC AAGCTGGGCT GTGTGCACGA ACCCCCCGTT 18300
18301 CAGCCCGACC GCTGCGCCTT ATCCGGTAAC TATCGTCTTG AGTCCAACCC GGTAAGACAC GACTTATCGC CACTGGCAGC AGCCACTGGT AACAGGATTA 18400
18401 GCAGAGCGAG GTATGTAGGC GGTGCTACAG AGTTCTTGAA GTGGTGGCCT AACTACGGCT ACACTAGAAG GACAGTATTT GGTATCTGCG CTCTGCTGAA 18500
18501 GCCAGTTACC TTCGGAAAAA GAGTTGGTAG CTCTTGATCC GGCAAACAAA CCACCGCTGG TAGCGGTGGT TTTTTTGTTT GCAAGCAGCA GATTACGCGC 18600
18601 AGAAAAAAAG GATCTCAAGA AGATCCTTTG ATCTTTTCTA CGGGGTCTGA CGCTCAGTGG AACGAAAACT CACGTTAAGG GATTTTGGTC ATGAGATTAT 18700
18701 CAAAAAGGAT CTTCACCTAG ATCCTTTTAA ATTAAAAATG AAGTTTTAAA TCAATCTAAA GTATATATGA GTAAACTTGG TCTGACAGTT ACCAATGCTT 18800
18801 AATCAGTGAG GCACCTATCT CAGCGATCTG TCTATTTCGT TCATCCATAG TTGCCTGACT CCCCGTCGTG TAGATAACTA CGATACGGGA GGGCTTACCA 18900
18901 TCTGGCCCCA GTGCTGCAAT GATACCGCGA GACCCACGCT CACCGGCTCC AGATTTATCA GCAATAAACC AGCCAGCCGG AAGGGCCGAG CGCAGAAGTG 19000
19001 GTCCTGCAAC TTTATCCGCC TCCATCCAGT CTATTAATTG TTGCCGGGAA GCTAGAGTAA GTAGTTCGCC AGTTAATAGT TTGCGCAACG TTGTTGCCAT 19100
19101 TGCTACAGGC ATCGTGGTGT CACGCTCGTC GTTTGGTATG GCTTCATTCA GCTCCGGTTC CCAACGATCA AGGCGAGTTA CATGATCCCC CATGTTGTGC 19200
19201 AAAAAAGCGG TTAGCTCCTT CGGTCCTCCG ATCGTTGTCA GAAGTAAGTT GGCCGCAGTG TTATCACTCA TGGTTATGGC AGCACTGCAT AATTCTCTTA 19300
19301 CTGTCATGCC ATCCGTAAGA TGCTTTTCTG TGACTGGTGA GTACTCAACC AAGTCATTCT GAGAATAGTG TATGCGGCGA CCGAGTTGCT CTTGCCCGGC 19400
19401 GTCAATACGG GATAATACCG CGCCACATAG CAGAACTTTA AAAGTGCTCA TCATTGGAAA ACGTTCTTCG GGGCGAAAAC TCTCAAGGAT CTTACCGCTG 19500
19501 TTGAGATCCA GTTCGATGTA ACCCAGCGTG GATCTTCAGC CTCTTCCTTT TTCAATATTA TTGAAGCATT TATCAGGGTT ATTGTCTCAT 19600
19601 ATGCCGCAAA AAAGGGAATA AGGGCGACAC GGAAATGTTG AATACTCATA CTCTTCCTTT TTCAATATTA TTGAAGCATT TATCAGGGTT ATTGTCTCAT 19700
19701 GAGCGGATAC ATATTTGAAT GTATTTAGAA AAATAAACAA ATAGGGGTTC CGCGCACATT TCCCCGAAAA GTGC                                        19774
                |          |          |          |          |          |          |          |          |          |
                10         20         30         40         50         60         70         80         90         100
```

FIG. 4b continuation

Figure 5a

HPV16-L1 gene

```
          10         20         30         40         50         60         70         80         90        100
           |          |          |          |          |          |          |          |          |          |
   1 ATGAGCCTGT GGCTGCCCAG CGAGGCCACC GTGTACCTGC CCCCCGTGCC CGTGAGCAAG GTGGTGAGCA CCGACGAGTA CGTGGCCAGG ACCAACATCT  100
 101 ACTACCACGC CGGCACCAGC AGGCTGCTGG CCGTGGGCCA CCCCTACTTC CCCATCAAGA AGCCCAACAA CAACAAGATC CTGGTGCCCA AGGTGAGCGG  200
 201 CCTGCAGTAC AGGGTGTTCA GGATCCACCT GCCCGACCCC AACAAGTTCG GCTTCCCCGA CACCAGCTTC TACAACCCCG ACACCCAGAG GCTGGTGTGG  300
 301 GCCTGGCTGG GCGTGGAGGT GGGCAGGGGC CAGCCCCTGG GCGTGGGCAT CAGCGGCCAT CCCCTGCTGA ACAAGCTGGA CGACACCGAG AACGCCAGCG  400
 401 CCTACGCCGC CAACGCCGGC GTGGACAACA GGGAGTGCAT CAGCATGGAC TACAAGCAGA CCCAGCTGTG CCTGATCGGC TGCAAGCCCC CCATCGGCGA  500
 501 GCACTGGGGC AAGGGCAGCC CCTGCACCAA CGTGGCCGTG AACCCCGGCG ACTGCCCCCC CCTGGAGCTG ATCAACACCG TGATCCAGGA CGGCGACATG  600
 601 GTGGACACCG GCTTCGGCGC CATGGACTTC ACCACCCTGC AGGCCAACAA GAGCGAGGTG CCCCTGGACA TCTGCACCAG CATCTGCAAG TACCCCGACT  700
 701 ACATCAAGAT GGTGAGCGAG CCCTACGGCG ACAGCCTGTT CTTCTACCTG AGGAGGGAGC AGATGTTCGT GAGGCACCTG TTCAACAGGG CCGGCGCCGT  800
 801 GGGCGAGAAC GTGCCCGACG ACCTGTACAT CAAGGGCAGC GGCAGCACCG CCAACCTGGC CAGCAGCAAC TACTTCCCCA CCCCCAGCGG CAGCATGGTG  900
 901 ACCAGCGACG CCCAGATCTT CAACAAGCCC TACTGGCTGC AGAGGGCCCA GGGCCACAAC AACGGCATCT GCTGGGGCAA CCAGCTGTTC GTGACCGTGG 1000
1001 TGGACACCAC CAGGAGCACC AACATGAGCC TGTGCGCCGC CATCAGCACC AGCGAGACCA CCTACAAGAA CACCAACTTC AAGGAGTACC TGAGGCACGG 1100
1101 CGAGGAGTAC GACCTGCAGT TCATCTTCCA GCTGTGCAAG ATCACCCTGA CCGCCGACGT GATGACCTAC ATCCACACCA TGAACCCCGC CATCCTGGAG 1200
1201 GACTGGAACT TCGGCCTGCA GCCCCCCCCC GGCGGCACCC TGGAGGACAC AGTTGACCGC GTGACCAGTT CTGACCATCGC CTGCCAGAAG CTGACCCCCC 1300
1301 CCGCCCCCAA GGAGGACCCC CTGAAGAAGT ACACCTTCTG GGAGGTGAAC CTGAAGGAGA AGTTCAGCGC CGACCTGGAC CAGTTCCCCC TGGGCAGGAA 1400
1401 GTTCCTGCTG CAGGCCGGCC TGAAGGCCAA GCCCAAGTTC ACCCTGGGCA AGAGAAGGC CACCCCCACC AGCACCAGCA CCAGCACCAC CGCCAAGAGG 1500
1501 AAGAAGAGGA AGCTGTGA                                                                                          1518

HPV16-L2 gene

```
        10         20         30         40         50         60         70         80         90        100
         |          |          |          |          |          |          |          |          |          |
   1  atgcgacaca aacgttctgc aaaacgcaca aaacgtgcat cggctaccca actttataaa acatgcaaac aggcaggtac atgtccacct gacattatac  100
 101  ctaaggttga agcaaaact  attgctgaac aaatattaca atatggaagt atgggtgtat tttttggttg gttaggaatt ggaacagggt cgggtacagg  200
 201  cggacgcact gggtatattc cattgggaac aaggcctccc acagctacag atacacttgc tcctgtaaga cccctttaa  cagtagatcc tgtgggccct  300
 301  tctgatcctt ctatagtttc tttagtggaa gaaactagtt ttattgatgc tggtgcacca acatctgtac cttccattcc cccagatgta tcaggattta  400
 401  gtattactac ttcaactgat accacacctg ctatattaga tattaataat actgttacta ctgttactac acataataat cccactttca ctgacccatc  500
 501  tgtattgcag cctccaacac ctgcagaaac tggaggcat  tttacacttt catcatccac tattagtaca cataattatg aagaaattcc tatggataca  600
 601  tttattgtta gcacaaaccc tacacagta  actagtagca ccactcccac agggtctcgc ccagtggcac gcctaggatt atatagtcgc acaacacaac  700
 701  aggttaaagt tgtagccct  gcttttgtaa ccactccac  acatatgata atcctgcata tgaaggtata gatgtggata taacattata  800
 801  tttttctagt aatgataata gtattaatat agtccagat  agctccagat tgcttttacat aggcagcat  taacctctag gcgtactggc  900
 901  attaggtaca gtagaattgg taataaacaa acactacgta ctcgtagtgg aaaatcata  ggtgctaagg tacattatta ttatgattta agtactattg  1000
1001  atccctgcaga agaaatagaa ttacaaacta acaccctc  tacatatact accactcac  atgcagcctc acctacttct attaataatg gattatatga  1100
1101  tatttatgca gatgactta  ttacagatac ttctacaacc ccggtaccat ctgtaccctc tacatcttta tcaggtata tcctgcaaa  tacaacaatt  1200
1201  cctttttgtg gtgcatacaa tattccttta gtatcaggtc ctgatatacc actgaccaag ctccttcatt aattcctata gttccaggt  1300
1301  ctccacaata tacaattatt gctgatgcag gtgacttta tttacatcct cattaataca tgttacgaaa acgacgaaa  acgtaa      cgtttaccat attttttc    1400
1401  agatgtctct ttgctgcct   ag                                                                                   1422
```

HPV16-E6 gene

```
        10         20         30         40         50         60         70         80         90        100
         |          |          |          |          |          |          |          |          |          |
  1 atgcaccaaa agagaactgc aatgtttcag gacccacagg agcgacccag aaagttacca cagttatgca cagagctgca aacaactata catgatataa  100
101 tattagaatg tgtgtactgc aagcaacagt tactgcgacg tgaggtatat gactttgctt ttcgggattt atgcatagta tatagagatg ggaatccata  200
201 tgctgtatgt gataaatgtt taaagtttta ttctaaaatt agtgagtata gacattattg tatgaacaa cattagaaca gcaatacaac  300
301 aaaccgttgt gtgatttgtt gcattaggtgt attaactgtc aaaagccact gtgtcctgaa gaaaagcaaa gacatctgga caaaaagcaa agattccata  400
401 atataagggg tcggtggacc ggtcgatgta tgtcttgttg cagatcatca agaacacgta gagaaaccca gctgtaa                            477
         |          |          |          |          |          |          |          |          |          |
        10         20         30         40         50         60         70         80         90        100
```

Figure 5d

HPV16-E7 gene

```
         |    10       |    20       |    30       |    40       |    50       |    60       |    70       |    80       |    90       |   100
  1 atgcatggag atacacctac attgcatgaa tatatgttag atttgcaaac agagacaact gatcctctact gttatgagca attaaatgac agctcagagg 100
101 aggaggatga aatagatggt ccagctggac aagcagaacc ggacagagcc cattacaata ttgtaacctt ttgttgcaag tgtgactcta cgcttcggtt 200
201 gtgcgtacaa agcacacacg tagacattcg tactttggaa gacctgttaa tgggcacact aggaattgtg tgccccatct gttctcagaa accataa 297
         |    10       |    20       |    30       |    40       |    50       |    60       |    70       |    80       |    90       |   100
```

Figure 5e

HPV18-L1 gene

```
           |       10 |       20 |       30 |       40 |       50 |       60 |       70 |       80 |       90 |      100
    1 ATGTGCCTGT ATACACGGGT CCTGATATTA CATTACCATC TACTACCTCT GTATGGCCCA TTGTATCACC CACGGCCCCT GCCTCTACAC AGTATATTGG  100
  101 TATACATGGT ACACATTATT ATTTGTGGCC ATTATATTAT TTTATTCCTA AGAAACGTAA ACGTGTTCCC TATTTTTTG CAGATGGCTT TGTGGCGGCC  200
  201 TAGTGACAAT ACCGTATATC TTCCACCTCC TTCTGTGGCA AGAGTTGTAA ATACCGATGA TTATGTGACT CCCACAAGCA TATTTTATCA TGCTGGCAGC  300
  301 TCTAGATTAT TAATCCATAT TTTAGGGTTC TGGCAGGTGG CTGCAGGTGG ATTTATAAATC CTGAAACACA ACGTTTAGTG TGGGCCTGTG TATAGAGTAT  400
  401 TTAGGGTGCA GTTACCTGAC GGTCAGCCTT TAGGTGTTGG CCTTAGTGGG CATCCATTTT ATAATAAATT CTGAAACACA GAAAGTTCCC TGGCCTGTG TATAGAGTAT  500
  501 AATTGGCCGT TAGGGACAA TGTGTCTGTA GATTATAAGC AGACACAGTT ATGTATTTTG GGCTGTGCCC GAAAGTTCCC ATGCCGCCAC GTCTAATGTT  600
  601 TCTGCTTGTA ATCGCGTCCT TTATCACAGG GCGATTGCCC CCCTTTAGAA CTTAAAACAC CAGTTTTGGA GGAACACTGG GCTAAAGGCA  700
  701 CTGCCATGGAC TTTAGTACAT TGCAAGATAC TAACGGCGTG GTACCATTGG ATATTTGTCA GTCTATTTGT AGATGGTGAT ATGGTAGATA CTGGATATGG  800
  801 TGCCATGGAC TTTAGTACAT TGCAAGATAC TAACGGCGTG GTACCATTGG AGCAGCTTTT TGCTAGGCAT GTCTATTTGT AGATGGTGAT ATGGTAGATA CTGGATATGG  900
  901 GATCCTTATG GGGATTCCAT GTTTTTTTGC ACAGTATGC CTGCTTCACC TGGCAGCTGT GTGTATTCTC CCTCTCCAAG GAGCAGGTAC TATGGGTGAC ACTGTCTC  1000
 1001 AATCCTTATA TATTAAAGGC CCATATTGGT ACAGGGTCAT AACAATGGTG TTTGCTGGCA TAATCAATTA TTTGTTACTG CACTCCCAGT  1100
 1101 GTTTAATAAA CCATATTGGT TACATATGTGC ACAGGGTCAT AACAATGGTG TCTCCTGTAC CTGGGCAATA TGATGCTACC AAATTAAGC AGTATAGCAG ACATGTTGAG GAATATGATT  1200
 1201 ACCAATTTAA CAATATGTGC TTCTCAGTTG TGTACTATTA CTTTAACTGC AGATGTTATG TCCTATATTC ATAGTATGAA TAGCAGTATT TTAGAGGATT GGAACTTTGG  1300
 1301 TGCAGTTTAT TTTTCAGTTG CCCCAACTA GTTTTGGT GGATACATAT CGTTTTGTAC AATCTGTTGC TATTACCTGT CAAAAGGATG CTGCACCGGC TGAAAATAAG  1400
 1401 TGTTCCCCCC CCCCAACTA GTTTTGGAAT GTGGATTTAA AGGAAAAGTT TCTTCTCTAC AATCTGTTGC TATTACCTGT CAAAAGGATG CTGCACCGGC TGAAAATAAG  1500
 1501 GATCCCTATG ATAAGTTAAA GTTTTGGAAT GTGGATTTAA AGGAAAAAGTT TCTTTTAGAC TTAGATCAAT ATCCCCTTGG ACGTAAATTT TTGGTTCAGG  1600
 1601 CTGGATTGCG TCGCAAGCCC ACCATAGGCC CTCGCAAACG TTCTGCTCCA TCTGCCACTA CGTCTTCTAA ACCTGCCAAG CGTGTGCGTG TACGTGCCAG  1700
 1701 GAAGTAA                                                                                                      1707
```

Figure 5f

HPV18-L2 gene

```
          10         20         30         40         50         60         70         80         90        100
   1 ATGGTATCCC ACCGTGCCGC ACGACGCAAA CGGGCTTCGG TAACTGACTT ATATAAAACA TGTAAACAAT CTGGTACATG TCCACCTGAT GTTGTTCCTA  100
 101 AGTGGAGGG CACCACGTTA GCAGATAAAA TATTGCAATG GTCAAGCCTT GGTATATTTT TGGGTGGACT TGGCATAGGT ACTGGCAGTG GTACAGGGGG  200
 201 TCGTACAGGG TACATTCCAT TGGGTGGCCG TTCCAATACA GTGGTGGATG ACGTCCCCCA ACGTTTACTG GTGTTATTG AACCTGTGGG CCCCACAGAC  300
 301 CCATCTATTG TTACATTAAT AGAGGACTCC AGTGTGGTTA CATCAGGTGC ACCTAGGCCT ACGTTTACTG GCACGTCTGG GTTTGATATA ACATCTGCGG  400
 401 GTACAACTAC ACCTGCGGTT TTGGATATCA CACCTTCGTC CACCTCTGTG TCTATTTCCA CAACCAATTT TACCAATCCT GCATTTTCTG ATCCGTCCAT  500
 501 TATTGAAGTT CCACAAACTG GGAGGTGGC AGTAATGTA TTTGTTGGTA CCCCTACATC TGGAACACAT GGGTATGAGG AAATACCTTT ACAAACATTT  600
 601 GCTTCTTCTG GTACGGGGGA GGAACCCATT AGTAGTACCC CATTGCCTAC TGTGCGGCGT GTAGCAGGTC CCGCCTTTA GCTGTGGAC TACTAGGGCC TACCAACAAG  700
 701 TGTAGTGGC TAACCCTGAG TTTCTTACAG CATTGCCTC TTTAATTACA CGGCCTGCT TATGACAACC CGGCCTTTGA GCCTGTGGAC TTCGCTTTAG CATTGATCC  800
 801 TCGTAGTGAT GTTCCTGATI CAGATTTTAT GGATATTAT CGTCTACATA GGCCTGCTTT AACATCCAGG CGTGGGACTG GTCCTATTGC ACCTTCCCCA GAATATATTG 1000
 901 CAACGGGCAA CTATGTTTAC CCGCAGCGGT ACACAAATAG GTGCTAGGGT TCACTTTTAT CATGATATAA GTCCTATTGC ACCTTCCCCA GAATATATTG 1000
1001 AACTGCAGCC TTTAGTATCT GCCACGGAGG ACAATGACTT GTTTGATATA TATGCAGATG ACATGGGACCC TGCAGTGCCT GTACATCGC GTTCTACTAC 1100
1101 CTCCTTTGCA TTTTTAAAT ATTCGCCCAC TATATCTTCT GCCTCTTCCT AAGTAATGT AACGGTCCCT TTAACCTCCT CTTGGGATGT GCCTGTATAC 1200
1201 ACGGGTCCTG ATATTACATT ACCATCTACT ACCTCTGTAT GGCCCATTGT ATCACCCACG GCCCCTGCCT CTACACAGTA TATTGGTATA CATGGTACAC 1300
1301 ATTATTATT GTGGCCATTA TATTATTTA TTCCTAAGAA ACGTAAACGT GTTCCCTATT TTTTTGCAGA TGGCTTTGTG GCGGCCTAG                1389
          10         20         30         40         50         60         70         80         90        100
```

Figure 5g

HPV18-E6 gene

```
          10         20         30         40         50         60         70         80         90        100
          |          |          |          |          |          |          |          |          |          |
  1 ATGGCGCGCT TTGAGGATCC AACACGGCGA CCCTACAAGC TACCTGATCT GTGCACGGAA CTGAACACTT CACTGCAAGA CATAGAAATA ACCTGTGTAT 100
101 ATTGCAAGAC AGTATTGGAA CTTACAGAGG TATTTGAATT TGCATTTAAA GATTATTTTG TGGTGTATAG AGACAGTATA CCCCATGCTG CATGCCATAA 200
201 ATGTATAGAT TTTTATTCTA GAATTAGAGA ATTAAGACAT TATTCAGACT CTGTGTATGG AGACACATTG GAAAAACTAA CTAACACTGG GTTATACAAT 300
301 TTATTAATAA GGTGCCTGCG GTGCCAGAAA CCGTTGAATC CAGCAGAAAA ACTTAATGAAA AACGACGATT TCACAACATA GCTGGGCACT 400
401 ATAGAGGCCA GTGCCATTCG TCCTGCAACC GAGCACGACA GGAACGACTC CAACGACGCA GAGAAACACA AGTATAA 477
          |          |          |          |          |          |          |          |
          10         20         30         40         50         60         70         80         90        100
```

Figure 5h

HPV18-E7 gene

```
         10         20         30         40         50         60         70         80         90        100
          |          |          |          |          |          |          |          |          |          |
  1 ATGCATGGAC CTAAGGCAAC ATTGCAAGAC ATTGTATTGC ATTTAGAGCC CCAAAATGAA ATTCCGGTTG ACCTTCTATG TCACGAGCAA TTAAGCGACT 100
101 CAGAGGAAGA AAACGATGAA ATAGATGGAG TTAATCATCA ACATTTACCA GCCCGACGAG CCGAACCACA AGTTGTGTA ATGTTGTGTA TGTGTTGTAA 200
201 GTGTGAAGCC AGAATTGAGC TAGTAGTAGA AAGCTCAGCA GACGACCTTC GAGCATTCCA GCAGCTGTTT CTGAACACCC TGTCCTTTGT GTGTCCGTGG 300
301 TGTGCATCCC AGCAGTAA                                                                                        318
          |          |          |          |          |          |          |          |          |
         10         20         30         40         50         60         70         80         90        100
```

Figure 5i

HPV6-L1 gene

|  | 10 | 20 | 30 | 40 | 50 | 60 | 70 | 80 | 90 | 100 |
|---|---|---|---|---|---|---|---|---|---|---|
| 1 | ATGTGGCGGC | CTAGCGACAG | CACAGTATAT | GTGCCTCCTC | CTAACCCTGT | ATCCAAAGTT | GTTGCCACGG | ATGCTTATGT | TACTCGCACC | AACATATTTT | 100
| 101 | ATCATGCCAG | CAGTTCTAGA | CTTCTTGCAG | TGGGTCATCC | TTATTTTTCC | ATAAAACGGG | CTAACAAAAC | TGTTGTGCCA | AAGGTGTCAG | GATATCAATA | 200
| 201 | CAGGGTATTT | AAGTGGTGT | TACCAGATCC | TAACAAATTT | GCATTGCCTG | ACTCGTCTCT | TTTTGATCCC | ACAACACAAC | GTTTGGTATG | GGCATGCACA | 300
| 301 | GCCCTAGAGG | TGGCCAGGGG | ACAGCCATTA | GGTGTGGGTG | TAAGTGGACA | TCCTTTCCTA | AATAAATATG | ATGATGTTGA | AAATTCAGGG | AGTGGTGGTA | 400
| 401 | ACCCTGGACA | GGATAACAGG | GTTAATGTTG | GTATGGATTA | TAAACAAACA | CAATTATGCA | TGGTTGGATG | TGCCCCCCCT | TTGGGCGAGC | ATTGGGGTAA | 500
| 501 | AGGTAAACAG | TGTACTAATA | CACCTGTACA | GGCTGGTGAC | TGCCCGCCCT | TAGAACTTAT | TACCAGTGTT | ATACAGGATG | GCGATATGGT | TGACACAGGC | 600
| 601 | TTTGGTGCTA | TGATTTTGC | TGATTTGCAG | ACCAATGTCC | CAGATGTTCC | TATTTACATA | TGTGGCACTA | CATGTAAATA | TCCAGATTAT | TTACAAATGG | 700
| 701 | CTGCAGACCC | ATATGGTGAT | AGATTATTTT | TTTTTCTACG | GAAGGAACAA | ATGTTTGCCA | GACATTTTTT | TAACAGGGCT | GGGAGGTGG | GGGAACCTGT | 800
| 801 | GCCTGATACT | CTTATAATTA | AGGGTAGTGG | AAATCGAACG | TCTGTAGGGA | GTAGTATATA | TGTTAACACC | CCAAGCGGCT | CTTTGGTGTC | CTCTGAGGCA | 900
| 901 | CAATTGTTTA | ATAAGCCATA | TTGGCTACAA | AAAGCCCAGG | GACATAACAA | TGGGTAATTC | TGGGTAATC | AACTGTTTGT | TACTGTGGTA | GATACCACAC | 1000
| 1001 | GCAGTACCAA | CATGACATTA | TGTGCATCCG | TAACTACATC | TTCCAACACAG | ACCAATTCA | ATTATAAAGA | GTACATGCGT | CATGTGAAG | GAACTTTGG | 1100
| 1101 | ACAATTTATT | TTTCAATTAT | GTAGCATTAT | ATTGTCTGCT | GAAGTAATGG | CCTATATTCA | CACAATGTG | CCCTCTGTTT | TGGAAGACTG | AGTATGATTT | 1200
| 1201 | TTATCGCCTC | CCCCAAATGG | TACATTAGAA | GATACCTATA | GGTATGTGCA | GTCACAGGCC | ATTACCTGTC | AAAAGCCCAC | TCCTTTGGGA | GAAAAGCCAG | 1300
| 1301 | ATCCCTATAA | GAACTTAGT | TTTTGGGAGG | TTAATTTAAA | AGAAAAGTTT | TCTAGTGAAT | TGGATCAGTA | TCCTTTGGGA | CGCAAGTTTT | TGTTACAAAG | 1400
| 1401 | TGGATATAGG | GGACGTCCT | CTATTCGTAC | CGGTGTTAAG | CGCCCTGCTG | TTTCCAAAGC | CTCTGCTGCC | CCTAAACGTA | AGCGGCCCAA | AACCAAAAGG | 1500
| 1501 | TAA |  |  |  |  |  |  |  |  |  | 1503

|  | 10 | 20 | 30 | 40 | 50 | 60 | 70 | 80 | 90 | 100 |

Figure 5j

HPV6-L2 gene

```
          10         20         30         40         50         60         70         80         90        100
          |          |          |          |          |          |          |          |          |          |
   1 ATGGCACATA GTAGGGCCCG ACGACGCAAG CGTGCGTCAG CTACACAGCT ATATCAAACA TGTAAACTCA CTGGAACATG CCCCCCAGAT GTAATTCCTA  100
 101 AGGTGGAACA CAACACCATT GCAGATCAAA TATTAAAATG GGGGAGTTTG GGGTGTTTT TTGGAGGGTT GGGTATAGGC ACCGGTTCCG GCACTGGGGG  200
 201 TCGTACTGGC TATGTTCCCT TAGGAACTTC TGCAAAACCT TCTATTACTA GTGGGCCTAT GGCTCGTCCT CCTGTGGTGG GGAGCCTGT GGCCCCTTCG  300
 301 GATCCATCCA TTGTGTCTTT AATTGAAGAA TCGGCAATCA TTAACGCAGG GGCGCCTGAA ATTGTGCCCC CTGCACACGG TCCTGTCTT ACAGAACCTT ATTACATCCT  400
 401 CTGAAACAAC TACCCCTGCA ATATTGGATG TATCAGTTAC TAGTCATACT ACTACTAGTA TATTTAGAAA TCCTGTCTT GAGGAAATTC TATATAGTCG CTGTAACACA  500
 501 ACCCCAACCA CCCGTGGAGG CTAATGGACA TATATTTGGC TCTTGCACCCA CTATAACGTC ACACCCTATA CGTGTGGGCC CTTTAGATAC TTTTGTGATA  600
 601 TCCTCTAGTG ATAGCGGTCC TCATTCCAGT ACCCCTGTTC CTGGTACTGC ACCTCGGCCT CGTGTGGGCC TGCATTGCAC CAGGTGCAGG  700
 701 TTACAGACCC TGCATTTCTT TCCACTCCTC AACGCTTAAT TACATATGAT AACCCTGTAT ATGAAGGGGA TGCGTCCCGA CGTGGCCTTG GTACAATTA GTCATGATTC  800
 801 TATACACAAT GCACCTGATG AGGCTTTTAT GGACATAATT CGTTTGCACA GACCTGCTAT TGCGTCCCGA CGTGGCCTTG ACAAGCTGCA TCGCATTGGA  900
 901 CAACGGGGGT CTATGCACAC TCGCAGCGGA AAGCACATAG GGGCCCGCAT TCATTATTTT TATGATATTT CACCTATTGC ACAAGCTGCA GAAGAAATAG 1000
1001 AAATGCACCC TCTTGTGGCT GCACAGGAAG ATACATTTGA TATTTATGCT GAATCTTTTG AACCTGACAT TAACCCTACC TTACAAATAT 1100
1101 ATCAGATACA TATTTAACTT CCAACACCAC TACAGTTACA CAACCTGGG GTAACACCAC AGTTCCATTG TCAATTCCTA ATGACCTGTT TTTACAGTCT 1200
1201 GGCCCTGATA TAACTTTTCC TACTGCACCT ATGGGAACAC CCTTTAGTCC TGTAACTCCT GCTTTACTA CAGGCCCTGT TTTCATTACA GGTTCTGGAT 1300
1301 TTTATTTGCA TCCTGCATGG TATTTGCGCA GAAACGCCCG TAAACGTATT CCCTTATTTT TTTCAGATGT GGCGGCCTAG                       1380
          |          |          |          |          |          |          |          |          |          |
          10         20         30         40         50         60         70         80         90        100
```

Figure 5k

HPV6-E6 gene

```
         10         20         30         40         50         60         70         80         90        100
         |          |          |          |          |          |          |          |          |          |
  1 ATGGAAAGTG CAAATGCCTC CACGTCTGCA ACGACCATAG ACCAGTTGTG CAAGACGTTT AATCTATCTA TGCATACGTT GCAAATTAAT TGTGTGTTTT 100
101 GCAAGAATGC ACTGACCACT GCAGAGATTT ATTCATATGC ATATAAACAG CTAAAGGTCC TGTTTCGAGG CGGCTATCCA TATGCAGCCT GCGCGTGCTG 200
201 CCTAGAATTT CATGGAAAAA TTAACCAATA TAGACACTTT GATTATGCTG GATATGCAAC AACTGTTGAA GAAGAAACTA AACAAGACAT TTTAGACGTG 300
301 CTAATTCGGT GCTACCTGTG TCACAAACCG CTGTGTGAAG TAGAAAAGGT AAAACATATA CTAACCAAGG CACGGTTCAT AAAGCTAAAT TGTACGTGGA 400
401 AGGGTCGCTG CCTACACTGC TGGACAACAT GCATGGAAGA CATGTTACCC TAA                                                  453
         |          |          |          |          |          |          |          |          |          |
         10         20         30         40         50         60         70         80         90        100
```

Figure 5l

HPV6-E7 gene

```
       10         20         30         40         50         60         70         80         90        100
        |          |          |          |          |          |          |          |          |          |
  1 ATGCATGGAA GACATGTTAC CCTAAAGGAT ATTGTATTAG ACCTGCAACC TCCAGACCCT GTAGGGTTAC ATTGCTATGA GCAATTAGTA GACAGCTCAG 100
101 AAGATGAGGT GGACGAAGTG GACGGACAAG ATTCACACAA TTTAAAACAA CATTACCAAA TAGTGACCTG TTGCTGTGGA TGTGACAGCA ACGTTCGACT 200
201 GGTTGTGCAG TGTACAGAAA CAGACATCAG AGAAGTGCAA CAGCTTCTGT TGGGAACACT AAACATAGTG TGTCCCATCT GCGCACCGAA GACATAA    297
        |          |          |          |          |          |          |          |          |          |
       10         20         30         40         50         60         70         80         90        100
```

| 1.00E+05 |
| 1.00E+04 |
| 1.00E+03 |
| 1.00E+02 |
| 1.00E+01 |
| 1.00E+00 |

1  2  3  4  5  6

△ MV2EZ-HPV-L1 Bern    ○ MVEZ

CF

| 1.00E+05 |
| 1.00E+04 |
| 1.00E+03 |
| 1.00E+02 |
| 1.00E+01 |
| 1.00E+00 |

1  2  3  4  5  6

△ MV2EZ-HPV-L1 Bern    ○ MVEZ

Figure 9
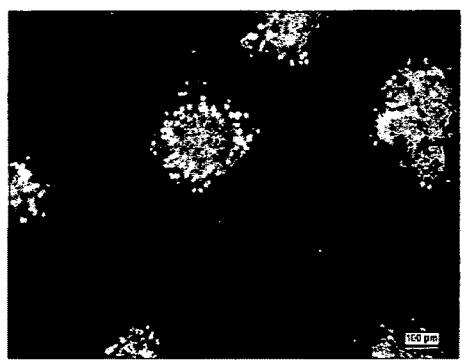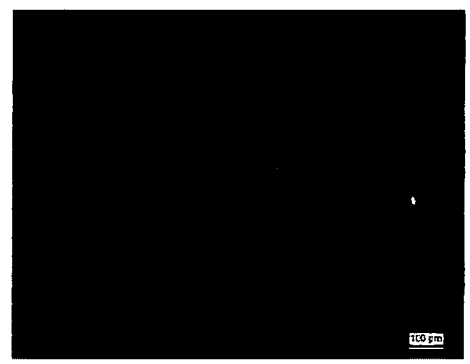

A. MV2EZ-HPV-L1    B. MVEZ
Anti-L1 antiserum
DAPI

COMBINED MEASLES-HUMAN PAPILLOMA VACCINE

TECHNICAL FIELD OF THE INVENTION

The present invention relates to combined vaccines against measles and human papilloma virus (HPV). In particular, the invention relates to recombinant measles virus vectors containing heterologous nucleic acid encoding single or several antigens derived from HPV, preferably, the major capsid antigen L1, the minor capsid antigen L2, the early gene E6 and the early gene E7 oncoproteins of HPV type 16, and optionally of types 18, 6 and 11.

In a first embodiment, prophylactic vaccines are generated expressing HPV antigens, preferably L1 and/or L2 such that they induce a potent long-lasting immune response in mammals, preferably humans, to protect against HPV and MV infection. In another embodiment, therapeutic vaccines are generated expressing E6 and E7 proteins, and optionally L1 and L2, such that they induced strong immune responses will resolve persistent HPV infections at early or late stages, including HPV-induced cervical carcinoma. In a preferred embodiment, the combined vaccines are easy to produce on a large scale and can be distributed at low cost.

BACKGROUND OF THE INVENTION

Syndromes Induced by Human Papilloma Virus

Every year approximately half a million new cervical cancer cases are registered worldwide, particularly in developing countries, representing the second most common cause of mortality in women. Human Papillomaviruses (HPVs) are the primary etiologic agent of cervical carcinoma; HPV DNA can be found in more than 95% of these cancers (1). Since 1998, prevention and treatment strategy mainly rely on structured screening programs to detect and ablate pre-invasive disease. However, use of HPV testing is limited by social issues and currently the main obstacle is its high cost. Thus the development of vaccines that prevent HPV infection represent an important opportunity to prevent cervical cancer whilst a therapeutic immunization would be valuable in treating pre-malignant and malignant disease.

HPVs belong to a large family of small double-stranded DNA viruses that infect squamous epithelia. (For a recent comprehensive review on papillomaviruses see Howley, P M and Lowy, D R (2007) in: Fields Virology, fifth edition), eds.-in-chief Knipe, D. M. &. Howley, P. M. Lippincott Williams & Wilkins, Philadelphia Pa. 19106, USA, pp. 2299-2354 To date, more than 100 genotypes have been described, among which at least 35 types infect the genital tract. Although most of the HPV types produce benign lesions, a small subset of genotypes is strongly associated with the development of high-grade squamous intraepithelial lesions and cervical cancer. This subset has been identified as "high risk" and it is estimated that HPV-16 accounts for approximately 60% of cervical cancers, with HPV-18 adding another 10%-20%. Other high-risk types include types 31, 33, 35, 39, 45, 51, 52, 56, 58, 59, 68, and 73. Low-risk HPVs, such as HPV-6 and HPV-11, cause benign genital warts (90% begnin condylomata accuminata are HPV6 or 11 positive). Bivalent vaccines 16/18 eliminating the most common high-risk types may permit to overcome also the low-risk types. An ideal vaccine would protect against other HPV types through use of antigens from different types and/or antigens containing conserved regions.

The HPV genome encodes eight proteins. The late L1 and L2 genes code for capsid proteins; the early proteins E1 and E2 are responsible for viral replication and transcription, and E4 is involved in virus release from infected cells. The integration of high risk type HPV viral DNA into host genome results in a loss of E1 or E2 mediated transcriptional control and consequently in an over-expression of the E6 and E7 proteins responsible of the malignant transformation process (2). Structural protein L1 from high risk types represents an optimal target for prophylactic vaccines. On the other hand, E6 and E7 proteins are obvious therapeutic targets.

There are actually several prophylactic HPV vaccine formulations based upon the major viral capsid protein L1, either as a monomer, or as a virus like particle (VLP) from HPV 16 and 18 types and in some cases additional types (WO94/00152, WO94/20137, WO93/02184 and WO94/05792). VLPs may additionally comprise L2 proteins, for example, L2 based vaccines described in WO93/00436. These vaccines are highly immunogenic and appear safe; however their high cost does not permit generalized access to populations at risk and their HPV type specificity represents another limitation. Therefore, a remaining need exists to develop additional improved vaccines against HPV which should be inexpensive. Moreover vaccinations with antigen mainly induce an antibody specific response that is of little or no benefit on established HPV infection and related-disease.

The development of therapeutic vaccine relies not only on production of neutralising antibodies, but principally on the induction of specific cellular immune responses, that are key components for clearance of established infection. Thus, therapeutic vaccines are required to include some antigenic determinants derived from early HPV proteins rather than the late proteins. The early genes of the high-risk HPV types (E6 and E7) encode the main transforming proteins. These genes are capable of immortalization of epithelial cells and are thought to play a role in the initiation of the oncogenic process. The protein products of these early genes interfere with the normal function of tumour suppressor genes. HPV E6 is able to interact with p53, leading to its dysfunction, thereby impairing its ability to block the cell cycle when DNA errors occur. E6 also keeps the telomerase length above its critical point, protecting the cell from apoptosis. HPV E7 binds to retinoblastoma protein (pRb) and activates genes that start the cell cycle, leading to tissue proliferation. E6 and E7 proteins represent good targets and various approaches of HPV therapeutic vaccines have been described based on E6. In the last few years a number of peptide/protein-based or genetic immunization strategies have been described for the induction of HPV specific CTL activity. For a review of progress in the development of vaccines against HPV see ref (3). Attempts were made with DNA vaccines (plasmid DNA encoding HPV proteins) known to promote primarily a cellular response. Despite the fact that DNA vaccines work well in mouse models, numerous clinical trials have failed to provide proof of principle in man. Major drawbacks associated with a peptide-based approach include the problem of MHC-polymorphism and the risk of inducing T cell tolerance rather than T cell activation. Due to the induction of specific T cell tolerance, vaccination with a tumour-specific peptide has been shown to result in an enhanced outgrowth of the tumour. Immunization with larger proteins would overcome these problems, but this requires an efficient in vivo expression system and/or safe adjuvants for priming an efficient cellular immune response. Approaches involving recombinant viral vector vaccines are under development (Poxvirus, Adenovirus, Alphavirus, Poliovirus e Herpes Virus). Adenovirus based vaccine is described, for example, in US2007269409 (WO2004044176) which encodes the E6 or E7 protein of HPV. The adenovirus based vaccine is able to generate long term immunity; however, integration of HPV DNA into the host genome remains possible and may represent a safety limitation. In view of the above shortcomings the use of measles virus as a vector to express HPV antigens represents an original strategy to develop a prophylactic combined HPV-measles vaccine as well as a therapeutic HPV vaccine.

Immunisation Vectors Based on Measles Virus

Measles virus (MV) is a member of the family Paramyxoviridae. The non segmented genome of MV has an antimessage polarity which results in a genomic RNA which, when purified, is not translated either in vivo or in vitro and is not infectious. Transcription and replication of non-segmented (−) strand RNA viruses and their assembly as virus particles have been studied and reported (4). Transcription and replication of measles virus do not involve the nucleus of the infected cells but rather take place in the cytoplasm of said infected cells. The genome of the measles virus comprises genes encoding six major structural proteins from the six genes (designated N, P, M, F, H and L) and additional two-non structural proteins from the P gene. MV is a major cause of acute febrile illness in infants and young children. According to estimates of the World Health Organisation (WHO), one million young children die every year from measles. This high toll arises primarily in developing countries, but in recent years also industrialised countries such as the USA have been affected again by measles epidemics, primarily due to incomplete adherence to immunisation programs (5). At present, several live attenuated MV vaccine strains are in use (including the Schwarz, Moraten and Edmonston-Zagreb strains), almost all derived from the original Edmonston strain (6) by multiple passage in non human cells. MV vaccine is proven to be one of the safest, most stable, and effective human vaccines developed so far. Produced on a large scale in many countries and distributed at low cost through the Extended Program on Immunization (EPI) of WHO, this vaccine induces life-long immunity after a single injection (4, 7) and boosting is effective. Protection is mediated both by antibodies and by CD4 and CD8 T cells. Persistence of antibodies and CD8 cells has been shown for as long as 25 years after vaccination (7).

Martin Billeter and colleagues established an original and efficient reverse genetics procedure to generate non-segmented negative-strand RNA viruses from cloned deoxyribonucleic acid (cDNA) derived from Edmonston strain MV, as described in 8 and WO 97/06270, a scheme of the organization of the antigenomic p(+)MVEZ of measles virus is represented in FIG. 1. In the first place, these technologies allowed site directed mutagenesis enabling important insights in a variety of aspects of the biology of these viruses. Concomitantly, foreign coding sequences were inserted a) to allow localization of virus replication in vivo through marker gene expression, b) to develop candidate multivalent vaccines against measles and other pathogens, and c) to create candidate oncolytic viruses. The vector use of these viruses was experimentally encouraged by the pronounced genetic stability of the recombinants unexpected for RNA viruses, and by the high load of insertable genetic material, in excess of 6 kb. The known assets, such as the small genome size of the vector in comparison to DNA viruses, the extensive clinical experience of attenuated MV as vaccine with a proven record of high safety and efficacy, and the low production cost per vaccination dose are thus favourably complemented.

The recombinant measles virus nucleotide sequence must comprise a replicon having a total number of nucleotides which is a mutiple of six. The <<rule of six>> is expressed in the fact that the total number of nucleotides present in the recombinant cDNA finally amount to a total number of nucleotides which is a multiple of six, a rule which allows efficient replication of genome RNA of the measles virus.

The heterologous DNA is cloned in the MV vector within an Additional Transcription Unit (ATU) inserted in the cDNA corresponding to the antigenomic RNA of measles virus. The location of the ATU can vary along said cDNA: it is however located in such a site that it will benefit from the expression gradient of the measles virus. Therefore, the ATU or any insertion site suitable for cloning of the heterologous DNA sequence can be spread along the cDNA, with a preferred embodiment for an insertion site and especially in an ATU, present in the N-terminal portion of the sequence and especially within the region upstream from the L-gene of the measles virus and advantageously upstream from the M gene of said virus and more preferably upstream from the N gene of said virus.

The advantageous immunological properties of the recombinant measles viruses can be shown in an animal model which is chosen among animals susceptible to measles viruses, and wherein the humoral and/or cellular immune response against the heterologous antigen and/or against the measles virus is determined. Among such animals suitable to be used as model for the characterization of the immune response, the skilled person can especially use transgenic mice expressing CD46 specific receptor for MV, or in monkeys.

The technology permits to produce rescued viruses containing and stably expressing foreign genes suitable for use as combined MV vaccines. As a proof of concept, MV has been used to express antigens derived from SIV, HIV, hepatitis B, mumps, West Nile (WN) Virus and SARSCoV (9-12). In most of these studies, recombinant MVs that express heterologous antigens appeared to induce specific humoral neutralizing antibodies in a transgenic mouse model (13) and were shown to induce cellular immune responses to some proteins (9, 11). At the present, clinical trials with any recombinant vaccine candidate based on MV are only in the planning stage however experimental results support the hypothesis that MV combined vaccines should be as efficient in eliciting long-lasting immune protection against other pathogenic agents as against the vector virus itself. In fact, in the case of MV expressing WNV gpE, a complete protection up to six months has been documented in monkeys (14), and MV expressing a Dengue antigen induced long term production of neutralizing antibodies (15). Moreover, in transgenic mice and macaques, rescued recombinant MV was capable of inducing specific antibody responses to heterologous antigen in the presence of pre-existing immunity against MV (9, 11, 16).

Rescued live recombinant MV vaccines are easily produced on a large scale in most countries and can be distributed at low cost. Regarding safety, MV replicates exclusively in the cytoplasm, ruling out the possibility of integration into host DNA. These characteristics make rescued recombinant MV vaccine an attractive candidate to be used as a multivalent vaccination vector for HPV antigens. Adult populations, even already MV immunized individuals, may however also benefit from MV recombinant immunization because re-administering MV virus under the recombinant form of the present invention may result in a boost of anti-MV antibodies (11)

So far, no approach has been developed to produce a vaccine able to induce immunity against MV combined with immunity against HPV.

The invention relates in particular to the preparation of recombinant measles viruses, bearing heterologous nucleic acid encoding antigens from HPV.

DETAILED DESCRIPTION OF THE INVENTION

The object of the invention is the production of combined measles-HPV vaccines from a recombinant Measles vector capable of containing stably integrated nucleotide sequences which code for L1, L2, E6 and/or E7 protein from different HPV types.

The invention includes the rescue of recombinant MV-HPV viruses which are capable of infection, replication and expression of L1, L2, E6 or E7 protein in susceptible transgenic mice, monkeys and human host.

Furthermore, the invention includes the construction of multivalent recombinant measles-HPV vectors, in which two different antigens are simultaneously cloned and expressed in the same vector, conferring immunity against both of them.

Moreover, the invention relates to the combination of different recombinant measles-HPV viruses, each carrying and expressing a gene from a different HPV type, in order to elicit immune response in the host, directed against the different HPV types.

Furthermore, the invention comprises a method to produce a vaccine containing such recombinant viruses.

Moreover the invention also relates to the use of interleukin or interleukin-2 as adjuvent in order to increase the response of combined vaccine.

The invention finally relates to a vaccine capable to induce a potent and lifelong immune response against HPV and measles virus in human and to prevent from infection and/or treat diseases associated with infection.

TABLE 1

| Sera/immunisation | HPV Elisa Titer | HPV neutralization Titer |
|---|---|---|
| MV2EZ-HPV-L1 #1 | 2560 | 10240 |
| MV2EZ-HPV-L1 #2 | 10240 | 40960 |
| MV2EZ-HPV-L1 #3 | 10240 | 10240 |
| MV2EZ-HPV-L1 #4 | 10240 | 10240 |
| MV2EZ-HPV-L1 #5 | 10240 | 10240 |
| MV2EZ-HPV-L1 #6 | 10240 | 40960 |
| PBS (pooled sera) | 40 | 40 |
| MVEZ (pooled sera) | 40 | 40 |
| UV inactivated MV (pooled serum) | 40 | 40 |

DESCRIPTION OF THE FIGURES

FIG. 4a. Complete nucleotide sequence of p(+)MV$_2$EZ-GFP (19774 bp). (SEQ ID NO:1) The sequence can be described as follows with reference to the position of the nucleotides:

Figure 1:
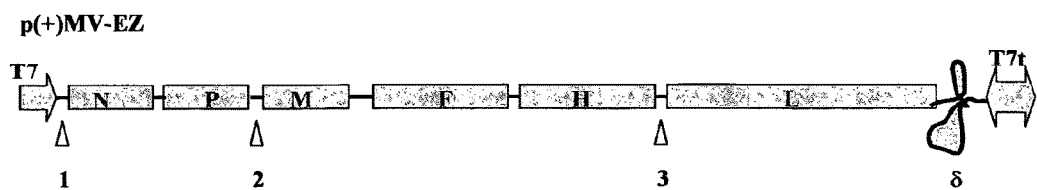
FIG. 1. Schematic representation of the antigenomic p(+)MV of measles virus. p(+)MV-EZ is a plasmid derived from pBluescript containing the complete sequence of the measles virus (Edmoston Zagreb), under the control of the T7 RNA polymerase promoter (T7), containing three ATU respectively in position 1 (before the N gene of the measles virus), 2 (between the P and the M genes of the measles virus) and 3 (between the H and the L genes of the measles virus), and exactly terminated by the hepatitis delta ribozyme and T7 RNA polymerase terminator (☐ T7t). The size of the plasmid is 18941 bp.

| 592-608 | T7 promoter |
|---|---|
| 609-17335 | MV Edmoston Zagreb antigenome |
| 4049-4054 | MluI restriction site |
| 4060-4065 | BssHII restriction site |
| 4066-4782 | Green Fluorescent Protein (GFP) ORF |
| 4786-4791 | BssHII restriction site |
| 4798-4803 | AatII restriction site |
| 17336-17561 | HDV ribozyme and T7 terminator |

FIG. 4b. Complete nucleotide sequence of p(+)MV$_3$EZ-GFP (19774 bp). (SEQ ID NO:2) The sequence can be described as follows with reference to the position of the nucleotides:

| 592-608 | T7 promoter |
|---|---|
| 609-17335 | MV Edmoston Zagreb antigenome |
| 9851-9856 | MluI restriction site |
| 9862-9867 | BssHII restriction site |
| 9868-10584 | Green Fluorescent Protein (GFP) ORF |
| 10588-10593 | BssHII restriction site |
| 10600-10605 | AatII restriction site |
| 17336-17561 | HDV ribozyme and T7 terminator |

FIG. 5a. ANL1TE: this is the HPV16-L1 sequence ORF (1518 bp) (SEQ ID NO:3) cloned by the inventors. The sequence can be described as follows with reference to the position of the nucleotides:

| 1-3 | Start codon |
|---|---|
| 4-1515 | HPV-L1 ORF |
| 1516-1518 | STOP codon |

FIG. 5b. HPV16-L2 sequence ORF. (SEQ ID NO:4) The sequence can be described as follows with reference to the position of the nucleotides:

| 1-3 | Start codon |
|---|---|
| 4-1419 | HPV-L2 ORF |
| 1420-1422 | STOP codon |

FIG. 5c. HPV16-E6 sequence ORF. (SEQ ID NO:5) The sequence can be described as follows with reference to the position of the nucleotides:

| | |
|---|---|
| 1-3 | Start codon |
| 4-474 | HPV-E6 ORF |
| 475-477 | STOP codon |

FIG. 5d. HPV16-E7 sequence ORF. (SEQ ID NO:6) The sequence can be described as follows with reference to the position of the nucleotides:

| | |
|---|---|
| 1-3 | Start codon |
| 4-294 | HPV-E7 ORF |
| 295-297 | STOP codon |

FIG. 5e. HPV18-L1 sequence ORF. (SEQ ID NO:7) The sequence can be described as follows with reference to the position of the nucleotides:

| | |
|---|---|
| 1-3 | Start codon |
| 4-1704 | HPV-L1 ORF |
| 1705-1707 | STOP codon |

FIG. 5f. HPV18-L2 sequence ORF. (SEQ ID NO:8) The sequence can be described as follows with reference to the position of the nucleotides:

| | |
|---|---|
| 1-3 | Start codon |
| 4-1386 | HPV-L2 ORF |
| 1387-1389 | STOP codon |

FIG. 5g. HPV18-E6 sequence ORF. (SEQ ID NO:9) The sequence can be described as follows with reference to the position of the nucleotides:

| | |
|---|---|
| 1-3 | Start codon |
| 4-474 | HPV-E6 ORF |
| 475-477 | STOP codon |

FIG. 5h. HPV18-E7 sequence ORF. (SEQ ID NO:10) The sequence can be described as follows with reference to the position of the nucleotides:

| | |
|---|---|
| 1-3 | Start codon |
| 4-315 | HPV-E7 ORF |
| 316-318 | STOP codon |

FIG. 5i. HPV6-L1 sequence ORF. (SEQ ID NO:11) The sequence can be described as follows with reference to the position of the nucleotides:

| | |
|---|---|
| 1-3 | Start codon |
| 4-1500 | HPV-L1 ORF |
| 1501-1503 | STOP codon |

FIG. 5j. HPV6-L2 sequence ORF. (SEQ ID NO:12) The sequence can be described as follows with reference to the position of the nucleotides:

| | |
|---|---|
| 1-3 | Start codon |
| 4-1377 | HPV-L2 ORF |
| 1378-1380 | STOP codon |

FIG. 5k. HPV6-E6 sequence ORF. (SEQ ID NO:13) The sequence can be described as follows with reference to the position of the nucleotides:

| | |
|---|---|
| 1-3 | Start codon |
| 4-450 | HPV-E6 ORF |
| 451-453 | STOP codon |

FIG. 5l. HPV6-E7 sequence ORF. (SEQ ID NO:14) The sequence can be described as follows with reference to the position of the nucleotides:

| | |
|---|---|
| 1-3 | Start codon |
| 4-294 | HPV-E7 ORF |
| 295-297 | STOP codon |

Figure 6:
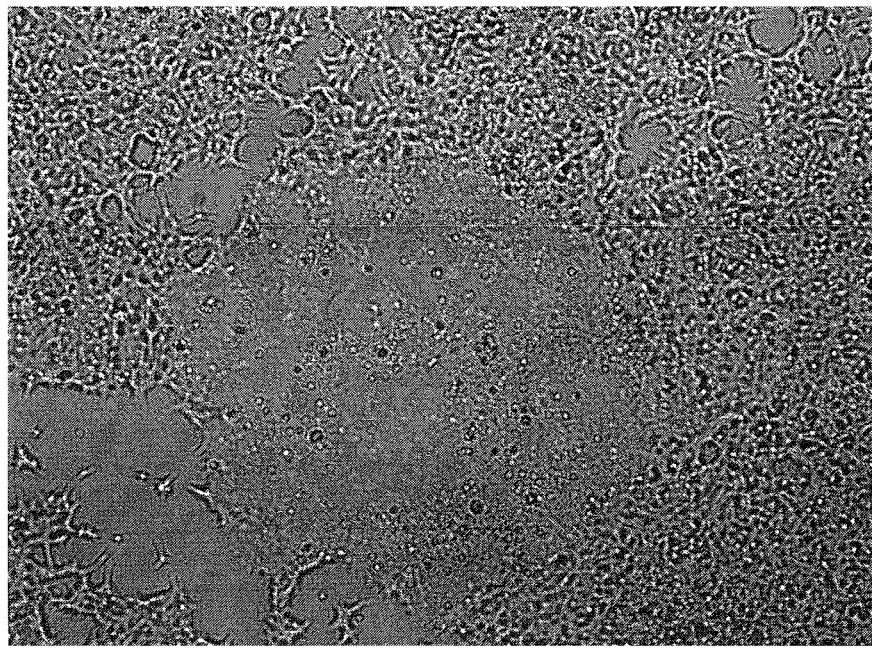

FIG. 6. Rescue of recombinant virus MV2EZ-L1 on 293-3-46 helper cells. Cells were co-transfected with 25 ng pEMCLa and 5 □g of the recombinant p(+)MV2EZ-L1 plasmid.

Figure 7:
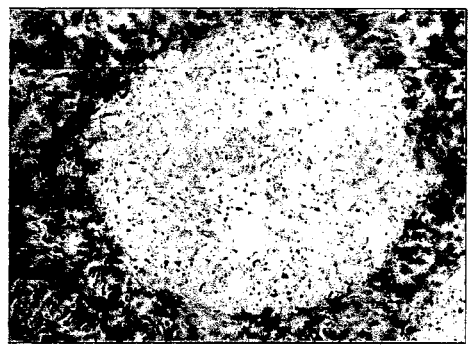

FIG. 7. Syncytium formation in Vero cells transfected with MV2EZ-L1. At 24 h p.i., cells were fixed with ethanol and stained with crystal violet.

FIG. 8. Growth curves of cell-associated (CA) and cell-free (CF) virus in MRC5cells. Monolayers were infected at an MOI of 0.05 with MV2EZ-L1 ed MVEZ virus.

FIG. 9. Expression of HPV-L1 from recombinant MVs by immunofluorescence analysis. Vero cells were infected with either MV2EZ-L1 (A) or MVEZ (B) at MOI 0.05 for 48 h and processed for indirect immunofluorescence. In upper panels specific HPV-L1 signal were detected with mouse monoclonal anti-HPV-L1 antibody, followed by goat anti-mouse antibody—FITC conjugate, in lower panels the same slides were stained with DAPI (4',6-diamidine-2-phenilindol chloridrate) and observed respectively with fluorescent or natural light.

Figure 10:
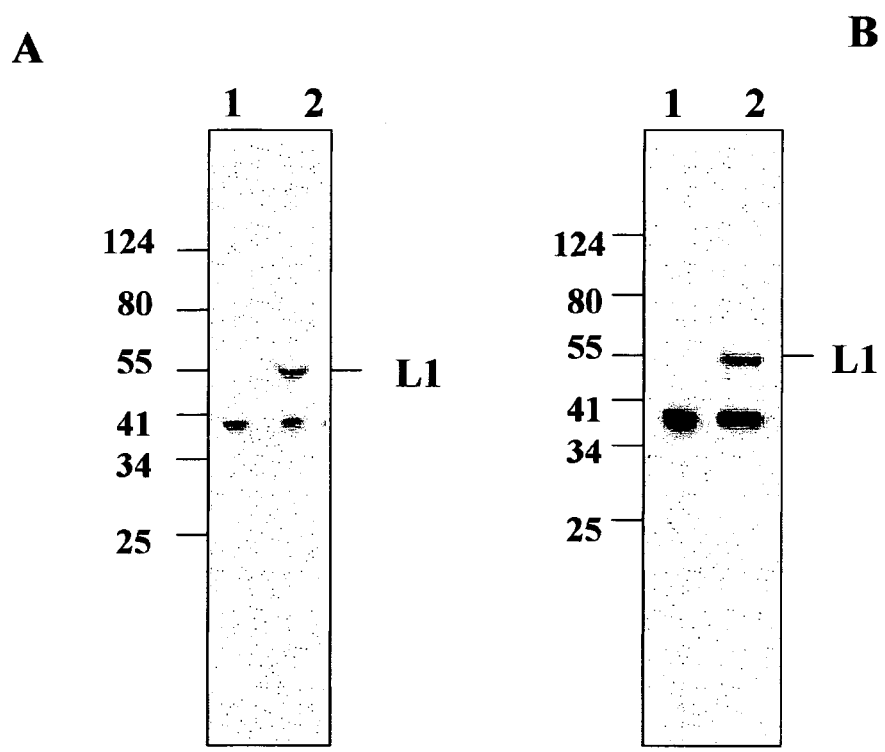

FIG. 10. Expression of HPV-L1 from recombinant MVs by Western blot analysis. Vero cells were infected with either MVEZ (1) or MV2EZ-L1 (2) at MOI 0.05 for 48 h. Expression of HPV-L1 in supernatant (A) and cell lysate (B) after infection with MVEZ (line 1) or MV2EZ-L1 (line 2).

Figure 11:
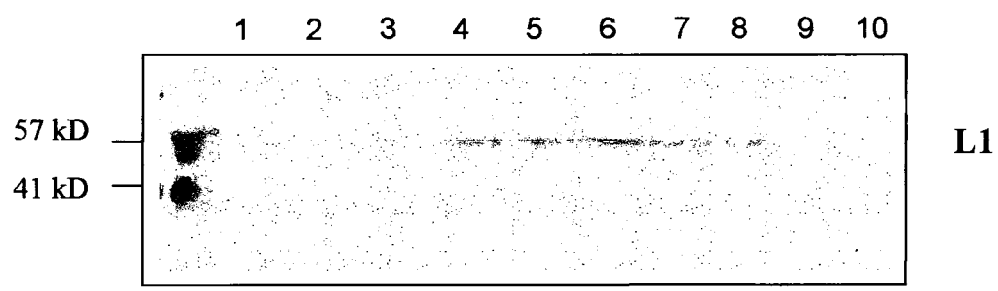

FIG. 11. Western blot analysis of HPV-L1 in the different CsCl gradient fractions.

The examples describe the invention.

EXAMPLE 1

Construction of Recombinant p(+)MV2EZ-HPV and p(+)MV3EZ-HPV Plasmids

All cloning procedures were basically as described in Sambrook et al. (1989).

All the restriction enzymes were from New England BioLabs; the oligonucleotides PCR primers were from Invitrogen.

The L1 sequence has been amplified by PCR, and direct cloned into the definitive MV vectors, obtaining two recombinant MV-HPV16-L1 plasmids: p(+)MV2EZ-HPV-L1 and p(+)MV3EZ-HPV-L1.

PCR amplification was carried out using the proof-reading Pfu DNA polymerase (Stratagene). DNA sequences of the synthetic oligonucleotides primers are given in upper case for the MV nucleotides and in lower case for non-MV nucleotides; sequences of relevant restriction endonucleases recognition sites are underlined. The following primers have been used: FOR-L1 5'-ttg gcgcgccATGAGCCTGTGGCTGCCC-3'; REV-L1 5'-at gacgtcTCACAGCTTCCTCTTCTTCCTC-3'.

For-L1 contains an overhang (in lower case) with BssHII restriction site (gcgcgc), after 3-bp long-protection site (ttg).

Rev-L1 contains an overhang (in lower case) with AatII restriction site (gacgtc).

Figure 2:
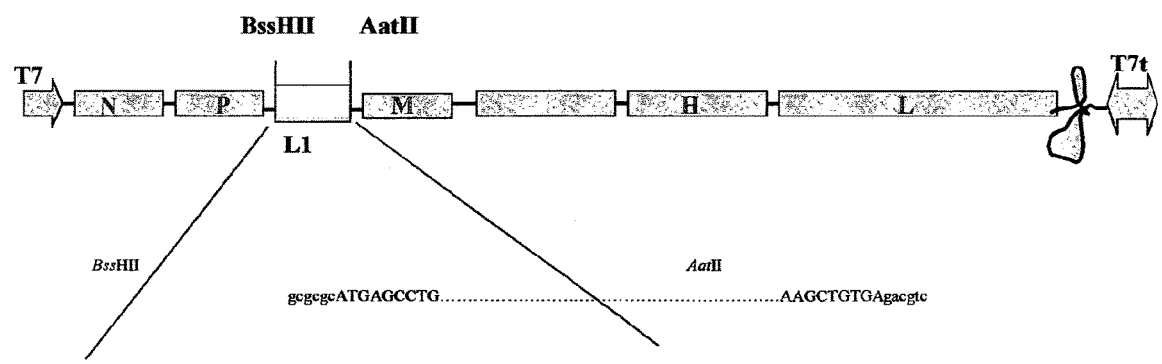
FIG. 2. Schematic representation of the recombinant measles-papilloma plasmid, p(+)MV$_2$-EZ-L1. It is a plasmid derived from p(+)MV-EZ containing HPV-L1 gene (type 16), 1518 bp, cloned in position two of the measles genome by BssHII-AatII digestion. The size of the recombinant plasmid is 20561 bp.
Figure 3:
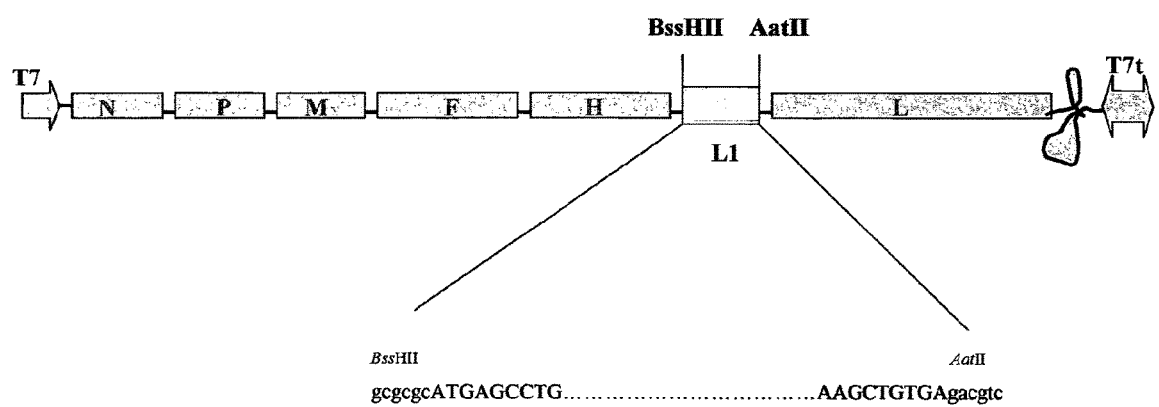
FIG. 3. Schematic representation of the recombinant measles-papilloma plasmid, p(+)MV$_3$-EZ-HPV-L1 It is a plasmid derived from p(+)MV-EZ containing the HPV-L1 gene (type 16), 1518 bp, cloned in position three of the measles genome by BssHII-AatII digestion. The recombinant plasmid p(+)MV$_3$-EZ-HPV-L1 is 20561 bp.

The obtained PCR-HPV16-L1 (1536 bp) has been cloned in the p(+)MVEZ vector (FIG. 1) between genes for P and M protein (position 2, FIG. 2) or between H and L (position 3, FIG. 3), after digestion with BssHII+AatII. Ligations were performed overnight at 16° C. in an equimolar ratio respect to the pre-digested MeV$_2$EZ and MeV$_3$EZ vectors BssHII+AatII (19 Kb in length), using one unit of T4 DNA Ligase, obtaining, respectively, p(+)$MV_2$EZ-L1 (20561 bp) and p(+)$MV_3$EZ-L1 (20561 bp). In FIGS. 4 and 5 are listed, respectively, the sequences of the vectors p(+)$MV_2$EZ-GFP and p(+)$MV_3$EZ-GFP.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences, aligned with the assumed ones using a DNA Strider software, showed 100% identity. Nucleotide sequence encoding for HPV16-L1 is presented in FIG. 5*a*.

All the other antigens L2, E6, and E7 from HPV16, and L1, L2, E6, and E7 from HPV 18 and 6 types, have been cloned as above detailed.

The ORFs sequences are listed in FIG. 5 (5*b* to 5*l*).

List of the Recombinant MV-HPV Plasmids from HPV 16, 18, and 6 Types:

p(+)MV2EZ-HPV16-L1 plasmid
p(+)MV3EZ-HPV16-L1 plasmid
p(+)MV2EZ-HPV16-L2 plasmid
p(+)MV3EZ-HPV16-L2 plasmid
p(+)MV2EZ-HPV16-E6 plasmid
p(+)MV3EZ-HPV16-E6 plasmid
p(+)MV2EZ-HPV16-E7 plasmid
p(+)MV3EZ-HPV16-E7 plasmid
p(+)MV2EZ-HPV18-L1 plasmid
p(+)MV3EZ-HPV18-L1 plasmid
p(+)MV2EZ-HPV18-L2 plasmid
p(+)MV3EZ-HPV18-L2 plasmid
p(+)MV2EZ-HPV18-E6 plasmid
p(+)MV3EZ-HPV18-E6 plasmid
p(+)MV2EZ-HPV18-E7 plasmid
p(+)MV3EZ-HPV6-E7 plasmid
p(+)MV2EZ-HPV6-L1 plasmid
p(+)MV3EZ-HPV6-L1 plasmid
p(+)MV2EZ-HPV6-L2 plasmid
p(+)MV3EZ-HPV6-L2 plasmid
p(+)MV2EZ-HPV6-E6 plasmid
p(+)MV3EZ-HPV6-E6 plasmid
p(+)MV2EZ-HPV6-E7 plasmid
p(+)MV3EZ-HPV6-E7 plasmid

EXAMPLE 2

Cells and Viruses

Cells were maintained as monolayers in Dulbecco's Modified Eagles Medium (DMEM), supplemented with 5% Foetal Calf Serum (FCS) for Vero cells (African green monkey kidney) and with 10% FCS and 1% penicillin/streptomycin for 293T cells (human embryonic kidney); DMEM supplemented with Glutamax (F12) and 10% FCS for MRC-5 (human foetal fibroblast); DMEM supplemented with 10% FCS and 1.2 mg/ml of G 418 for 293-3-46.

To grow MV virus stocks reaching titers of about $10^7$ pfu/ml, recombinant viruses and the vaccine strain Edmoston Zagreb were propagated in MRC-5 cells: plaque purification was carried out by transferring a syncythium to 35 mm MRC-5 cell culture which was expanded first to a 10 cm dish, and afterwards to a 175 cm flask. Virus stocks were made from 175 $cm^2$ cultures when syncythia formation was about 90% pronounced. Medium corresponding to the so-called "free-cell virus fraction" was collected, freeze and thaw three times and spin down to avoid cell debris. The medium was then stored at −80° C. Cells, which correspond to the so-called "cell-associated virus fraction", were scraped into 3 ml of OPTIMEM (Gibco BRL) followed by three rounds freezing and thawing, spin down and the cleared surnatant stored at −80° C.

EXAMPLE 3

Transfection of Plasmids and Rescue of MV Viruses

Recombinant measles-HPV vaccine viruses have been obtained using the 293-3-46 helper cell (human embryonic kidney cells), stably expressing the measles N and P proteins as well as the T7 RNA polymerase. The viral RNA polymerase (large protein, L) was expressed by co-transfecting the cells with 15 ng of the plasmid peMCLa. Calcium-phosphate method was used for transfection.

293T-3-46 cells were seeded into a 35 mm well to reach ~50-70% confluence when being transfected. 4 h before transfection, the medium was replaced with 3 ml DMEM containing 10% FCS. All recombinant plasmids were prepared according to the QIAGEN plasmid preparation kit. The kit for the Ca2+phosphate coprecipitation of DNA was from Invitrogen.

Cells were co-transfected with the plasmids in the follows final concentration: pEMCLa 25 ng and the recombinant p(+)MV2EZ-L1 plasmid 5 µg. All plasmids, diluted in H2O, were added in a Eppendorf tube containing 2M CaCl2, the mix was added to another Eppendorf tube containing HEPES buffer under shaking conditions, and was incubated 30 min at room temperature (RT). Thus, the co-precipitates were added dropwise to the culture and the transfection was carried out at 37° C. and 5% CO2 for about 18 h. Then, the transfection medium was replaced with 3 ml of DMEM containing 10% FCS.

First syncytia appeared 3-4 days after transfection when the cells were still subconfluent as shown in FIG. 6. To allow syncytia formation to progress more easily, almost confluent cell monolayers of each 35 mm well were then transferred to a 10 cm dish. Each syncytium was taken up in 300 µl of transfection medium and put in a sterile Eppendorf tube containing 700 µl of OPTIMEM, freeze and thaw for three rounds, and stored at −80° C.

EXAMPLE 4

Virus Titration by Plaque Assay

Serial 10-times dilutions of virus preparations were carried out using OPTIMEM to a final volume of 0.5 ml. Each dilution was added on 35 mm Vero cell cultures. After 1 h of virus adsorption, the inoculum was removed and the infected cells were overlaid with 2 ml of DMEM containing 5% FCS and 1% low melting point agarose (LMP agarose). After 5 days of incubation at 37° C. and 5% CO2, cultures were fixed with 1 ml of 10% TCA for 1 h, then UV cross-linked for 30 min. After removal of the agarose overlay, cell monolayers were stained with crystal violet dissolved in 4% ethanol, washed with water and the plaques were counted under the inverted microscope (FIG. 7).

EXAMPLE 5

MRC-5 Virus Serial Passages of Recombinant Viruses

Rescued viruses were serially passaged 10-times on MRC5 cells, seeded into 10 cm diameter plates, that were infected with the standard and the recombinant MV viruses at MOI of 0.01 PFU/cells. After monolayer was full infected, 1% surnatant of each culture was used to infect the subsequent MRC5 cells monolayer. To test transgene expression and stability, viruses from passage 1, 5, and 10 were used for further characterisation of expression by Western blot and immunofluorescence.

EXAMPLE 6

Growth Kinetics Curve

MRC5 cells seeded on 35 mm dish ($1-5 \times 10^5$) were monitored for 90% confluence and infected with cleared virus suspension from cell-associated virus fraction at 0.05 MOI, including MVEZ as control. Samples, corresponding to the so-called "free-cell virus fraction" and to the so-called "cell-associated virus fraction", were collected daily for one week and titrated. From Growth curve comparison of it is interesting that the replication of MV2EZ-L1 was only slightly impaired: the recombinant virus reached peak titers of $6.12 \times 10^6$ TCID50 s/ml 48 hpi, whereas MVEZ gave final titers of $6.8 \times 10^6$ TCID50 s/ml 36 hpi (FIG. 8). The slightly slower progression of replication was also reflected in somewhat reduced plaque sizes. MV2EZ-L1 produced plaques with an average diameter of 0.83 mm, while MVEZ produced plaques with an average diameter of 0.91 mm.

EXAMPLE 7

Protein Expression Analyses

To analyse the expression either MV and HPV antigen, immunofluorescence, Western blot and isolation of VLP were carried out.
Immunofluorescence
Vero cells were seeded on 24 mm×24 mm glass cover slips in 35 mm wells, cultured overnight and infected with rescued recombinant virus MV2EZ-L1 or with negative control virus MVEZ at 0.05b M.O.I. 48 hours after infection cells on coverslips were fixed with 4% paraformaldehyde in PBS, and permeabilized with 0.1% TX-100, washed with blocking solution (PBS containing 1% BSA) for 1 h, and stained with the specific HPV-L1 mouse monoclonal antibody (Biogenesis) and by FITCH conjugated goat antimouse secondary antibody.
All syncytia of rescued MV2EZ-L1 showed positive signals (FIG. 9 upper panel, left images), whereas the syncytia of rescued MVEZ (FIG. 9, upper panel right images) showed no fluorescence, that indicates that all syncytia induced by MV2EZ-L1 expressed L1 antigen.

Western Blot
For Western blot, Vero cells seeded on 35 mm dish ($1-5 \times 10^5$) were monitored the next day for 90% confluence and infected with cleared virus suspension from cell-associated virus fraction, using 0.05 MOI (Multiplicity Of Infection), including MVEZ as control. When about 80% syncythia formation was observed, proteins from medium and from cells were analysed. Cells were first washed with PBS and then scraped in 1 ml PBS and collected in an Eppendorf tube, and centrifuge at 2000 RPM/4 min. Cells were then lysed 5 min/RT with 70 µl of lysis buffer (1% NP-40, 50 mM Tris pH 8, 150 mM NaCl) supplemented with protease inhibitor cocktail (Complete Mini, Roche, 1 836 153). Surnatants were cleared by centrifuge at 13000 RPM/5 min, and transferred into a new tube: 30 □l of 4× loading buffer (Invitrogen) were added; samples were mixed and boiled at 95° C./2 min, spun down and stored at −20° C.
An SDS-PAGE migration was performed, running a NuPAGE 12% Bis-acrylamide gel in reducing conditions, using 1× Running Buffer, for 50 min at 200V (start 100-125 mA, end 60-80 mA). Then, semi-dry method was used to transfer separated cell-proteins to Nitrocellulose Membrane, at 14V/1h30.
Mouse monoclonal antibody against HPV-L1 (Biogenesis) was used as first antibody. The second antibody was a goat anti-mouse antibody coupled to horse-radish peroxidase allowing the visualization of the bands by the enhanced chemiluminescence kit (ECLTM, Amersham LifeScience).
The anti-HPVL1 antibody reacted with a protein of approximately 55 kDa released in the culture medium of MV2EZ-L1-infected cells, whereas no such protein was detected in culture medium of MVEZ-infected cells (FIG. 10, panel A) as well as with a protein of approximately 55 kDa synthesized in the MV2EZ-L1-infected cells, whereas no such protein was detected in MVEZ-infected cell lysates (FIG. 10, panel B). This result indicates that MV2EZ-L1-infected cells express and secrete the L1 protein that is similar in size to the authentic L1 protein from HPV.
Isolation of VLPs
Monolayer Vero cells grown were infected at 0,1 MOI with recombinant virus MV2EZ-L1 or negative control virus MVEZ and incubated at 37°. 1 hour after viral adsorption medium was substituted by DMEM containing 5% FCS and incubated at 37° for 48 hours to obtain 90% syncytia. Medium from infected cells has been collected, centrifugated and submitted to centrifugation on a 40% (w/v) saccharose layer to separate proteins from particles at 110, 00×g for 2.5 h at 4°. Pellet was successively solubilised in cesium chloride 27% (w/w) in PBS and analysed on density gradient centrifugation in cesium chloride 27% (w/w) in PBS for 20 h at 141,000 g at 4°. Gradient fractions were analyzed for the presence of HPV-L1 by SDS-page electrophoresis and western blot (FIG. 11).

EXAMPLE 8

Mice Immunisation

The immunogenic power of the rescued recombinant MV-HPV viruses described was proved by immunisation tests performed on transgenic mice CD46, susceptible for MV infections. The animals were kept under optimal hygienic conditions and were immunized at 6-8 weeks of age. Immunisation was performed intra-peritoneal using $10^5$ PFU of each recombinant MV-HPV in two injections, at 0 and 4 weeks. Non-infected mice as well as mice immunized with PBS served as control. UV inactivated MV was used as a control to determine the effect of virus replication on activation of immune responses.

The presence of MV-specific antibodies in the sera from the immunised CD46 mice (at least 6 per group) was determined by ELISA using 96-microwell plates, coated with Measles virus EIA bulk (ATCC VR-24), for IgG antibody detection. Protein was diluted 0.6 µg/ml with 0.05 M carbonate buffer (pH 9.4), and 100 µl per well was added to 96-well-microtiter plates. The plates were incubated overnight at 4° C., washed with PBS/0.05% Tween 20 (PT) (ph 7.4), incubated with PT (0.1 ml/well)-10% BSA for 60 min at 37° C., and washed again with PT. Serial 2-folds dilutions of the tested sera were added (100 µl/well), and the plates were incubated for 60 min at 37° C. The plates were washed with PT and were incubated with 100 µl of goat anti-mouse IgG HRP diluted 1:2000 in PBS-0.05% Tween 20 for 30 min at 37° C. The plates were washed with PT and incubated with 100 µl OPD (o-Phenylendiamin, Fluka 78411). The reaction was stopped after 3-4 min. Plates were read on a MicroElisa Reader at a wave length of 490 nm. Readings higher than three-folds negative controls were scored as positive reaction.

The presence HPVL1-specific antibodies in the sera of immunised CD46 mice was determined by ELISA assay and by neutralization assay.

Briefly, for the Elisa assay, 96-microwell plates were coated with HPVL1 antigen, diluted with carbonate buffer pH 9.4 at a concentration of 2-50 ng/well. The plates were incubated overnight at 4° C., washed with PBS/0.05% Tween 20 (PT). Subsequently, unspecific interaction were blocked with 10% defatted milk dissolved in PT for 1 hour at 37° C. and wells were washed again with PT. The plates were consecutively incubated with various dilutions of mouse sera (starting at 1:200, followed by serial two-fold dilutions), peroxidase-conjugate goat anti-mouse IgG and with OPD substrate. Optical density values were measured at 490 nm. Values above the cut-off background level (mean value of sera from MV immunised mice multiplied by a factor of 2.1) were considered positive. Titres were depicted as reciprocal end-dilutions.

To assay for neutralizing antibodies twofold serum dilutions were incubated with 50 PFU of recombinant for 1 h at 37° C. and plated in duplicate onto 104 Vero cells/well (96-well plate). Five days later titers were determined microscopically. The endpoint titer was calculated as the highest serum dilution tested that reduced the number of PFU by at least 50%

The specific immune responses to HPV-L1 is shown in table I. The titers in both the Elisa and neutralization assays are similar to those observed in women or mice after three injections of VLPs. Moreover, the very similar titers observed in the two assays indicate that most of the L1 expressed is conformationally correct.

EXAMPLE 9

Purification of Recombinant Measles Virus Expressing Malaria Antigens from Defecting Interfering Particles (DIs) by Plaque Purification It is known from literature that after a certain number of passages with Paramyxoviruses, and in particular with measles virus, an accumulation of defective interfering particles (DIs) will occur (23, 24). It has been described that these DIs develop various defects: negative impact on vaccine safety, negative influence on virus yields in production, genome instability and suppression of immune reaction after vaccination. In order to avoid such DIs with our new recombinant viruses, we have applied the method of plaque purification as described in example 7 with the exception that we use MRC5 cell instead of Vero cell. After the formation of clear, well defined syncytia we aspirated under the microscope with a micropipette such material for further passaging in a fresh MRC5 tissue colture.

EXAMPLE 10

Purification of Recombinant Measles Virus Expressing Malaria Antigens from Defecting Interfering Particles (DIs) by End Point Dilution The end point dilution technique was applicated in microplates: in all wells a fresh monolayer with MRC5 cells had just developed. The virus suspension containing recombinant measles-malaria viruses was prepared in two fold dilutions. From the well of the latest monolayer where a syncytia was detected the supernatant was aspirated with a pipette. The supernatant was mixed with a suspension containing MRC5 cells. This mixture was incubated at 4° C. for 1 hour. Finally, it was transferred in a small Costar flask and incubated at 35° C.+5% $CO_2$ and harvested for purify recombinant measles-malaria virus after ten days.

EXAMPLE 11

Production of a Combined Measles-Malaria Vaccine

The working seed of the described recombinant measles-malaria virus has been incubated on MRC5 cell monolayer in 1750 cm2 roller bottles at 35° C. for ten days. The cells have been monitored every day for status of health and confluence. On day ten at highest level of syncytia formation, the supernatant was pumped in a steel cylinder for storage in liquid nitrogen. The same procedure was repeated two days later. After performing of all the tests (virus titer, genome stability, virus safety, cell safety, chemical analysis, sterility and others), the harvests have been thawed up and mixed with stabilizer containing gelatine, sorbitol, ammi-noacids and other sugars to final dilution of 105. With a automated filling machine small lyo bottles (F3) have been inoculated with 0.5 ml each. A specially calculated lyophilisation program is used to guarantee maximal survival of the product during the freeze-drying process.

BIBLIOGRAPHY

1. Walboomers J M, Jacobs M V, Manos M M, et al. Human papillomavirus is a necessary cause of invasive cervical cancer worldwide. J Pathol 1999; 189:12-19
2. Pei X F. The human papillomavirus E6/E7 genes induce discordant changes in the expression of cell growth regulatory proteins. Carcinogenesis 1996; 17: 1395-1401
3. Winters U, Roden R, Kitchener H and Stern P. Progress in the development of a cervical cancer vaccine. Therapeutics and Clinical Risk Management 2006; 2 259-269.
4. Griffin D. Fields Virology, fifth edition (2007), eds.-in-chief Knipe, D. M. &. Howley, P. M. Lippincott Williams & Wilkins, Philadelphia Pa. 19106, USA
5. Clements C J and Cutts F T. The epidemiology of measles: thirty years of vaccination. 1995 Curr Top Microbiol Immunol. 1995; 191:13-33

6. Enders J F and Peebles T C, Propagation in tissue cultures of cytopathogenic agents from patients with measles. Proc Soc Exp Biol Med 1954; 86:277-86

7. Ovsyannikova I G., Reid, K. C., Jacobson, R. M., Oberg, A. L., Klee, G. G., Poland, G. A. (2003). Cytokine production patterns and antibody response to measles vaccine. Vaccine, 21(25-26): 3946-53.

8. Radecke, F., P. Spielhofer, H. Schneider, K. Kaelin, M. Huber, K. Dötsch, G. Christiansen, and M. Billeter. (1995). Rescue of measles viruses from cloned DNA. EMBO Journal. 14: 5773-5784.

9. Lorin C, Mollet L, Delebecque F, Combredet C, Hurtrel B, Charneau P, et al. A single injection of recombinant measles virus vaccines expressing human immunodeficiency virus (HIV) type 1 clade B envelope glycoproteins induces neutralizing antibodies and cellular immune responses to HIV. J Virol 2004; 78(1):146-57.

10. Singh M, Cattaneo R, Billeter M A. A recombinant measles virus expressing hepatitis B virus surface antigen induces humoral immune responses in genetically modified mice. J Virol 1999; 73(6):4823-8.

11. Wang Z, Hangartner L, Cornu T I, Martin L R, Zuniga A, Billeter M A, et al. Recombinant measles viruses expressing heterologous antigens of mumps and simian immunodeficiency viruses. Vaccine 2001; 19(17-19):2329-36.

12. Despres P, Combredet C, Frenkiel M P, Lorin C, Brahic M, Tangy F. Live measles vaccine expressing the secreted form of the West Nile virus envelope glycoprotein protects against West Nile virus encephalitis. J Infect Dis 2005; 191(2):207-14.

13. Fehr T, Naim H Y, Bachmann M F, Ochsenbein A F, Spielhofer P, Bucher E, et al. T-cell independent IgM and enduring protective IgG antibodies induced by chimeric measles viruses. Nat Med 1998; 4(8):945-8.

14. Brandler S, Tangy F (2007) Recombinant vector derived from live attenuated measles virus: Potential for flavivirus vaccines. Comp Immunol Microbiol Infect Dis 15. Brandler S, Lucas-Hourani M, Moris A, Frenkiel M P, Combredet C, Février M, Bedouelle H, Schwartz O, Desprès P and Tanguy F. Pediatric measles vaccine expressing a Dengue antigen induces durable serotype-specific neutralyzing antibodies to Dengue virus. (2007) Plos Negl Trop Dis 1(3):e96)

16. Tangy F, Naim H Y. Live attenuated measles vaccine as a potential multivalent pediatric vaccination vector. Viral Immunol 2005; 18(2):317-26.

```

The invention claimed is:

1. A combined measles human papillomavirus (HPV) vaccine comprising recombinant measles vaccine viruses which express HPV antigens capable of eliciting immune response and protection both against measles and HPV wherein the antigens derived from HPV comprise L 1 protein HPV16 or HPV18.

2. The combined measles HPV vaccine as claimed in claim 1, wherein the recombinant measles vaccine viruses express at least one L1 protein of a single or different HPV types.

3. The combined measles HPV vaccine as claimed in claim 2, wherein the combined measles HPV vaccine further comprising recombinant measles vaccine viruses expressing a protein selected from HPV6 L1, HPV11 L1 HPV16 L2, HPV18 L2, HPV6 L2, HPV11 L2, HPV16 E6, HPV18 E6, HPV6 E6, HPV16 E7, HPV18 E7, and HPV6 E7.

4. The combined measles HPV vaccine as claimed in claim 1, wherein the HPV antigens are produced in a mammalian expression system.

5. The combined measles HPV vaccine as claimed in claim 4, wherein the mammalian expression system is 293T 3 46 cell.

6. The combined vaccine according to claim 1, wherein the recombinant measles virus is recombinant measles virus of an Edmoston Edmonston Zagreb strain.

7. The combined vaccine according to claim 1, further comprising a recombinant measles virus having inserted a nucleic acid sequence encoding HPV16 E6, HPV18 E6 or HPV6 E6.

8. The combined vaccine according to claim 1, further comprising a recombinant measles virus having inserted a nucleic acid sequence encoding HPV16 E7, HPV18 E7, or HPV6 E7.

9. The combined vaccine according to claim 1, further comprising a recombinant measles virus having inserted a nucleic acid sequence encoding HPV6 L1, HPV11 L1, HPV16 L2, HPV18 L2, HPV6 L2, HPV11 L2, HPV16 E6, HPV 18 E6, HPV6 E6, HPV 16 E7, HPV 18 E7 or HPV6 E7 or any combination thereof.

10. The combined vaccine according to claim 1, further comprising a recombinant measles virus that comprises at least two or three nucleic acid sequences encoding simultaneously two or three of:
 (a) at least one L 1 protein of single or different HPV types;
 (b) at least one L2 protein of single or different HPV types; or
 (c) at least one of E6 or E7 protein of single or different HPV types.

11. The combined vaccine according to claim 1, wherein the combined vaccine comprises recombinant measles viruses that comprise one or more of the nucleic acid sequences encoding HPV16-L1, HPV16-L2, HPV16-E6, HPV16-E7, HPV18-L1, HPV18-L2, HPV18-E6, HPV18-E7, HPV6-L1, HPV6-L2, HPV6-E6, and HPV6-E7.

12. The combined vaccine according to claim 1, wherein the recombinant measles viruses further encode a protein with adjuvantic properties.

13. The combined vaccine according to claim 12, wherein the adjuvant is an interleukin.

14. The combined vaccine according to claim 1, wherein the vaccine essentially consists of at least one of the recombinant measles HPV viruses or a mixture of two to several such viruses.

15. The combined vaccine according to claim 1, wherein the recombinant measles HPV viruses or a mixture of two to several such viruses devoid of defective interfering particles (DIs).

16. The combined vaccine according to claim 1, wherein adventitiously arisen DI particles have been eliminated by:
 (a) plaque purification;
 (b) end point dilution; or
 (c) a physical method.

17. The combined vaccine according to claim 16, wherein the physical method is centrifugation.

18. The combined vaccine according to claim 1, further comprising rubella, mumps, varicella or another life attenuated vaccine virus, naturally attenuated or recombinant, alone or in combination.

19. The combined vaccine according to claim 1, which is mixed with:
   (a) a suitable stabilizer, and sorbitol for parenteral application;
   (b) a suitable stabilizer and/or adjuvant suitable for intranasal application;
   (c) a suitable stabilizer and/or adjuvant for inhalation application;
   (d) a suitable stabilizer and/or adjuvant suitable for oral application;
   (e) a suitable stabilizer and/or adjuvant suitable for any suppository formulation; or
   (f) a suitable stabilizer and/or adjuvant suitable for transdermal application.

20. The combined vaccine according to claim 12, wherein the interleukin is interleukin 2.

21. The combined measles-HPV vaccine according to claim 1, wherein the combined measles-HPV vaccine comprises recombinant measles virus that comprises one or more of the coding sequences as set forth in SEQ ID NOs:3 to 14.

\* \* \* \* \*

SEQUENCE LISTING

<160> NUMBER OF SEQ ID NOS: 14

<210> SEQ ID NO 1
<211> LENGTH: 19774
<212> TYPE: DNA
<213> ORGANISM: Human Papilloma Virus

<400> SEQUENCE: 1
cacctaaatt gtaagcgtta atattttgtt aaaattcgcg ttaaattttt gttaaatcag      60
ctcatttttt aaccaatagg ccgaaatcgg caaaatccct tataaatcaa aagaatagac     120
cgagataggg ttgagtgttg ttccagtttg gaacaagagt ccactattaa agaacgtgga     180
ctccaacgtc aaagggcgaa aaaccgtcta tcagggcgat ggcccactac gtgaaccatc     240
accctaatca agttttttgg ggtcgaggtg ccgtaaagca ctaaatcgga accctaaagg     300
gagcccccga tttagagctt gacggggaaa gccggccatt taggccatag ggcgctggca     360
agtgtagcgg tcacgctgcg cgtaaccacc acacccgccg cgcttaatgc gccgctacag     420
ggcgcgtccc attcgccatt caggctgcgc aactgttggg aagggcgatc ggtgcgggcc     480
tcttcgctat tacgccagct ggcgaaaggg ggatgtgctg caaggcgatt aagttgggta     540
acgccagggt tttcccagtc acgacgttgt aaaacgacgg ccagtgaatt gtaatacgac     600
tcactataac caaacaaagt tgggtaagga tagttcaatc aatgatcatc ttctagtgca     660
cttaggattc aagatcctat tatcagggac aagagcagga ttagggatat ctgagatggc     720
cacactttta aggagcttag cattgttcaa aagaaacaag gacaaaccac ccattacatc     780
aggatccggt ggagccatca gaggaatcaa acacattatt atagtaccaa tccctggaga     840
ttcctcaatt accactcgat ccagacttct ggaccggttg gtcaggttaa ttggaaaccc     900
ggatgtgagc gggcccaaac taacaggggc actaataggt atattatcct tatttgtgga     960
gtctccaggt caattgattc agaggatcac cgatgaccct gacgttagca taaggctgtt    1020
agaggttgtc cagagtgacc agtcacaatc tggccttacc ttcgcatcaa gaggtaccaa    1080
catggaggat gaggcggacc aatacttttc acatgatgat ccaattagta gtgatcaatc    1140
caggttcgga tggttcgaga acaaggaaat ctcagatatt gaagtgcaag accctgaggg    1200
```

```
attcaacatg attctgggta ccatcctagc ccaaatttgg gtcttgctcg caaaggcggt    1260
tacggcccca gacacggcag ctgattcgga gctaagaagg tggataaagt acacccaaca    1320
aagaagggta gttggtgaat ttagattgga gagaaaatgg ttggatgtgg tgaggaacag    1380
gattgccgag gacctctcct tacgccgatt catggtcgct ctaatcctgg atatcaagag    1440
aacacccgga aacaaaccca ggattgctga aatgatatgt gacattgata catatatcgt    1500
agaggcagga ttagccagtt ttatcctgac tattaagttt gggatagaaa ctatgtatcc    1560
tgctcttgga ctgcatgaat ttgctggtga gttatccaca cttgagtcct tgatgaacct    1620
ttaccagcaa atgggggaaa ctgcacccta catggtaatc ctggagaact caattcagaa    1680
caagttcagt gcaggatcat accctctgct ctggagctat gccatgggag taggagtgga    1740
acttgaaaac tccatggggg gtttgaactt tggccgatct tactttgatc cagcatattt    1800
tagattaggg caagagatgg taaggaggtc agctggaaag gtcagttcca cattggcatc    1860
tgaactcggt atcactgccg aggatgcaag gcttgtttca gagattgcaa tgcatactac    1920
tgaggacaag atcagtagag cggttggacc cagacaagcc caagtatcat ttctacacgg    1980
tgatcaaagt gagaatgagc taccgagatt ggggggcaag gaagatagga gggtcaaaca    2040
gagtcgagga gaagccaggg agagctacag agaaaccggg cccagcagag caagtgatgc    2100
gagagctgcc catcttccaa ccggcacacc cctagacatt gacactgcat cggagtccag    2160
ccaagatccg caggacagtc gaaggtcagc tgacgccctg cttaggctgc aagccatggc    2220
aggaatctcg gaagaacaag gctcagacac ggacacccct atagtgtaca atgacagaaa    2280
tcttctagac taggtgcgag aggccgaggg ccagaacaac atccgcctac cctccatcat    2340
tgttataaaa aacttaggaa ccaggtccac acagccgcca gcccatcaac catccactcc    2400
cacgattgga gccaatggta aagagcagg cacgccatgt caaaaacgga ctggaatgca    2460
tccgggctct caaggccgag cccatcggct cactggccat cgaggaagct atggcagcat    2520
ggtcagaaat atcagacaac ccaggacagg agcgagccac ctgcagggaa gagaaggcag    2580
gcagttcggg tctcagaaaa ccatgcctct cagcaattgg atcaactgaa ggcggtgcac    2640
ctcgcatccg cggtcaggga cctggagaga gcgatgacga cgctgaaact ttgggaatcc    2700
ccccaagaaa tctccaggca tcaagcactg ggttacagtg ttattacgtt tatgatcaca    2760
gcggtgaagc ggttaaggga atccaagatg ctgactctat catggttcaa tcaggccttg    2820
atggtgatag caccctctca ggaggagaca atgaatctga aacagcgat gtggatattg    2880 gcgaacctga taccgaggga tatgctatca ctgaccgggg atctgctccc atctctatgg    2940
ggttcagggc ttctgatgtt gaaactgcag aaggagggga gatccacgag ctcctgagac    3000
tccaatccag aggcaacaac tttccgaagc ttgggaaaac tctcaatgtt cctccgcccc    3060
cggaccccgg tagggccagc acttccggga cacccattaa aaagggcaca gacgcgagat    3120
tagcctcatt tggaacggag atcgcgtctt tattgacagg tggtgcaacc caatgtgctc    3180
gaaagtcacc ctcggaacca tcagggccag gtgcacctgc ggggaatgtc cccgagtgtg    3240
tgagcaatgc cgcactgata caggagtgga cacccgaatc tggtaccaca atctccccga    3300
gatcccagaa taatgaagaa gggggagact attatgatga tgagctgttc tctgatgtcc    3360
aagatattaa aacagccttg gccaaaatac acgaggataa tcagaagata atctccaagc    3420
tagaatcact gctgttattg aagggagaag ttgagtcaat taagaagcag atcaacaggc    3480
aaaatatcag catatccacc ctggaaggac acctctcaag catcatgatc gccattcctg    3540
```

-continued

```
gacttgggaa ggatcccaac gaccccactg cagatgtcga aatcaatccc gacttgaaac    3600
ccatcatagg cagagattca ggccgagcac tggccgaagt tctcaagaaa cccgttgcca    3660
gccgacaact ccaaggaatg acaaatggac ggaccagttc cagaggacag ctgctgaagg    3720
aatttcagct aaagccgatc gggaaaaaga tgagctcagc cgtcgggttt gttcctgaca    3780
ccggccctgc atcacgcagt gtaatccgct ccattataaa atccagccgg ctagaggagg    3840
atcggaagcg ttacctgatg actctccttg atgatatcaa aggagccaat gatcttgcca    3900
agttccacca gatgctgatg aagataataa tgaagtagct acagctcaac ttacctgcca    3960
accccatgcc agtcgaccca actagtctac cctccatcat tgttataaaa aacttaggaa    4020
ccaggtccac acagccgcca gcccatcaac gcgtacgtag cgcgcatgag taaaggagaa    4080
gaacttttca ctggagttgt cccaattctt gttgaattag atggtgatgt taatgggcac    4140
aaattttctg tcagtggaga gggtgaaggt gatgcaacat acggaaaact taccctaaaa    4200
tttatttgca ctactggaaa actacctgtt ccatggccaa cacttgtcac tactttcacc    4260
tatggtgttc aatgctttc aagataccca gatcatatga aacggcatga cttttcaag    4320 agtgccatgc ccgaaggtta cgtacaggaa agaactatat ttttcaaaga tgacgggaac    4380
tacaagacac gtgctgaagt caagtttgaa ggtgatacccc ttgttaatag aatcgagtta    4440
aaaggtattg attttaaaga agatggaaac attcttggac acaaattgga atacaactat    4500
aactcacaca atgtatacat catggcagac aaacaaaaga atggaatcag agttaacttc    4560
aaaattagac acaacattga agatggaagc gttcaactag cagaccatta tcaacaaaat    4620
actccaattg gcgatggccc tgtccttta ccagacaacc attacctgtc cacacaatct    4680
gccctttcga aagatcccaa cgaaaagaga gaccacatgg tccttcttga gtttgtaaca    4740
gctgctggga ttacacatgg catggatgaa ctatacaaat agtgagcgcg cagcgctgac    4800
gtctcgcgat gatactagta caacctaaat ccatcataaa aaacttagga gcaaagtgat    4860
tgcctcccaa gttccacaat gacagagatc tacgacttcg acaagtcggc atgggacatc    4920
aaagggtcga tcgctccgat acaacccacc acctacagtg atggcaggct ggtgccccag    4980
gtcagagtca tagatcctgg tctaggcgac aggaaggatg aatgctttat gtacatgttt    5040
ctgctggggg ttgttgagga cagggattcc ctagggcctc caatcgggcg agcatttggg    5100
tccctgccct taggtgttgg cagatccaca gcaaagcccg aaaaactcct caaagaggcc    5160
actgagcttg acatagttgt tagacgtaca gcagggctca atgaaaaact ggtgttctac    5220
aacaacaccc cactaactct cctcacacct tggagaaagg tcctaacaac agggagtgtc    5280
ttcaacgcaa accaagtgtg caatgcggtt aatctgatac cgctcgatac cccgcagagg    5340
ttccgtgttg tttatatgag catcacccgt ctttcggata acgggtatta caccgttcct    5400
agaagaatgc tggaattcag atcggtcaat gcagtggcct tcaacctgct ggtgaccctt    5460
aggattgaca aggcgatagg ccctgggaag atcatcgaca atacagagca acttcctgag    5520
gcaacattta tagtccacat cgggaacttc aggagaaaga agagtgaagt ctactctgcc    5580
gattattgca aaatgaaaat cgaaaagatg ggcctggttt ttgcacttgg tgggataggg    5640
ggcaccagtc ttcacattag aagcacaggc aaaatgagca agactctcaa tgcacaactc    5700
gggttcaaga agacccttatg ttacccgctg atggatatca atgaagacct taatcgatta    5760
ctctggagga gcagatgcaa gatagtaaga atccaggcag ttttgcagcc atcagttcct    5820
caagaattcc gcatttacga cgacgtgatc ataaatgatg accaaggact attcaaagtt    5880
ctgtagaccg tagtgcccag caatgcccga aaacgacccc cctcacaatg acagccagaa    5940
```

```
ggcccggaca aaaaagcccc ctccgaaaga ctccacggac caagcgagag gccagccagc    6000
agccgacggc aagcgcgaac accaggcggc cccagcacag aacagccctg acacaaggcc    6060
accaccagcc accccaatct gcatcctcct cgtgggaccc ccgaggacca accccaagg     6120 ctgcccccga tccaaccac caaccgcatc cccaccaccc ccgggaaaga aaccccagc      6180 aattggaagg cccctccccc tcttcctcaa cacaagaact ccacaaccga accgcacaag    6240
cgaccgaggt gacccaaccg caggcatccg actccctaga cagatcctct ctccccggca    6300
aactaaacaa aacttagggc caaggaacat acacacccaa cagaaccag accccggccc     6360 acggcgccgc gccccaacc cccgacaacc agagggagcc cccaaccaat cccgccggct     6420
cccccggtgc ccacaggcag ggacaccaac ccccgaacag acccagccacc caaccatcga   6480 caatccaaga cgggggggcc ccccaaaaa aagccccca ggggccgaca gccagcaccg      6540
cgaggaagcc cacccacccc acacacgacc acggcaacca aaccagaacc cagaccaccc    6600
tgggccacca gctcccagac tcggccatca ccccgcagaa aggaaaggcc acaacccgcg    6660
caccccagcc ccgatccggc ggggagccac ccaacccgaa ccagcaccca agagcgatcc    6720
ccgaaggacc cccgaaccgc aaaggacatc agtatcccac agcctctcca agtccccgg     6780 tctcctcctc ttctcgaagg gaccaaaaga tcaatccacc acacccgacg acactcaact    6840 ccccaccct aaaggagaca ccgggaatcc cagaatcaag actcatccaa tgtccatcat     6900
gggtctcaag gtgaacgtct ctgccatatt catggcagta ctgttaactc tccaaacacc    6960
caccggtcaa atccattggg gcaatctctc taagataggg gtggtaggaa taggaagtgc    7020
aagctacaaa gttatgactc gttccagcca tcaatcatta gtcataaaat taatgcccaa    7080
tataactctc ctcaataact gcacgagggt agagattgca gaatacagga gactactgag    7140 aacagtttg gaaccaatta gagatgcact taatgcaatg acccagaata taagaccggt     7200
tcagagtgta gcttcaagta ggagacacaa gagatttgcg ggagtagtcc tggcaggtgc    7260
ggccctaggc gttgccacag ctgctcagat aacggccggc attgcacttc accagtccat    7320
gctgaactct caagccatcg acaatctgag agcgagcctg gaaactacta atcaggcaat    7380
tgaggcaatc agacaagcag ggcaggagat gatattggct gttcagggtg tccaagacta    7440
catcaataat gagctgatac cgtctatgaa ccaactatct tgtgatttaa tcggccagaa    7500
gctcgggctc aaattgctca gatactatac agaaatcctg tcattatttg ccccagtttt    7560
acgggacccc atatctgcgg agatatctat ccaggctttg agctatgcgc ttggaggaga    7620
catcaataag gtgttagaaa agctcggata cagtggaggt gatttactgg gcatcttaga    7680
gagcagagga ataaaggccc ggataactca cgtcgacaca gagtcctact tcattgtcct    7740
cagtatagcc tatccgacgc tgtccagat taaggggggtg attgtccacc ggctagaggg    7800
ggtctcgtac aacataggct ctcaagagtg gtataccact gtgcccaagt atgttgcaac    7860
ccaagggtac cttatctcga attttgatga gtcatcgtgt actttcatgc cagagggggac    7920 tgtgtgcagc caaaatgcct tgtacccgat gagtcctctg ctccaagaat gcctccgggg    7980
gtacaccaag tcctgtgctc gtacactcgt atccgggtct tttgggaacc ggttcatttt    8040
atcacaaggg aacctaatag ccaattgtgc atcaatcctt tgcaagtgtt acacaacagg    8100
aacgatcatt aatcaagacc ctgacaagat cctaacatac attgctgccg atcactgccc    8160
ggtagtcgag gtgaacggcg tgaccatcca agtcggagc aggaggtatc cagacgctgt     8220
gtacttgcac agaattgacc tcggtcctcc catatcattg gagaggttgg acgtagggac    8280
```

```
aaatctgggg aatgcaattg ctaagttgga ggatgccaag gaattgttgg agtcatcgga    8340
ccagatattg aggagtatga aaggtttatc gagcactagc atagtctaca tcctgattgc    8400
agtgtgtctt ggagggttga tagggatccc cgctttaata tgttgctgca ggggcgttg     8460 taacaaaaag ggagaacaag ttggtatgtc aagaccaggc ctaaagcctg atcttacggg    8520
aacatcaaaa tcctatgtaa ggtcgctctg atcctctaca actcttgaaa cacaaatgtc    8580
ccacaagtct cctcttcgtc atcaagcaac caccgcaccc agcatcaagc ccacctgaaa    8640
ttatctccgg cttccctctg gccgaacaat atcggtagtt aattaaaact tagggtgcaa    8700
gatcatccac aatgtcacca caacgagacc ggataaatgc cttctacaaa gataaccccc    8760
atcccaaggg aagtaggata gtcattaaca gagaacatct tatgattgat agaccttatg    8820
ttttgctggc tgttctgttt gtcatgtttc tgagcttgat cgggttgcta gccattgcag    8880
gcattagact tcatcgggca gccatctaca ccgcagagat ccataaaagc ctcagcacca    8940
atctagatgt aactaactca atcgagcatc aggtcaagga cgtgctgaca ccactcttca    9000
aaatcatcgg tgatgaagtg ggcctgagga cacctcagag attcactgac ctagtgaaat    9060
tcatctctga caagattaaa ttccttaatc cggataggga gtacgacttc agagatctca    9120
cttggtgtat caacccgcca gagagaatca aattggatta tgatcaatac tgtgcagatg    9180
tggctgctga agagctcatg aatgcattgg tgaactcaac tctactggag accagaacaa    9240
ccaatcagtt cctagctgtc tcaaagggaa actgctcagg gcccactaca atcagaggtc    9300
aattctcaaa catgtcgctg tccctgttag acttgtattt aggtcgaggt tacaatgtgt    9360
catctatagt cactatgaca tcccagggaa tgtatggggg aacttaccta gtggaaaagc    9420
ctaatctgag cagcaaaagg tcagagttgt cacaactgag catgtaccga gtgtttgaag    9480
taggtgttat cagaaatccg ggtttggggg ctccggtgtt ccatatgaca aactatcttg    9540
agcaaccagt cagtaatgat ctcagcaact gtatggtggc tttgggggag ctcaaactcg    9600 cagcccttg tcacggggaa gattctatca caattcccta tcaggatca gggaaggtg     9660 tcagcttcca gctcgtcaag ctaggtgtct ggaaatcccc aaccgacatg caatcctggg    9720
tccccttatc aacggatgat ccagtgatag acaggcttta cctctcatct cacagaggtg    9780
ttatcgctga caatcaagca aaatgggctg tcccgacaac acgaacagat gacaagttgc    9840
gaatggagac atgcttccaa caggcgtgta agggtaaaat ccaagcactc tgcgagaatc    9900
ccgagtgggc accattgaag gataacagga ttccttcata cggggtcttg tctgttgatc    9960
tgagtctgac agttgagctt aaaatcaaaa ttgcttcggg attcgggcca ttgatcacac   10020
acggttcagg gatggaccta tacaaatcca accacaacaa tgtgtattgg ctgactatcc   10080
cgccaatgaa gaacctagcc ttaggtgtaa tcaacacatt ggagtggata ccagattca    10140 aggttagtcc ctacctcttc actgtcccaa ttaaggaagc aggcgaagac tgccatgccc   10200
caacatacct acctgcggag gtggatggtg atgtcaaact cagttccaat ctggtgattc   10260
tacctggtca agatctccaa tatgttttgg caacctacga tacttccagg gttgaacatg   10320
ctgtggttta ttacgtttac agcccaggcc gctcattttc ttactttat ccttttaggt     10380 tgcctataaa gggggtcccc atcgaattac aagtggaatg cttcacatgg gaccaaaaac   10440
tctggtgccg tcacttctgt gtgcttgcgg actcagaatc tggtggacat atcactcact   10500 ctggatggt gggcatggga gtcagctgca cagtcacccg ggaagatgga accaatcgca   10560 gataggctg ctagtgaacc aatcacatga tgtcacccag acatcaggca tacccactag    10620
tgtgaaatag acatcagaat taagaaaaac gtagggtcca agtggttccc cgttatggac   10680
```

```
tcgctatctg tcaaccagat cttataccct gaagttcacc tagatagccc gatagttacc    10740
aataagatag tagccatcct ggagtatgct cgagtccctc acgcttacag cctggaggac    10800
cctacactgt gtcagaacat caagcaccgc ctaaaaaacg gattttccaa ccaaatgatt    10860
ataaacaatg tggaagttgg gaatgtcatc aagtccaagc ttaggagtta ccggcccac     10920 tctcatattc catatccaaa ttgtaatcag gatttattta acatagaaga caaagagtca    10980
acgaggaaga tccgtgaact cctcaaaaag gggaattcgc tgtactccaa agtcagtgat    11040
aaggttttcc aatgcttaag ggacactaac tcacggcttg cctaggctc cgaattgagg     11100 gaggacatca aggagaaagt tattaacttg ggagtttaca tgcacagctc ccagtggttt    11160 gagcccttc tgttttggtt tacagtcaag actgagatga ggtcagtgat taaatcacaa     11220
acccatactt gccataggag gagacacaca cctgtattct tcactggtag ttcagttgag    11280
ttgctaatct ctcgtgacct tgttgctata atcagtaaag agtctcaaca tgtatattac    11340
ctgacatttg aactggtttt gatgtattgt gatgtcatag aggggaggtt aatgacagag    11400
accgctatga ctattgatgc taggtataca gagcttctag gaagagtcag atacatgtgg    11460
aaactgatag atggtttctt ccctgcactc gggaatccaa cttatcaaat tgtagcaatg    11520
ctggagcctc tttcacttgc ttacctgcag ctgagggata taacagtaga actcagaggt    11580
gctttcctta accactgctt tactgaaata catgatgttc ttgaccaaaa cgggttttct    11640
gatgaaggta cttatcatga gttaattgaa gctctagatt acatttttcat aactgatgac    11700 atacatctga caggggagat tttctcattt tcagaagtt tcggccaccc cagacttgaa     11760
gcagtaacgg ctgctgaaaa tgttaggaaa tacatgaatc agcctaaagt cattgtgtat    11820
gagactctga tgaaaggtca tgccatattt tgtggaatca taatcaacgg ctatcgtgac    11880
aggcacggag gcagttggcc accgctgacc ctcccctgc atgctgcaga cacaatccgg     11940
aatgctcaag cttcaggtga agggttaaca catgagcagt gcgttgataa ctggaaatct    12000
tttgctggag tgaaatttgg ctgctttatg cctcttagcc tggatagtga tctgacaatg    12060
tacctaaagg acaaggcact tgctgctctc caaagggaat gggattcagt ttacccgaaa    12120
gagttcctgc gttacgaccc tcccaaggga accgggtcac ggaggcttgt agatgttttc    12180
cttaatgatt cgagctttga cccatatgat gtgataatgt atgttgtaag tggagcttac    12240
ctccatgacc ctgagttcaa cctgtcttac agcctgaaag aaaaggagat caaggaaaca    12300
ggtagacttt ttgctaaaat gacttacaaa atgagggcat gccaagtgat tgctgaaaat    12360
ctaatctcaa acgggattgg caaatatttt aaggacaatg ggatggccaa ggatgagcac    12420
gatttgacta aggcactcca cactctagct gtctcaggag tccccaaaga tctcaaagaa    12480
agtcacaggg ggggccagt cttaaaaacc tactcccgaa gcccagtcca cacaagtacc     12540
aggaacgtga gagcagcaaa agggtttata gggttccctc aagtaattcg gcaggaccaa    12600
gacactgatc atccggagaa tatggaagct tacgagacag tcagtgcatt tatcacgact    12660
gatctcaaga agtactgcct taattggaga tatgagacca tcagcttgtt tgcacagagg    12720
ctaaatgaga tttacggatt gccctcattt ttccagtggc tgcataagag gcttgagacc    12780
tctgtcctgt atgtaagtga ccctcattgc cccccgacc ttgacgccca tatcccgtta     12840
tataaagtcc ccaatgatca aatcttcatt aagtacccta tgggaggtat agaagggtat    12900
tgtcagaagc tgtggaccat cagcaccatt ccctatctat acctggctgc ttatgagagc    12960
ggagtaagga ttgcttcgtt agtgcaaggg gacaatcaga ccatagccgt aacaaaaagg    13020
```

```
gtacccagca catggcccta caaccttaag aaacgggaag ctgctagagt aactagagat    13080
tactttgtaa ttcttaggca aaggctacat gatattggcc atcacctcaa ggcaaatgag    13140
acaattgttt catcacattt ttttgtctat tcaaaaggaa tatattatga tgggctactt    13200
gtgtcccaat cactcaagag catcgcaaga tgtgtattct ggtcagagac tatagttgat    13260
gaaacaaggg cagcatgcag taatattgct acaacaatgg ctaaaagcat cgagagaggt    13320
tatgaccgtt accttgcata ttccctgaac gtcctaaaag tgatacagca aattctgatc    13380
tctcttggct tcacaatcaa ttcaaccatg acccgggatg tagtcatacc cctcctcaca    13440
aacaacgacc tcttaataag gatggcactg ttgcccgctc ctattggggg gatgaattat    13500
ctgaatatga gcaggctgtt tgtcagaaac atcggtgatc cagtaacatc atcaattgct    13560
gatctcaaga gaatgattct cgcctcacta atgcctgaag agaccctcca tcaagtaatg    13620
acacaacaac cgggggactc ttcattccta gactgggcta gcgacccttta ctcagcaaat    13680 cttgtatgtg tccagagcat cactagactc ctcaagaaca taactgcaag gtttgtcctg    13740
atccatagtc caaacccaat gttaaaagga ttattccatg atgacagtaa agaagaggac    13800
gagggactgg cggcattcct catggacagg catattatag tacctagggc agctcatgaa    13860
atcctggatc atagtgtcac aggggcaaga gagtctattg caggcatgct ggataccaca    13920
aaaggcttga ttcgagccag catgaggaag gggggttaa cctctcgagt gataaccaga    13980
ttgtccaatt atgactatga acaattcaga gcagggatgg tgctattgac aggaagaaag    14040
agaaatgtcc tcattgacaa agagtcatgt tcagtgcagc tggcgagagc tctaagaagc    14100
catatgtggg cgaggctagc tcgaggacgg cctatttacg gccttgaggt ccctgatgta    14160
ctagaatcta tgcgaggcca ccttattcgg cgtcatgaga catgtgtcat ctgcgagtgt    14220
ggatcagtca actacggatg gtttttgtc ccctcgggtt gccaactgga tgatattgac    14280
aaggaaacat catccttgag agtcccatat attggttcta ccactgatga gagaacagac    14340
atgaagcttg ccttcgtaag agccccaagt cgatccttgc gatctgctgt tagaatagca    14400
acagtgtact catgggctta cggtgatgat gatagctctt ggaacgaagc ctggttgttg    14460
gctaggcaaa gggccaatgt gagcctggag gagctaaggg tgatcactcc catctcaact    14520
tcgactaatt tagcgcatag gttgagggat cgtagcactc aagtgaaata ctcaggtaca    14580
tcccttgtcc gagtggcgag gtataccaca atctccaacg acaatctctc atttgtcata    14640
tcagataaga aggttgatac taactttata taccaacaag gaatgctcct agggttgggt    14700
gttttagaaa cattgtttcg actcgagaaa gataccggat catctaacac ggtattacat    14760
cttcacgtcg aaacagattg ttgcgtgatc ccgatgatag atcatcccag gataccccagc    14820 tcccgcaagc tagagctgag ggcagagcta tgtaccaacc cattgatata tgataatgca    14880
cctttaattg acagagatgc aacaaggcta tacacccaga gccataggag gcaccttgtg    14940
gaatttgtta catggtccac accccaacta tatcacatt tagctaagtc cacagcacta    15000
tctatgattg acctggtaac aaaatttgag aaggaccata tgaatgaaat ttcagctctc    15060 atagggatg acgatatcaa tagtttcata actgagtttc tgctcataga gccaagatta    15120
ttcactatct acttgggcca gtgtgcggcc atcaattggg catttgatgt acattatcat    15180
agaccatcag ggaaatatca gatgggtgag ctgttgtcat cgttcctttc tagaatgagc    15240
aaaggagtgt taaggtgct tgtcaatgct ctaagccacc caaagatcta caagaaattc    15300
tggcattgtg gtattataga gcctatccat ggtccttcac ttgatgctca aaacttgcac    15360
acaactgtgt gcaacatggt ttacacatgc tatatgacct acctcgacct gttgttgaat    15420
```

-continued

```
gaagagttag aagagttcac atttctcttg tgtgaaagcg acgaggatgt agtaccggac    15480
agattcgaca acatccaggc aaaacactta tgtgttctgg cagatttgta ctgtcaacca    15540
gggacctgcc caccaattcg aggtctaaga ccggtagaga aatgtgcagt tctaaccgac    15600
catatcaagg cagaggctat gttatctcca gcaggatctt cgtggaacat aaatccaatt    15660
attgtagacc attactcatg ctctctgact tatctccggc gaggatcgat caaacagata    15720
agattgagag ttgatccagg attcattttc gacgccctcg ctgaggtaaa tgtcagtcag    15780
ccaaagatcg gcagcaacaa catctcaaat atgagcatca aggctttcag accccacac     15840 gatgatgttg caaaattgct caaagatatc aacacaagca agcacaatct tcccatttca    15900
gggggcaatc tcgccaatta tgaaatccat gctttccgca gaatcgggtt gaactcatct    15960
gcttgctaca aagctgttga gatatcaaca ttaattagga gatgccttga gccaggggag    16020
gacggcttgt tcttgggtga gggatcgggt tctatgttga tcacttataa ggagatactt    16080
aaactaaaca agtgcttcta taatagtggg gtttccgcca attctagatc tggtcaaagg    16140
gaattagcac cctatccctc cgaagttggc cttgtcgaac acagaatggg agtaggtaat    16200
attgtcaaag tgctctttaa cgggaggccc gaagtcacgt gggtaggcag tgtagattgc    16260
ttcaatttca tagttagtaa tatccctacc tctagtgtgg ggtttatcca ttcagatata    16320
gagaccttgc ctgacaaaga tactatagag aagctagagg aattggcagc catcttatcg    16380
atggctctgc tcctgggcaa aataggatca atactggtga ttaagcttat gcctttcagc    16440
ggggattttg ttcagggatt tataagttat gtagggtctc attatagaga agtgaacctt    16500
gtataccctg atacagcaa cttcatatct actgaatctt atttggttat gacagatctc     16560
aaggctaacc ggctaatgaa tcctgaaaag attaagcagc agataattga atcatctgtg    16620
aggacttcac ctggacttat aggtcacatc ctatccatta agcaactaag ctgcatacaa    16680
gcaattgtgg gagacgcagt tagtagaggt gatatcaatc ctactctgaa aaaacttaca    16740
cctatagagc aggtgctgat caattgcggg ttggcaatta acggacctaa gctgtgcaaa    16800
gaattgatcc accatgatgt tgcctcaggg caagatggat tgcttaattc tatactcatc    16860
ctctacaggg agttggcaag attcaaagac aaccaaagaa gtcaacaagg gatgttccac    16920
gcttaccccg tattggtaag tagcaggcaa cgagaactta tatctaggat cacccgcaaa    16980 ttttggggggc acattcttct ttactccggg aacagaaagt tgataaataa gtttatccag    17040
aatctcaagt ccggctatct gatactagac ttacaccaga atatcttcgt taagaatcta    17100
tccaagtcag agaaacagat tattatgacg gggggtttga acgtgagtg ggttttttaag    17160 gtaacagtca aggagaccaa agaatggtat aagttagtcg gatacagtgc cctgattaag    17220
gactaattgg ttgaactccg gaaccctaat cctgccctag gtggttaggc attatttgca    17280
atatattaaa gaaaactttg aaaatacgaa gtttctattc ccagctttgt ctggtggccg    17340
gcatggtccc agcctcctcg ctggcgccgg ctgggcaaca ttccgagggg accgtccct     17400 cggtaatggc gaatgggacg cggccgatcc ggctgctaac aaagcccgaa aggaagctga    17460
gttggctgct gccaccgctg agcaataact agcataaccc cttggggcct ctaaacgggt    17520
cttgaggggt ttttgctga aaggaggaac tatatccgga tgcggccgca ggtacccagc     17580
ttttgttccc tttagtgagg gttaatttcg agcttggcgt aatcatggtc atagctgttt    17640
cctgtgtgaa attgttatcc gctcacaatt ccacacaaca tacgagccgg aagcataaag    17700
tgtaaagcct ggggtgccta atgagtgagc taactcacat taattgcgtt gcgctcactg    17760
```

```
cccgctttcc agtcgggaaa cctgtcgtgc cagctgcatt aatgaatcgg ccaacgcgcg     17820
gggagaggcg gtttgcgtat tgggcgctct tccgcttcct cgctcactga ctcgctgcgc     17880
tcggtcgttc ggctgcggcg agcggtatca gctcactcaa aggcggtaat acggttatcc     17940
acagaatcag gggataacgc aggaaagaac atgtgagcaa aaggccagca aaaggccagg     18000
aaccgtaaaa aggccgcgtt gctggcgttt ttccataggc tccgcccccc tgacgagcat     18060
cacaaaaatc gacgctcaag tcagaggtgg cgaaacccga caggactata agataccagg     18120
cgtttccccc ctggaagctc cctcgtgcgc tctcctgttc cgaccctgcc gcttaccgga     18180
tacctgtccg cctttctccc ttcgggaagc gtggcgcttt ctcatagctc acgctgtagg     18240
tatctcagtt cggtgtaggt cgttcgctcc aagctgggct gtgtgcacga accccccgtt     18300
cagcccgacc gctgcgcctt atccggtaac tatcgtcttg agtccaaccc ggtaagacac     18360
gacttatcgc cactggcagc agccactggt aacaggatta gcagagcgag gtatgtaggc     18420
ggtgctacag agttcttgaa gtggtggcct aactacggct acactagaag gacagtattt     18480
ggtatctgcg ctctgctgaa gccagttacc ttcggaaaaa gagttggtag ctcttgatcc     18540
ggcaaacaaa ccaccgctgg tagcggtggt ttttttgttt gcaagcagca gattacgcgc     18600
agaaaaaaag gatctcaaga agatcctttg atcttttcta cggggtctga cgctcagtgg     18660
aacgaaaact cacgttaagg gattttggtc atgagattat caaaaaggat cttcacctag     18720
atccttttaa attaaaaatg aagttttaaa tcaatctaaa gtatatatga gtaaacttgg     18780
tctgacagtt accaatgctt aatcagtgag gcacctatct cagcgatctg tctatttcgt     18840
tcatccatag ttgcctgact ccccgtcgtg tagataacta cgatacggga gggcttacca     18900
tctggcccca gtgctgcaat gataccgcga gacccacgct caccggctcc agatttatca     18960
gcaataaacc agccagccgg aagggccgag cgcagaagtg gtcctgcaac tttatccgcc     19020
tccatccagt ctattaattg ttgccgggaa gctagagtaa gtagttcgcc agttaatagt     19080
ttgcgcaacg ttgttgccat tgctacaggc atcgtggtgt cacgctcgtc gtttggtatg     19140
gcttcattca gctccggttc ccaacgatca aggcgagtta catgatcccc catgttgtgc     19200
aaaaaagcgg ttagctcctt cggtcctccg atcgttgtca gaagtaagtt ggccgcagtg     19260
ttatcactca tggttatggc agcactgcat aattctctta ctgtcatgcc atccgtaaga     19320
tgcttttctg tgactggtga gtactcaacc aagtcattct gagaatagtg tatgcggcga     19380
ccgagttgct cttgcccggc gtcaatacgg gataataccg cgccacatag cagaacttta     19440
aaagtgctca tcattggaaa acgttcttcg ggcgaaaac tctcaaggat cttaccgctg     19500
ttgagatcca gttcgatgta acccactcgt gcacccaact gatcttcagc atcttttact     19560
ttcaccagcg tttctgggtg agcaaaaaca ggaaggcaaa atgccgcaaa aaagggaata     19620
agggcgacac ggaaatgttg aatactcata ctcttccttt ttcaatatta ttgaagcatt     19680
tatcagggtt attgtctcat gagcggatac atatttgaat gtatttagaa aaataaacaa     19740
atagggggttc cgcgcacatt tccccgaaaa gtgc                                19774
```

<210> SEQ ID NO 2
<211> LENGTH: 19774
<212> TYPE: DNA
<213> ORGANISM: Human Papilloma Virus

<400> SEQUENCE: 2

```
cacctaaatt gtaagcgtta atattttgtt aaaattcgcg ttaaattttt gttaaatcag        60
ctcatttttt aaccaatagg ccgaaatcgg caaaatccct tataaatcaa agaatagac        120
```

```
cgagatagggt tgagtgttgt tccagtttga acaagagtcc actattaaag aacgtggac       180 ctccaacgtc aaagggcgaa aaaccgtcta tcagggcgat ggcccactac gtgaaccatc       240
accctaatca gttttttgg ggtcgaggtg ccgtaaagca ctaaatcgga accctaaagg        300
gagcccccga tttagagctt gacggggaaa gccggccatt taggccatag ggcgctggca       360
agtgtagcgg tcacgctgcg cgtaaccacc acacccgccg cgcttaatgc gccgctacag       420
ggcgcgtccc attcgccatt caggctgcgc aactgttggg aagggcgatc ggtgcgggcc       480
tcttcgctat tacgccagct ggcgaaaggg ggatgtgctg caaggcgatt aagttgggta       540
acgccagggt tttcccagtc acgacgttgt aaaacgacgg ccagtgaatt gtaatacgac       600
tcactataac caaacaaagt tgggtaagga tagttcaatc aatgatcatc ttctagtgca       660
cttaggattc aagatcctat tatcagggac aagagcagga ttagggatat ctgagatggc       720 cacacttttta aggagcttag cattgttcaa agaaacaag acaaaccac ccattacatc        780 aggatccggt ggagccatca gaggaatcaa acacattatt atagtaccaa tccctggaga       840
ttcctcaatt accactcgat ccagacttct ggaccggttg gtcaggttaa ttggaaaccc       900
ggatgtgagc gggcccaaac taacaggggc actaataggt atattatcct tatttgtgga      960
gtctccaggt caattgattc agaggatcac cgatgaccct gacgttagca taaggctgtt      1020
agaggttgtc cagagtgacc agtcacaatc tggccttacc ttcgcatcaa gaggtaccaa      1080
catggaggat gaggcggacc aatacttttc acatgatgat ccaattagta gtgatcaatc      1140
caggttcgga tggttcgaga acaaggaaat ctcagatatt gaagtgcaag accctgaggg      1200
attcaacatg attctgggta ccatcctagc ccaaatttgg gtcttgctcg caaaggcggt      1260
tacggcccca gacacggcag ctgattcgga gctaagaagg tggataaagt acacccaaca      1320
aagaagggta gttggtgaat ttagattgga gagaaaatgg ttggatgtgg tgaggaacag      1380
gattgccgag gacctctcct tacgccgatt catggtcgct ctaatcctgg atatcaagag      1440
aacacccgga aacaaaccca ggattgctga aatgatatgt gacattgata catatatcgt      1500
agaggcagga ttagccagtt ttatcctgac tattaagttt gggatagaaa ctatgtatcc      1560
tgctcttgga ctgcatgaat ttgctggtga gttatccaca cttgagtcct tgatgaacct      1620
ttaccagcaa atgggggaaa ctgcacccta catggtaatc ctggagaact caattcagaa      1680
caagttcagt gcaggatcat accctctgct ctggagctat gccatgggag taggagtgga      1740
acttgaaaac tccatggggg gtttgaactt tggccgatct tactttgatc agcatatttt     1800
tagattaggg caagagatgg taaggaggtc agctggaaag gtcagttcca cattggcatc      1860
tgaactcggt atcactgccg aggatgcaag gcttgtttca gagattgcaa tgcatactac      1920
tgaggacaag atcagtagag cggttggacc cagacaagcc caagtatcat ttctacacgg     1980
tgatcaaagt gagaatgagc taccgagatt gggggggcaag gaagatagga gggtcaaaca     2040
gagtcgagga gaagccaggg agagctacag agaaaccggg cccagcagag caagtgatgc      2100
gagagctgcc catcttccaa ccggcacacc cctagacatt gacactgcat cggagtccag      2160
ccaagatccg caggacagtc gaaggtcagc tgacgccctg cttaggctgc aagccatggc      2220
aggaatctcg gaagaacaag gctcagacac ggacaccct atagtgtaca atgacagaaa       2280
tcttctagac taggtgcgag aggccgaggg ccagaacaac atccgcctac cctccatcat      2340
tgttataaaa aacttaggaa ccaggtccac acagccgcca gcccatcaac catccactcc      2400
cacgattgga gccaatggta aagagcagg cacgccatgt caaaaacgga ctggaatgca      2460
```

```
tccgggctct caaggccgag cccatcggct cactggccat cgaggaagct atggcagcat    2520
ggtcagaaat atcagacaac ccaggacagg agcgagccac ctgcagggaa gagaaggcag    2580
gcagttcggg tctcagaaaa ccatgcctct cagcaattgg atcaactgaa ggcggtgcac    2640
ctcgcatccg cggtcaggga cctggagaga gcgatgacga cgctgaaact ttgggaatcc    2700
ccccaagaaa tctccaggca tcaagcactg ggttacagtg ttattacgtt tatgatcaca    2760
gcggtgaagc ggttaaggga atccaagatg ctgactctat catggttcaa tcaggccttg    2820
atggtgatag caccctctca ggaggagaca atgaatctga aaacagcgat gtggatattg    2880
gcgaacctga taccgaggga tatgctatca ctgaccgggg atctgctccc atctctatgg    2940
ggttcagggc ttctgatgtt gaaactgcag aaggagggga gatccacgag ctcctgagac    3000
tccaatccag aggcaacaac tttccgaagc ttgggaaaac tctcaatgtt cctccgcccc    3060
cggaccccgg tagggccagc acttccggga cacccattaa aaagggcaca gacgcgagat    3120
tagcctcatt tggaacggag atcgcgtctt tattgacagg tggtgcaacc caatgtgctc    3180
gaaagtcacc ctcggaacca tcaggccag gtgcacctgc ggggaatgtc cccgagtgtg    3240
tgagcaatgc cgcactgata caggagtgga caccgaatc tggtaccaca atctccccga    3300
gatcccagaa taatgaagaa gggggagact attatgatga tgagctgttc tctgatgtcc    3360
aagatattaa acagccttg gccaaaatac acgaggataa tcagaagata atctccaagc    3420
tagaatcact gctgttattg aagggagaag ttgagtcaat taagaagcag atcaacaggc    3480
aaaatatcag catatccacc ctggaaggac acctctcaag catcatgatc gccattcctg    3540
gacttgggaa ggatcccaac gaccccactg cagatgtcga atcaatccc gacttgaaac    3600 ccatcatagg cagagattca ggccgagcac tggccgaagt tctcaagaaa cccgttgcca    3660
gccgacaact ccaaggaatg acaaatggac ggaccagttc cagaggacag ctgctgaagg    3720
aatttcagct aaagccgatc gggaaaaaga tgagctcagc cgtcgggttt gttcctgaca    3780
ccggccctgc atcacgcagt gtaatccgct ccattataaa atccagccgg ctagaggagg    3840
atcggaagcg ttacctgatg actctccttg atgatatcaa aggagccaat gatcttgcca    3900
agttccacca gatgctgatg aagataataa tgaagtagct acagctcaac ttacctgcca    3960
accccatgcc agtcgaccca actagtacaa cctaaatcca tcataaaaaa cttaggagca    4020
aagtgattgc ctcccaagtt ccacaatgac agagatctac gacttcgaca agtcggcatg    4080
ggacatcaaa gggtcgatcg ctccgataca acccaccacc tacagtgatg gcaggctggt    4140
gccccaggtc agagtcatag atcctggtct aggcgacagg aaggatgaat gctttatgta    4200
catgtttctg ctgggggttg ttgaggacag ggattcccta gggcctccaa tcgggcgagc    4260
atttgggtcc ctgcccttag gtgttggcag atccacagca aagcccgaaa aactcctcaa    4320
agaggccact gagcttgaca tagttgttag acgtacagca gggctcaatg aaaaactggt    4380
gttctacaac aacaccccac taactctcct cacaccttgg agaaaggtcc taacaacagg    4440
gagtgtcttc aacgcaaacc aagtgtgcaa tgcggttaat ctgataccgc tcgatacccc    4500
gcagaggttc cgtgttgttt atatgagcat cacccgtctt tcggataacg ggtattacac    4560
cgttcctaga agaatgctgg aattcagatc ggtcaatgca gtggccttca acctgctggt    4620
gacccttagg attgacaagg cgataggccc tgggaagatc atcgacaata cagagcaact    4680
tcctgaggca acatttatag tccacatcgg gaacttcagg agaaagaaga gtgaagtcta    4740
ctctgccgat tattgcaaaa tgaaaatcga aaagatgggc ctggttttgg cacttggtgg    4800 gataggggc accagtcttc acattagaag cacaggcaaa atgagcaaga ctctcaatgc    4860
```

```
acaactcggg ttcaagaaga ccttatgtta cccgctgatg gatatcaatg aagaccttaa    4920
tcgattactc tggaggagca gatgcaagat agtaagaatc caggcagttt tgcagccatc    4980
agttcctcaa gaattccgca tttacgacga cgtgatcata aatgatgacc aaggactatt    5040
caaagttctg tagaccgtag tgcccagcaa tgcccgaaaa cgaccccct cacaatgaca     5100 gccagaaggc ccggacaaaa aagcccctc cgaaagactc cacggaccaa gcgagaggcc     5160
agccagcagc cgacggcaag cgcgaacacc aggcggcccc agcacagaac agccctgaca    5220
caaggccacc accagccacc ccaatctgca tcctcctcgt gggaccccg aggaccaacc     5280 cccaaggctg cccccgatcc aaaccaccaa ccgcatcccc accaccccg ggaaagaaac     5340 ccccagcaat tggaaggccc ctcccctct tcctcaacac aagaactcca caaccgaacc     5400
gcacaagcga ccgaggtgac ccaaccgcag gcatccgact ccctagacag atcctctctc    5460
cccggcaaac taaacaaaac ttagggccaa ggaacataca cacccaacag aacccagacc    5520
ccggcccacg gcgccgcgcc cccaaccccc gacaaccaga gggagccccc aaccaatccc    5580
gccggctccc ccggtgccca caggcaggga caccaaccc cgaacagacc cagcacccaa    5640
ccatcgacaa tccaagacgg gggggccccc ccaaaaaaaa gccccagggg ccgacagcc    5700 agcaccgcga ggaagcccac ccaccccaca cacgaccacg gcaaccaaac cagaacccag    5760
accaccctgg gccaccagct cccagactcg gccatcaccc cgcagaaagg aaaggccaca    5820
acccgcgcac cccagccccg atccggcggg gagccaccca acccgaacca gcacccaaga    5880 gcgatcccg aaggaccccc gaaccgcaaa ggacatcagt atcccacagc ctctccaagt    5940
cccccggtct cctcctcttc tcgaagggac caaaagatca atccaccaca cccgacgaca    6000
ctcaactccc caccccctaaa ggagacaccg ggaatcccag aatcaagact catccaatgt    6060
ccatcatggg tctcaaggtg aacgtctctg ccatattcat ggcagtactg ttaactctcc    6120
aaacacccac cggtcaaatc cattggggca atctctctaa gatagggtg gtaggaatag    6180 gaagtgcaag ctacaaagtt atgactcgtt ccagccatca atcattagtc ataaaattaa    6240
tgcccaatat aactctcctc aataactgca cgagggtaga gattgcagaa tacaggagac    6300
tactgagaac agttttggaa ccaattagag atgcacttaa tgcaatgacc cagaatataa    6360
gaccggttca gagtgtagct tcaagtagga gacacaagag atttgcggga gtagtcctgg    6420
caggtgcggc cctaggcgtt gccacagctg ctcagataac ggccggcatt gcacttcacc    6480
agtccatgct gaactctcaa gccatcgaca atctgagagc gagcctggaa actactaatc    6540
aggcaattga ggcaatcaga caagcagggc aggagatgat attggctgtt cagggtgtcc    6600
aagactacat caataatgag ctgataccgt ctatgaacca actatcttgt gatttaatcg    6660
gccagaagct cgggctcaaa ttgctcagat actatacaga aatcctgtca ttatttggcc    6720
ccagtttacg ggaccccata tctgcggaga tatctatcca ggctttgagc tatgcgcttg    6780
gaggagacat caataaggtg ttagaaaagc tcggatacag tggaggtgat ttactgggca    6840
tcttagagag cagaggaata aaggcccgga taactcacgt cgacacagag tcctacttca    6900
ttgtcctcag tatagcctat ccgacgctgt ccgagattaa gggggtgatt gtccaccggc    6960 tagaggggt ctcgtacaac ataggctctc aagagtggta taccactgtg cccaagtatg    7020
ttgcaaccca agggtacctt atctcgaatt ttgatgagtc atcgtgtact ttcatgccag    7080 agggggactgt gtgcagccaa aatgccttgt acccgatgag tcctctgctc caagaatgcc    7140 tccggggta caccaagtcc tgtgctcgta cactcgtatc cgggtctttt gggaaccggt    7200
```

```
tcattttatc acaagggaac ctaatagcca attgtgcatc aatcctttgc aagtgttaca    7260
caacaggaac gatcattaat caagaccctg acaagatcct aacatacatt gctgccgatc    7320
actgcccggt agtcgaggtg aacggcgtga ccatccaagt cgggagcagg aggtatccag    7380
acgctgtgta cttgcacaga attgacctcg gtcctcccat atcattggag aggttggacg    7440
tagggacaaa tctggggaat gcaattgcta agttggagga tgccaaggaa ttgttggagt    7500
catcggacca gatattgagg agtatgaaag gtttatcgag cactagcata gtctacatcc    7560
tgattgcagt gtgtcttgga gggttgatag ggatccccgc tttaatatgt tgctgcaggg    7620
ggcgttgtaa caaaaaggga gaacaagttg gtatgtcaag accaggccta agcctgatc    7680 ttacgggaac atcaaaatcc tatgtaaggt cgctctgatc ctctacaact cttgaaacac    7740
aaatgtccca caagtctcct cttcgtcatc aagcaaccac cgcacccagc atcaagccca    7800
cctgaaatta tctccggctt ccctctggcc gaacaatatc ggtagttaat taaaacttag    7860
ggtgcaagat catccacaat gtcaccacaa cgagaccgga taaatgcctt ctacaaagat    7920
aacccccatc ccaagggaag taggatagtc attaacagaa acatcttat gattgataga    7980 ccttatgttt tgctggctgt tctgtttgtc atgtttctga gcttgatcgg gttgctagcc    8040
attgcaggca tttagacttca tcgggcagcc atctacaccg cagagatcca taaaagcctc    8100
agcaccaatc tagatgtaac taactcaatc gagcatcagg tcaaggacgt gctgacacca    8160
ctcttcaaaa tcatcggtga tgaagtgggc ctgaggacac ctcagagatt cactgaccta    8220
gtgaaattca tctctgacaa gattaaattc cttaatccgg atagggagta cgacttcaga    8280
gatctcactt ggtgtatcaa cccgccagag agaatcaaat tggattatga tcaatactgt    8340
gcagatgtgg ctgctgaaga gctcatgaat gcattggtga actcaactct actggagacc    8400
agaacaacca atcagttcct agctgtctca aagggaaact gctcagggcc cactacaatc    8460
agaggtcaat tctcaaacat gtcgctgtcc ctgttagact tgtatttagg tcgaggttac    8520
aatgtgtcat ctatagtcac tatgacatcc caggggaatgt atgggggaac ttacctagtg    8580
gaaaagccta atctgagcag caaaaggtca gagttgtcac aactgagcat gtaccgagtg    8640
tttgaagtag gtgttatcag aaatccgggt ttggggggctc cggtgttcca tatgacaaac    8700
tatcttgagc aaccagtcag taatgatctc agcaactgta tggtggcttt ggggggagctc    8760 aaactcgcag ccctttgtca cggggaagat tctatcacaa ttccctatca gggatcaggg    8820
aaaggtgtca gcttccagct cgtcaagcta ggtgtctgga atccccaac cgacatgcaa    8880 tcctgggtcc ccttatcaac ggatgatcca gtgatagaca ggctttacct ctcatctcac    8940
agaggtgtta tcgctgacaa tcaagcaaaa tgggctgtcc cgacaacacg aacagatgac    9000
aagttgcgaa tggagacatg cttccaacag gcgtgtaagg gtaaaatcca agcactctgc    9060
gagaatcccg agtgggcacc attgaaggat aacaggattc cttcatacgg ggtcttgtct    9120
gttgatctga gtctgacagt tgagcttaaa atcaaaattg cttcgggatt cgggccattg    9180
atcacacacg gttcagggat ggacctatac aaatccaacc acaacaatgt gtattggctg    9240
actatcccgc caatgaagaa cctagcctta ggtgtaatca acacattgga gtggataccg    9300
agattcaagg ttagtcccta cctcttcact gtcccaatta aggaagcagg cgaagactgc    9360
catgccccaa cataacctacc tgcggaggtg gatggtgatg tcaaactcag ttccaatctg    9420
gtgattctac ctggtcaaga tctccaatat gttttggcaa cctacgatac ttccagggtt    9480
gaacatgctg tggtttatta cgtttacagc ccaggccgct cattttctta cttttatcct    9540
tttaggttgc ctataaaggg ggtccccatc gaattacaag tggaatgctt cacatgggac    9600
```

```
caaaaactct ggtgccgtca cttctgtgtg cttgcggact cagaatctgg tggacatatc   9660
actcactctg ggatggtggg catgggagtc agctgcacag tcacccggga agatggaacc   9720
aatcgcagat agggctgcta gtgaaccaat cacatgatgt cacccagaca tcaggcatac   9780
ccactagtct accctccatc attgttataa aaaacttagg aaccaggtcc acacagccgc   9840
cagcccatca acgcgtacgt agcgcgcatg agtaaaggag aagaactttt cactggagtt   9900
gtcccaattc ttgttgaatt agatggtgat gttaatgggc acaaattttc tgtcagtgga   9960
gagggtgaag gtgatgcaac atacggaaaa cttaccctta aatttatttg cactactgga  10020
aaactacctg ttccatggcc aacacttgtc actactttca cctatggtgt caatgctttt  10080
tcaagatacc cagatcatat gaaacggcat gactttttca gagtgccat gcccgaaggt  10140 tacgtacagg aaagaactat attttttcaaa gatgacggga actacaagac acgtgctgaa  10200
gtcaagtttg aaggtgatac ccttgttaat agaatcgagt taaaaggtat tgattttaaa  10260
gaagatggaa acattcttgg acacaaattg gaatacaact ataactcaca caatgtatac  10320
atcatggcag acaaacaaaa gaatggaatc agagttaact tcaaaattag acacaacatt  10380
gaagatggaa gcgttcaact agcagaccat tatcaacaaa atactccaat tggcgatggc  10440
cctgtccttt taccagacaa ccattacctg tccacacaat ctgcccttt gaaagatccc  10500 aacgaaaaga gagaccacat ggtccttctt gagtttgtaa cagctgctgg gattacacat  10560
ggcatggatg aactatacaa atagtgagcg cgcagcgctg acgtctcgcg atgatactag  10620
tgtgaaatag acatcagaat taagaaaaac gtagggtcca agtggttccc cgttatggac  10680
tcgctatctg tcaaccagat cttatacct gaagttcacc tagatagccc gatagttacc  10740
aataagatag tagccatcct ggagtatgct cgagtccctc acgcttacag cctggaggac  10800
cctacactgt gtcagaacat caagcaccgc ctaaaaaacg gattttccaa ccaaatgatt  10860
ataaacaatg tggaagttgg gaatgtcatc aagtccaagc ttaggagtta tccggcccac  10920
tctcatattc catatccaaa ttgtaatcag gatttattta acatagaaga caaagagtca  10980
acgaggaaga tccgtgaact cctcaaaaag gggaattcgc tgtactccaa agtcagtgat  11040
aaggttttcc aatgcttaag ggacactaac tcacggcttg gcctaggctc cgaattgagg  11100
gaggacatca aggagaaagt tattaacttg ggagtttaca tgcacagctc ccagtggttt  11160 gagcccttc tgttttggtt tacagtcaag actgagatga ggtcagtgat taaatcacaa  11220
acccatactt gccataggag gagacacaca cctgtattct tcactggtag ttcagttgag  11280
ttgctaatct ctcgtgacct tgttgctata atcagtaaag agtctcaaca tgtatattac  11340
ctgacatttg aactggtttt gatgtattgt gatgtcatag aggggaggtt aatgacagag  11400
accgctatga ctattgatgc taggtataca gagcttctag gaagagtcag atacatgtgg  11460
aaactgatag atggtttctt ccctgcactc gggaatccaa cttatcaaat tgtagcaatg  11520
ctggagcctc tttcacttgc ttacctgcag ctgagggata taacagtaga actcagaggt  11580
gctttcctta accactgctt tactgaaata catgatgttc ttgaccaaaa cgggttttct  11640
gatgaaggta cttatcatga gttaattgaa gctctagatt acattttcat aactgatgac  11700
atacatctga caggggagat tttctcattt ttcagaagtt tcggccaccc cagacttgaa  11760
gcagtaacgg ctgctgaaaa tgttaggaaa tacatgaatc agcctaaagt cattgtgtat  11820
gagactctga tgaaaggtca tgccatatttt tgtggaatca taatcaacgg ctatcgtgac  11880
aggcacggag gcagttggcc accgctgacc ctccccctgc atgctgcaga cacaatccgg  11940
```

```
aatgctcaag cttcaggtga agggttaaca catgagcagt gcgttgataa ctggaaatct  12000
tttgctggag tgaaatttgg ctgctttatg cctcttagcc tggatagtga tctgacaatg  12060
tacctaaagg acaaggcact tgctgctctc caaagggaat gggattcagt ttacccgaaa  12120
gagttcctgc gttacgaccc tcccaaggga accgggtcac ggaggcttgt agatgttttc  12180
cttaatgatt cgagctttga cccatatgat gtgataatgt atgttgtaag tggagcttac  12240
ctccatgacc ctgagttcaa cctgtcttac agcctgaaag aaaaggagat caaggaaaca  12300
ggtagacttt ttgctaaaat gacttacaaa atgagggcat gccaagtgat tgctgaaaat  12360
ctaatctcaa acgggattgg caaatatttt aaggacaatg ggatggccaa ggatgagcac  12420
gatttgacta aggcactcca cactctagct gtctcaggag tccccaaaga tctcaaagaa  12480
agtcacaggg gggggccagt cttaaaaacc tactcccgaa gcccagtcca cacaagtacc  12540
aggaacgtga gagcagcaaa agggtttata gggttccctc aagtaattcg gcaggaccaa  12600
gacactgatc atccggagaa tatggaagct tacgagacag tcagtgcatt tatcacgact  12660
gatctcaaga agtactgcct taattggaga tatgagacca tcagcttgtt tgcacagagg  12720
ctaaatgaga tttacggatt gccctcattt ttccagtggc tgcataagag gcttgagacc  12780
tctgtcctgt atgtaagtga ccctcattgc cccccgacc ttgacgccca tatcccgtta  12840
tataaagtcc ccaatgatca aatcttcatt aagtacccta tgggaggtat agaagggtat  12900
tgtcagaagc tgtggaccat cagcaccatt ccctatctat acctggctgc ttatgagagc  12960
ggagtaagga ttgcttcgtt agtgcaaggg gacaatcaga ccatagccgt aacaaaaagg  13020
gtacccagca catggcccta caaccttaag aaacggaag ctgctagagt aactagagat  13080
tactttgtaa ttcttaggca aaggctacat gatattggcc atcacctcaa ggcaaatgag  13140
acaattgttt catcacattt ttttgtctat tcaaaggaa tatattatga tgggctactt  13200
gtgtcccaat cactcaagag catcgcaaga tgtgtattct ggtcagagac tatagttgat  13260
gaaacaaggg cagcatgcag taatattgct acaacaatgg ctaaaagcat cgagagaggt  13320
tatgaccgtt accttgcata ttccctgaac gtcctaaaag tgatacagca aattctgatc  13380
tctcttggct tcacaatcaa ttcaaccatg acccgggatg tagtcatacc cctcctcaca  13440
aacaacgacc tcttaataag gatggcactg ttgcccgctc ctattggggg gatgaattat  13500
ctgaatatga gcaggctgtt tgtcagaaac atcggtgatc cagtaacatc atcaattgct  13560
gatctcaaga gaatgattct cgcctcacta atgcctgaag agaccctcca tcaagtaatg  13620
acacaacaac cggggactc ttcattccta gactgggcta gcgacccta ctcagcaaat  13680 cttgtatgtg tccagagcat cactagactc ctcaagaaca taactgcaag gtttgtcctg  13740
atccatagtc caaacccaat gttaaaagga ttattccatg atgacagtaa agaagaggac  13800
gagggactgg cggcattcct catggacagg catattatag tacctagggc agctcatgaa  13860
atcctggatc atagtgtcac aggggcaaga gagtctattg caggcatgct ggataccaca  13920
aaaggcttga ttcgagccag catgaggaag gggggttaa cctctcgagt gataaccaga  13980
ttgtccaatt atgactatga acaattcaga gcagggatgg tgctattgac aggaagaaag  14040
agaaatgtcc tcattgacaa agagtcatgt caagtcagc tggcgagagc tctaagaagc  14100
catatgtggg cgaggctagc tcgaggacgg cctatttacg gccttgaggt ccctgatgta  14160
ctagaatcta tgcgaggcca ccttattcgg cgtcatgaga catgtgtcat ctgcgagtgt  14220
ggatcagtca actacggatg gttttttgtc ccctcgggtt gccaactgga tgatattgac  14280
aaggaaacat catccttgag agtcccatat attggttcta ccactgatga gagaacagac  14340
```

```
atgaagcttg ccttcgtaag agccccaagt cgatccttgc gatctgctgt tagaatagca    14400
acagtgtact catgggctta cggtgatgat gatagctctt ggaacgaagc ctggttgttg    14460
gctaggcaaa gggccaatgt gagcctggag gagctaaggg tgatcactcc catctcaact    14520
tcgactaatt tagcgcatag gttgagggat cgtagcactc aagtgaaata ctcaggtaca    14580
tcccttgtcc gagtggcgag gtataccaca atctccaacg acaatctctc atttgtcata    14640
tcagataaga aggttgatac taacttttata taccaacaag gaatgctcct agggttgggt    14700
gttttagaaa cattgtttcg actcgagaaa gataccggat catctaacac ggtattacat    14760
cttcacgtcg aaacagattg ttgcgtgatc ccgatgatag atcatcccag gatacccagc    14820
tcccgcaagc tagagctgag ggcagagcta tgtaccaacc cattgatata tgataatgca    14880
cctttaattg acagagatgc aacaaggcta tacacccaga gccataggag gcaccttgtg    14940
gaatttgtta catggtccac accccaacta tatcacattt tagctaagtc cacagcacta    15000
tctatgattg acctggtaac aaaatttgag aaggaccata tgaatgaaat ttcagctctc    15060 atagggggatg acgatatcaa tagtttcata actgagtttc tgctcataga gccaagatta    15120
ttcactatct acttgggcca gtgtgcggcc atcaattggg catttgatgt acattatcat    15180
agaccatcag ggaaatatca gatgggtgag ctgttgtcat cgttcctttc tagaatgagc    15240
aaaggagtgt ttaaggtgct tgtcaatgct ctaagccacc caaagatcta caagaaattc    15300
tggcattgtg gtattataga gcctatccat ggtccttcac ttgatgctca aaacttgcac    15360
acaactgtgt gcaacatggt ttacacatgc tatatgacct acctcgacct gttgttgaat    15420
gaagagttag aagagttcac atttctcttg tgtgaaagcg acgaggatgt agtaccggac    15480
agattcgaca acatccaggc aaaacactta tgtgttctgg cagatttgta ctgtcaacca    15540
gggacctgcc caccaattcg aggtctaaga ccggtagaga aatgtgcagt tctaaccgac    15600
catatcaagg cagaggctat gttatctcca gcaggatctt cgtggaacat aaatccaatt    15660
attgtagacc attactcatg ctctctgact tatctccggc gaggatcgat caaacagata    15720
agattgagag ttgatccagg attcatttttc gacgccctcg ctgaggtaaa tgtcagtcag    15780
ccaaagatcg gcagcaacaa catctcaaat atgagcatca aggctttcag accccccacac    15840 gatgatgttg caaaattgct caaagatatc aacacaagca agcacaatct tcccatttca    15900 ggggggcaatc tcgccaatta tgaaatccat gctttccgca gaatcgggtt gaactcatct    15960
gcttgctaca agctgttga gatatcaaca ttaattagga gatgccttga gccaggggag    16020
gacggcttgt tcttgggtga gggatcgggt tctatgttga tcacttataa ggagatactt    16080
aaactaaaca agtgcttcta taatagtggg gtttccgcca attctagatc tggtcaaagg    16140
gaattagcac cctatccctc cgaagttggc cttgtcgaac acagaatggg agtaggtaat    16200
attgtcaaag tgctctttaa cgggaggccc gaagtcacgt gggtaggcag tgtagattgc    16260
ttcaatttca tagttagtaa tatccctacc tctagtgtgg ggtttatcca ttcagatata    16320
gagaccttgc ctgacaaaga tactatagag aagctagagg aattggcagc catcttatcg    16380
atggctctgc tcctgggcaa aataggatca atactggtga ttaagcttat gccttttcagc    16440 ggggatttttg ttcagggatt tataagttat gtagggtctc attatagaga agtgaacctt    16500 gtataccccta gatacagcaa cttcatatct actgaatctt atttggttat gacagatctc    16560
aaggctaacc ggctaatgaa tcctgaaaag attaagcagc agataattga atcatctgtg    16620
aggacttcac ctggacttat aggtcacatc ctatccatta agcaactaag ctgcatacaa    16680
```

```
gcaattgtgg gagacgcagt tagtagaggt gatatcaatc ctactctgaa aaaacttaca   16740
cctatagagc aggtgctgat caattgcggg ttggcaatta acggacctaa gctgtgcaaa   16800
gaattgatcc accatgatgt tgcctcaggg caagatggat tgcttaattc tatactcatc   16860
ctctacaggg agttggcaag attcaaagac aaccaaagaa gtcaacaagg gatgttccac   16920 gcttacccg tattggtaag tagcaggcaa cgagaactta tatctaggat cacccgcaaa    16980
ttttgggggc acattcttct ttactccggg aacagaaagt tgataaataa gtttatccag   17040
aatctcaagt ccggctatct gatactagac ttacaccaga atatcttcgt taagaatcta   17100
tccaagtcag agaaacagat tattatgacg gggggtttga acgtgagtg ggttttttaag   17160 gtaacagtca aggagaccaa agaatggtat aagttagtcg gatacagtgc cctgattaag   17220
gactaattgg ttgaactccg gaaccctaat cctgccctag gtggttaggc attatttgca   17280
atatattaaa gaaaactttg aaaatacgaa gtttctattc ccagctttgt ctggtggccg   17340
gcatggtccc agcctcctcg ctggcgccgg ctggcaaca ttccgagggg accgtcccct    17400
cggtaatggc gaatgggacg cggccgatcc ggctgctaac aaagcccgaa aggaagctga   17460
gttggctgct gccaccgctg agcaataact agcataaccc cttggggcct ctaaacgggt   17520
cttgaggggt ttttttgctga aaggaggaac tatatccgga tgcggccgca ggtacccagc   17580
ttttgttccc tttagtgagg gttaatttcg agcttggcgt aatcatggtc atagctgttt   17640
cctgtgtgaa attgttatcc gctcacaatt ccacacaaca tacgagccgg aagcataaag   17700
tgtaaagcct ggggtgccta atgagtgagc taactcacat taattgcgtt gcgctcactg   17760
cccgctttcc agtcgggaaa cctgtcgtgc cagctgcatt aatgaatcgg ccaacgcgcg   17820
gggagaggcg gtttgcgtat tgggcgctct tccgcttcct cgctcactga ctcgctgcgc   17880
tcggtcgttc ggctgcggcg agcggtatca gctcactcaa aggcggtaat acggttatcc   17940
acagaatcag gggataacgc aggaaagaac atgtgagcaa aaggccagca aaaggccagg   18000
aaccgtaaaa aggccgcgtt gctggcgttt ttccataggc tccgcccccc tgacgagcat   18060
cacaaaaatc gacgctcaag tcagaggtgg cgaaacccga caggactata aagataccag   18120
gcgtttcccc ctggaagctc cctcgtgcgc tctcctgttc cgaccctgcc gcttaccgga   18180
tacctgtccg cctttctccc ttcgggaagc gtggcgcttt ctcatagctc acgctgtagg   18240
tatctcagtt cggtgtaggt cgttcgctcc aagctgggct gtgtgcacga accccccgtt   18300
cagcccgacc gctgcgcctt atccggtaac tatcgtcttg agtccaaccc ggtaagacac   18360
gacttatcgc cactggcagc agccactggt aacaggatta gcagagcgag gtatgtaggc   18420
ggtgctacag agttcttgaa gtggtggcct aactacggct acactagaag gacagtattt   18480
ggtatctgcg ctctgctgaa gccagttacc ttcggaaaaa gagttggtag ctcttgatcc   18540
ggcaaacaaa ccaccgctgg tagcggtggt ttttttgttt gcaagcagca gattacgcgc   18600
agaaaaaaag gatctcaaga agatcctttg atcttttcta cggggtctga cgctcagtgg   18660
aacgaaaact cacgttaagg gattttggtc atgagattat caaaaaggat cttcacctag   18720
atccttttaa attaaaaatg aagttttaaa tcaatctaaa gtatatatga gtaaacttgg   18780
tctgacagtt accaatgctt aatcagtgag gcacctatct cagcgatctg tctatttcgt   18840
tcatccatag ttgcctgact ccccgtcgtg tagataacta cgatacggga gggcttacca   18900
tctggcccca gtgctgcaat gataccgcga gacccacgct caccggctcc agatttatca   18960
gcaataaacc agccagccgg aagggccgag cgcagaagtg gtcctgcaac tttatccgcc   19020
tccatccagt ctattaattg ttgccgggaa gctagagtaa gtagttcgcc agttaatagt   19080
```

```
ttgcgcaacg ttgttgccat tgctacaggc atcgtggtgt cacgctcgtc gtttggtatg    19140
gcttcattca gctccggttc ccaacgatca aggcgagtta catgatcccc catgttgtgc    19200
aaaaaagcgg ttagctcctt cggtcctccg atcgttgtca gaagtaagtt ggccgcagtg    19260
ttatcactca tggttatggc agcactgcat aattctctta ctgtcatgcc atccgtaaga    19320
tgcttttctg tgactggtga gtactcaacc aagtcattct gagaatagtg tatgcggcga    19380
ccgagttgct cttgcccggc gtcaatacgg gataataccg cgccacatag cagaacttta    19440
aaagtgctca tcattggaaa acgttcttcg gggcgaaaac tctcaaggat cttaccgctg    19500
ttgagatcca gttcgatgta acccactcgt gcacccaact gatcttcagc atctttttact   19560 ttcaccagcg tttctgggtg agcaaaaaca ggaaggcaaa atgccgcaaa aaagggaata    19620
agggcgacac ggaaatgttg aatactcata ctcttccttt ttcaatatta ttgaagcatt    19680
tatcagggtt attgtctcat gagcggatac atatttgaat gtatttagaa aaataaacaa    19740 atagggttc cgcgcacatt tccccgaaaa gtgc                                 19774

<210> SEQ ID NO 3
<211> LENGTH: 1518
<212> TYPE: DNA
<213> ORGANISM: Human Papilloma Virus

<400> SEQUENCE: 3
atgagcctgt ggctgcccag cgaggccacc gtgtacctgc cccccgtgcc cgtgagcaag      60
gtggtgagca ccgacgagta cgtggccagg accaacatct actaccacgc cggcaccagc     120
aggctgctgg ccgtgggcca ccctacttc cccatcaaga gcccaacaa caacaagatc       180 ctggtgccca aggtgagcgg cctgcagtac agggtgttca ggatccacct gcccgacccc     240
aacaagttcg gcttccccga caccagcttc tacaacccg acacccagag ctggtgtgg       300 gcctgcgtgg gcgtggaggt gggcaggggc cagcccctgg gcgtgggcat cagcggccac     360
cccctgctga acaagctgga cgacaccgag aacgccagcg cctacgccgc caacgccggc     420
gtggacaaca gggagtgcat cagcatggac tacaagcaga cccagctgtg cctgatcggc     480
tgcaagcccc ccatcggcga gcactggggc aagggcagcc cctgcaccaa cgtggccgtg     540
aaccccggcg actgcccccc cctggagctg atcaacaccg tgatccagga cggcgacatg     600
gtggacaccg gcttcggcgc catggacttc accaccctgc aggccaacaa gagcgaggtg     660
cccctggaca tctgcaccag catctgcaag taccccgact acatcaagat ggtgagcgag     720
ccctacggcg acagcctgtt cttctacctg aggagggagc agatgttcgt gaggcacctg     780
ttcaacaggg ccggcgccgt gggcgagaac gtgcccgacg acctgtacat caagggcagc     840
ggcagcaccg ccaacctggc cagcagcaac tacttcccca cccccagcgg cagcatggtg     900
accagcgacg cccagatctt caacaagccc tactggctgc agagggccca gggccacaac     960
aacggcatct gctggggcaa ccagctgttc gtgaccgtgg tggacaccac caggagcacc    1020
aacatgagcc tgtgcgccgc catcagcacc agcgagacca cctacaagaa caccaacttc    1080
aaggagtacc tgaggcacgg cgaggagtac gacctgcagt tcatcttcca gctgtgcaag    1140
atcaccctga ccgccgacgt gatgacctac atccacagca tgaacagcac catcctggag    1200
gactggaact tcggcctgca gccccccccc ggcggcaccc tggaggacac ctacaggttc    1260
gtgaccagcc aggccatcgc ctgccagaag cacaccccc ccgcccccaa ggaggacccc    1320
ctgaagaagt acaccttctg ggaggtgaac ctgaaggaga agttcagcgc cgacctggac    1380
```

| | |
|---|---|
| cagttccccc tgggcaggaa gttcctgctg caggccggcc tgaaggccaa gcccaagttc | 1440 |
| accctgggca agaggaaggc cacccccacc accagcagca ccagcaccac cgccaagagg | 1500 |
| aagaagagga agctgtga | 1518 |

<210> SEQ ID NO 4
<211> LENGTH: 1422
<212> TYPE: DNA
<213> ORGANISM: Human Papilloma Virus

<400> SEQUENCE: 4

| | |
|---|---|
| atgcgacaca acgttctgc aaaacgcaca aacgtgcat cggctaccca actttataaa | 60 |
| acatgcaaac aggcaggtac atgtccacct gacattatac ctaaggttga aggcaaaact | 120 |
| attgctgaac aaatattaca atatggaagt atgggtgtat tttttggtgg gttaggaatt | 180 |
| ggaacagggt cgggtacagg cggacgcact gggtatattc cattgggaac aaggcctccc | 240 |
| acagctacag atacacttgc tcctgtaaga ccccctttaa cagtagatcc tgtgggccct | 300 |
| tctgatcctt ctatagtttc tttagtggaa gaaactagtt ttattgatgc tggtgcacca | 360 |
| acatctgtac cttccattcc cccagatgta tcaggattta gtattactac ttcaactgat | 420 |
| accacacctg ctatattaga tattaataat actgttacta ctgttactac ataataat | 480 |
| cccactttca ctgacccatc tgtattgcag cctccaacac ctgcagaaac tggagggcat | 540 |
| tttacacttt catcatccac tattagtaca cataattatg aagaaattcc tatggataca | 600 |
| tttattgtta gcacaaaccc taacacagta actagtagca cacccatacc agggtctcgc | 660 |
| ccagtggcac gcctaggatt atatagtcgc acaacacaac aggttaaagt tgtagaccct | 720 |
| gcttttgtaa ccactcccac taaacttatt acatatgata atcctgcata tgaaggtata | 780 |
| gatgtggata atacattata tttttctagt aatgataata gtattaatat agctccagat | 840 |
| cctgactttt tggatatagt tgctttacat aggccagcat taacctctag gcgtactggc | 900 |
| attaggtaca gtagaattgg taataaacaa acactacgta ctcgtagtgg aaaatctata | 960 |
| ggtgctaagg tacattatta ttatgattta agtactattg atcctgcaga agaaatagaa | 1020 |
| ttacaaacta taacaccttc tacatatact accacttcac atgcagcctc acctacttct | 1080 |
| attaataatg gattatatga tatttatgca gatgacttta ttacagatac ttctacaacc | 1140 |
| ccggtaccat ctgtaccctc tacatcttta tcaggttata ttcctgcaaa tacaacaatt | 1200 |
| ccttttggtg gtgcatacaa tattccttta gtatcaggtc ctgatatacc cattaatata | 1260 |
| actgaccaag ctccttcatt aattcctata gttccagggt ctccacaata tacaattatt | 1320 |
| gctgatgcag gtgacttta tttacatcct agttattaca tgttacgaaa acgacgtaaa | 1380 |
| cgtttaccat attttttttc agatgtctct ttggctgcct ag | 1422 |

<210> SEQ ID NO 5
<211> LENGTH: 477
<212> TYPE: DNA
<213> ORGANISM: Human Papilloma Virus

<400> SEQUENCE: 5

| | |
|---|---|
| atgcaccaaa agagaactgc aatgtttcag gacccacagg agcgacccag aaagttacca | 60 |
| cagttatgca cagagctgca acaactata catgatataa tattagaatg tgtgtactgc | 120 |
| aagcaacagt tactgcgacg tgaggtatat gactttgctt tcgggatttt atgcatagta | 180 |
| tatagagatg gaatcccata tgctgtatgt gataaatgtt taagttttta ttctaaaatt | 240 |
| agtgagtata gacattattg ttatagtttg tatggaacaa cattagaaca gcaatacaac | 300 |

```
aaaccgttgt gtgatttgtt aattaggtgt attaactgtc aaaagccact gtgtcctgaa    360
gaaaagcaaa gacatctgga caaaaagcaa agattccata atataagggg tcggtggacc    420
ggtcgatgta tgtcttgttg cagatcatca agaacacgta gagaaaccca gctgtaa       477

<210> SEQ ID NO 6
<211> LENGTH: 297
<212> TYPE: DNA
<213> ORGANISM: Human Papilloma Virus

<400> SEQUENCE: 6
atgcatggag atacacctac attgcatgaa tatatgttag atttgcaacc agagacaact    60
gatctctact gttatgagca attaaatgac agctcagagg aggaggatga aatagatggt    120
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcagaa accataa      297

<210> SEQ ID NO 7
<211> LENGTH: 1707
<212> TYPE: DNA
<213> ORGANISM: Human Papilloma Virus

<400> SEQUENCE: 7
atgtgcctgt atacacgggt cctgatatta cattaccatc tactacctct gtatggccca    60
ttgtatcacc cacggcccct gcctctacac agtatattgg tatacatggt acacattatt    120
atttgtggcc attatattat tttattccta agaaacgtaa acgtgttccc tatttttttg    180
cagatggctt tgtggcggcc tagtgacaat accgtatatc ttccacctcc ttctgtggca    240
agagttgtaa ataccgatga ttatgtgact cccacaagca tattttatca tgctggcagc    300
tctagattat taactgttgg taatccatat tttagggttc ctgcaggtgg tggcaataag    360
caggatattc ctaaggtttc tgcataccaa tatagagtat ttagggtgca gttacctgac    420
ccaaataaat ttggtttacc tgatactagt atttataatc ctgaaacaca acgtttagtg    480
tgggcctgtg ctggagtgga aattggccgt ggtcagcctt taggtgttgg ccttagtggg    540
catccatttt ataataaatt agatgacact gaaagttccc atgccgccac gtctaatgtt    600
tctgaggacg ttagggacaa tgtgtctgta gattataagc agacacagtt atgtatttg    660 ggctgtgccc ctgctattgg ggaacactgg gctaaaggca ctgcttgtaa atcgcgtcct    720
ttatcacagg gcgattgccc cccttttaga acttaaaaaca cagttttgga agatggtgat    780
atggtagata ctggatatgg tgccatggac tttagtacat tgcaagatac taaatgtgag    840
gtaccattgg atatttgtca gtctatttgt aaatatcctg attatttaca aatgtctgca    900
gatccttatg gggattccat gtttttttgc ttacggcgtg agcagctttt tgctaggcat    960
ttttggaata gagcaggtac tatgggtgac actgtgcctc aatccttata tattaaaggc   1020
acaggtatgc ctgcttcacc tggcagctgt gtgtattctc cctctccaag tggctctatt   1080
gttacctctg actcccagtt gtttaataaa ccatattggt tacataaggc acagggtcat   1140
aacaatggtg tttgctggca taatcaatta tttgttactg tggtagatac cactcccagt   1200
accaatttaa caatatgtgc ttctacacag tctcctgtac ctgggcaata tgatgctacc   1260
aaatttaagc agtatagcag acatgttgag gaatatgatt tgcagtttat ttttcagttg   1320
tgtactatta ctttaactgc agatgttatg tcctatattc atagtatgaa tagcagtatt   1380
```

| | |
|---|---|
| ttagaggatt ggaactttgg tgttcccccc cccccaacta ctagtttggt ggatacatat | 1440 |
| cgttttgtac aatctgttgc tattacctgt caaaaggatg ctgcaccggc tgaaaataag | 1500 |
| gatccctatg ataagttaaa gttttggaat gtggatttaa aggaaaagtt ttctttagac | 1560 |
| ttagatcaat atcccctttgg acgtaaattt ttggttcagg ctggattgcg tcgcaagccc | 1620 |
| accataggcc ctcgcaaacg ttctgctcca tctgccacta cgtcttctaa acctgccaag | 1680 |
| cgtgtgcgtg tacgtgccag gaagtaa | 1707 |

<210> SEQ ID NO 8
<211> LENGTH: 1389
<212> TYPE: DNA
<213> ORGANISM: Human Papilloma Virus

<400> SEQUENCE: 8

| | |
|---|---|
| atggtatccc accgtgccgc acgacgcaaa cgggcttcgg taactgactt atataaaaca | 60 |
| tgtaaacaat ctggtacatg tccacctgat gttgttccta aggtggaggg caccacgtta | 120 |
| gcagataaaa tattgcaatg gtcaagcctt ggtatatttt gggtggact tggcataggt | 180 |
| actggcagtg gtacaggggg tcgtacaggg tacattccat gggtgggcg ttccaataca | 240 |
| gtggtggatg ttggtcctac acgtccccca gtggttattg aacctgtggg ccccacagac | 300 |
| ccatctattg ttacattaat agaggactcc agtgtggtta catcaggtgc acctaggcct | 360 |
| acgtttactg gcacgtctgg gtttgatata acatctgcgg gtacaactac acctgcggtt | 420 |
| ttggatatca ccttcgtc tacctctgtg tctatttcca caaccaattt taccaatcct | 480 |
| gcattttctg atccgtccat tattgaagtt ccacaaactg gggaggtggc aggtaatgta | 540 |
| tttgttggta cccctacatc tggaacacat gggtatgagg aaatacccttt acaaacattt | 600 |
| gcttcttctg gtacggggga ggaacccatt agtagtaccc cattgcctac tgtgcggcgt | 660 |
| gtagcaggtc cccgccttta cagtagggcc taccaacaag tgtcagtggc taaccctgag | 720 |
| tttcttacac gtccatcctc tttaattaca tatgacaacc cggcctttga gcctgtggac | 780 |
| actacattaa catttgatcc tcgtagtgat gttcctgatt cagattttat ggatattatc | 840 |
| cgtctacata ggcctgcttt aacatccagg cgtgggactt tcgctttag tagattaggt | 900 |
| caacgggcaa ctatgtttac ccgcagcggt acacaaatag gtgctagggt tcactttat | 960 |
| catgatataa gtcctattgc accttccca gaatatattg aactgcagcc tttagtatct | 1020 |
| gccacggagg acaatgactt gtttgatata tatgcagatg acatggaccc tgcagtgcct | 1080 |
| gtaccatcgc gttctactac ctccttgca ttttttaaat attcgcccac tatatcttct | 1140 |
| gcctcttcct atagtaatgt aacggtccct ttaacctcct cttgggatgt gcctgtatac | 1200 |
| acgggtcctg atattacatt accatctact acctctgtat ggcccattgt atcacccacg | 1260 |
| gcccctgcct ctacacagta tattggtata catggtacac attattattt gtggccatta | 1320 |
| tattatttta ttcctaagaa acgtaaacgt gttccctatt tttttgcaga tggctttgtg | 1380 |
| gcggcctag | 1389 |

<210> SEQ ID NO 9
<211> LENGTH: 477
<212> TYPE: DNA
<213> ORGANISM: Human Papilloma Virus

<400> SEQUENCE: 9

| | |
|---|---|
| atggcgcgct ttgaggatcc aacacggcga ccctacaagc tacctgatct gtgcacggaa | 60 |
| ctgaacactt cactgcaaga catagaaata acctgtgtat attgcaagac agtattggaa | 120 |

```
cttacagagg tatttgaatt tgcatttaaa gatttatttg tggtgtatag agacagtata      180
ccccatgctg catgccataa atgtatagat ttttattcta gaattagaga attaagacat      240
tattcagact ctgtgtatgg agacacattg gaaaaactaa ctaacactgg gttatacaat      300
ttattaataa ggtgcctgcg gtgccagaaa ccgttgaatc cagcagaaaa acttagacac      360
cttaatgaaa aacgacgatt tcacaacata gctgggcact atagaggcca gtgccattcg      420
tgctgcaacc gagcacgaca ggaacgactc caacgacgca gagaaacaca agtataa        477

<210> SEQ ID NO 10
<211> LENGTH: 318
<212> TYPE: DNA
<213> ORGANISM: Human Papilloma Virus

<400> SEQUENCE: 10
atgcatggac ctaaggcaac attgcaagac attgtattgc atttagagcc ccaaaatgaa       60
attccggttg accttctatg tcacgagcaa ttaagcgact cagaggaaga aaacgatgaa      120
atagatggag ttaatcatca acatttacca gcccgacgag ccgaaccaca acgtcacaca      180
atgttgtgta tgtgttgtaa gtgtgaagcc agaattgagc tagtagtaga aagctcagca      240
gacgaccttc gagcattcca gcagctgttt ctgaacaccc tgtcctttgt gtgtccgtgg      300
tgtgcatccc agcagtaa                                                    318

<210> SEQ ID NO 11
<211> LENGTH: 1503
<212> TYPE: DNA
<213> ORGANISM: Human Papilloma Virus

<400> SEQUENCE: 11
atgtggcggc ctagcgacag cacagtatat gtgcctcctc ctaaccctgt atccaaagtt       60
gttgccacgg atgcttatgt tactcgcacc aacatatttt atcatgccag cagttctaga      120
cttcttgcag tgggtcatcc ttatttttcc ataaaacggg ctaacaaaac tgttgtgcca      180
aaggtgtcag atatcaata cagggtattt aaggtggtgt taccagatcc taacaaattt      240
gcattgcctg actcgtctct ttttgatccc acaacacaac gtttggtatg gcatgcaca      300 ggcctagagg tgggcagggg acagccatta ggtgtgggtg taagtggaca tccttttcta      360
aataaatatg atgatgttga aaattcaggg agtggtggta accctggaca ggataacagg      420
gttaatgttg gtatggatta taaacaaaca caattatgca tggttggatg tgccccccct      480
ttgggcgagc attggggtaa aggtaaacag tgtactaata cacctgtaca ggctggtgac      540
tgcccgccct tagaacttat taccagtgtt atacaggatg cgatatggt tgacacaggc      600 tttggtgcta tgaattttgc tgatttgcag accaataaat cagatgttcc tatttacata      660
tgtggcacta catgtaaata tccagattat ttacaaatgg ctgcagaccc atatggtgat      720
agattatttt tttttctacg gaaggaacaa atgtttgcca acatttttt taacagggct      780 ggcgaggtgg gggaacctgt gcctgatact cttataatta agggtagtgg aaatcgaacg      840
tctgtaggga gtagtatata tgttaacacc ccaagcggct ctttggtgtc ctctgaggca      900
caattgttta ataagccata ttggctacaa aaagcccagg acataacaa tggtatttgt      960 tggggtaatc aactgttttgt tactgtggta gataccacac gcagtaccaa catgacatta     1020
tgtgcatccg taactacatc ttccacatac accaattctg attataaaga gtacatgcgt     1080
catgtggaag agtatgattt acaatttatt tttcaattat gtagcattac attgtctgct     1140
```

| | |
|---|---|
| gaagtaatgg cctatattca caatgaat ccctctgttt tggaagactg aactttggg | 1200 |
| ttatcgcctc ccccaaatgg tacattagaa gataccctata ggtatgtgca gtcacaggcc | 1260 |
| attacctgtc aaaagcccac tcctgaaaag gaaaagccag atccctataa gaaccttagt | 1320 |
| ttttgggagg ttaatttaaa agaaaagttt tctagtgaat tggatcagta tccttttggga | 1380 |
| cgcaagtttt tgttacaaag tggatatagg ggacggtcct ctattcgtac cggtgttaag | 1440 |
| cgccctgctg tttccaaagc ctctgctgcc cctaaacgta agcgcgccaa aaccaaaagg | 1500 |
| taa | 1503 |

<210> SEQ ID NO 12
<211> LENGTH: 1380
<212> TYPE: DNA
<213> ORGANISM: Human Papilloma Virus

<400> SEQUENCE: 12

| | |
|---|---|
| atggcacata gtagggcccg acgacgcaag cgtgcgtcag ctacacagct atatcaaaca | 60 |
| tgtaaactca ctggaacatg ccccccagat gtaattccta aggtggaaca caacaccatt | 120 |
| gcagatcaaa tattaaaatg ggggagtttg ggggtgtttt ttggagggtt gggtataggc | 180 |
| accggttccg gcactggggg tcgtactggc tatgttccct taggaacttc tgcaaaacct | 240 |
| tctattacta gtgggcctat ggctcgtcct cctgtggtgg tggagcctgt ggccccttcg | 300 |
| gatccatcca ttgtgtcttt aattgaagaa tcggcaatca ttaacgcagg ggcgcctgaa | 360 |
| attgtgcccc ctgcacacgg tgggtttaca attacatcct ctgaaacaac taccctgca | 420 |
| atattggatg tatcagttac tagtcatact actactagta tatttagaaa tcctgtcttt | 480 |
| acagaacctt ctgtaacaca accccaacca cccgtggagg ctaatggaca tatattaatt | 540 |
| tctgcaccca ctataacgtc acaccctata gaggaaattc ctttagatac ttttgtgata | 600 |
| tcctctagtg atagcggtcc tacatccagt acccctgttc ctggtactgc acctcggcct | 660 |
| cgtgtgggcc tatatagtcg tgcattgcac caggtgcagg ttacagaccc tgcatttctt | 720 |
| tccactcctc aacgcttaat tacatatgat aaccctgtat atgaagggga ggatgttagt | 780 |
| gtacaattta gtcatgattc tatacacaat gcacctgatg aggcttttat ggacataatt | 840 |
| cgtttgcaca gacctgctat tgcgtcccga cgtggccttg tgcggtacag tcgcattgga | 900 |
| caacgggggt ctatgcacac tcgcagcgga aagcacatag ggcccgcat tcattatttt | 960 |
| tatgatattt cacctattgc acaagctgca gaagaaatag aaatgcaccc tcttgtggct | 1020 |
| gcacaggaag atacatttga tatttatgct gaatctttg aacctgacat taaccctacc | 1080 |
| caacaccctg ttacaaatat atcagataca tatttaactt ccacacctaa tacagttaca | 1140 |
| caaccgtggg gtaacaccac agttccattg tcaattccta atgacctgtt tttacagtct | 1200 |
| ggccctgata taacttttcc tactgcacct atgggaacac ccttagtcc tgtaactcct | 1260 |
| gcttacctta caggccctgt tttcattaca ggttctggat tttatttgca tcctgcatgg | 1320 |
| tattttgcac gtaaacgccg taaacgtatt cccttatttt tttcagatgt ggcggcctag | 1380 |

<210> SEQ ID NO 13
<211> LENGTH: 453
<212> TYPE: DNA
<213> ORGANISM: Human Papilloma Virus

<400> SEQUENCE: 13

| | |
|---|---|
| atggaaagtg caaatgcctc cacgtctgca acgaccatag accagttgtg caagacgttt | 60 |
| aatctatcta tgcatacgtt gcaaattaat tgtgtgtttt gcaagaatgc actgaccact | 120 |

```
gcagagattt attcatatgc atataaacag ctaaaggtcc tgtttcgagg cggctatcca      180
tatgcagcct gcgcgtgctg cctagaattt catggaaaaa ttaaccaata tagacacttt      240
gattatgctg gatatgcaac aactgttgaa gaagaaacta aacaagacat tttagacgtg      300
ctaattcggt gctacctgtg tcacaaaccg ctgtgtgaag tagaaaaggt aaaacatata      360
ctaaccaagg cacggttcat aaagctaaat tgtacgtgga agggtcgctg cctacactgc      420
tggacaacat gcatggaaga catgttaccc taa                                   453

<210> SEQ ID NO 14
<211> LENGTH: 297
<212> TYPE: DNA
<213> ORGANISM: Human Papilloma Virus

<400> SEQUENCE: 14
atgcatggaa gacatgttac cctaaaggat attgtattag acctgcaacc tccagaccct       60
gtagggttac attgctatga gcaattagta gacagctcag aagatgaggt ggacgaagtg      120
gacggacaag attcacaacc tttaaaacaa cattaccaaa tagtgacctg ttgctgtgga      180
tgtgacagca acgttcgact ggttgtgcag tgtacagaaa cagacatcag agaagtgcaa      240
cagcttctgt tgggaacact aaacatagtg tgtcccatct gcgcaccgaa gacataa        297
```